United States Patent
Anderson et al.

(10) Patent No.: US 10,232,111 B2
(45) Date of Patent: Mar. 19, 2019

(54) PUMP, MOTOR AND ASSEMBLY FOR BENEFICIAL AGENT DELIVERY

(71) Applicant: ABBVIE INC., North Chicago, IL (US)

(72) Inventors: Phil D. Anderson, Libertyville, IL (US); Gurjinder Dhami, Neenah, WI (US); Scott Smieja, Oshkosh, WI (US)

(73) Assignee: ABBVIE INC., North Chicago, IL (US)

( * ) Notice: Subject to any disclaimer, the term of this patent is extended or adjusted under 35 U.S.C. 154(b) by 369 days.

(21) Appl. No.: 14/586,923

(22) Filed: Dec. 30, 2014

(65) Prior Publication Data
US 2015/0184648 A1 Jul. 2, 2015

Related U.S. Application Data

(60) Provisional application No. 62/054,134, filed on Sep. 23, 2014, provisional application No. 61/922,709, filed on Dec. 31, 2013.

(51) Int. Cl.
*F04B 43/08* (2006.01)
*A61M 5/168* (2006.01)
(Continued)

(52) U.S. Cl.
CPC ........ *A61M 5/16831* (2013.01); *A61M 5/142* (2013.01); *A61M 5/14228* (2013.01);
(Continued)

(58) Field of Classification Search
CPC .............. A61M 5/16831; A61M 5/142; A61M 5/14228; A61M 5/14244; A61M 2205/16;
(Continued)

(56) References Cited

U.S. PATENT DOCUMENTS 1,708,333 A 4/1929 Smith
1,874,667 A 8/1932 Yoshinobu
(Continued)

FOREIGN PATENT DOCUMENTS

EP 0624716 * 11/1994
EP 0 923 392 A1 6/1999
(Continued)

OTHER PUBLICATIONS

U.S. Appl. No. 14/586,927, filed Dec. 30, 2014.
(Continued)

*Primary Examiner* — Charles G Freay
(74) *Attorney, Agent, or Firm* — Baker Botts L.L.P.

(57) ABSTRACT

Pump includes a motor and a cam shaft coupled to the motor for rotation about a longitudinal axis of the cam shaft. The cam shaft has at least one radially-outward projection defining a helical engagement portion disposed along a length of the cam shaft. A plurality of finger plates are disposed along the length of the cam shaft, each finger plate mounted for movement in a transverse direction relative to the longitudinal axis of the cam shaft. Each finger plate has an aperture defined therein to receive the cam shaft therethrough. Each aperture has a substantially straight edge region and an opposing edge region. Engagement of the helical engagement portion with the substantially flat edge region during rotation of the cam shaft urges the finger plate transversely toward an extended position.

29 Claims, 53 Drawing Sheets

(51) Int. Cl.
*A61M 5/142* (2006.01)
*F04B 43/12* (2006.01)

(52) U.S. Cl.
CPC ........ *A61M 5/14244* (2013.01); *F04B 43/082* (2013.01); *F04B 43/12* (2013.01); *F04B 43/1223* (2013.01); *A61M 2005/16863* (2013.01); *A61M 2205/12* (2013.01); *A61M 2205/14* (2013.01); *A61M 2205/16* (2013.01); *A61M 2205/50* (2013.01); *A61M 2205/502* (2013.01); *A61M 2205/6054* (2013.01)

(58) Field of Classification Search
CPC ...... A61M 2205/14; A61M 2205/6054; A61M 2205/502; A61M 2205/12; A61M 2005/16863; A61M 2205/50; F04B 43/082; F04B 43/1223; F04B 43/12
USPC .................................................. 417/474, 479
See application file for complete search history.

(56) References Cited

U.S. PATENT DOCUMENTS

| | | | | |
|---|---|---|---|---|
| 1,922,196 | A * | 8/1933 | Butler | F04B 43/0072 417/474 |
| 3,233,553 | A | 2/1966 | Chanton | |
| 3,603,152 | A | 9/1971 | Alibert et al. | |
| 3,736,930 | A | 6/1973 | Georgi | |
| 3,985,467 | A | 10/1976 | Lefferson | |
| 4,174,637 | A | 11/1979 | Mulzet et al. | |
| 4,370,983 | A | 2/1983 | Lichtenstein | |
| 4,373,525 | A | 2/1983 | Kobayashi | |
| 4,394,862 | A | 7/1983 | Shim | |
| 4,460,355 | A | 7/1984 | Layman | |
| 4,482,347 | A | 11/1984 | Borsanyi | |
| 4,493,706 | A | 1/1985 | Borsanyi et al. | |
| 4,529,401 | A | 7/1985 | Leslie et al. | |
| 4,530,696 | A | 7/1985 | Bisera et al. | |
| 4,534,756 | A | 8/1985 | Nelson | |
| 4,562,751 | A | 1/1986 | Nason et al. | |
| 4,604,034 | A | 8/1986 | Wheeldon et al. | |
| 4,657,486 | A * | 4/1987 | Stempfle | A61M 5/142 417/12 |
| 4,671,792 | A * | 6/1987 | Borsanyi | F04B 43/082 128/DIG. 12 |
| 4,690,673 | A | 9/1987 | Bloomquist | |
| 4,710,163 | A | 12/1987 | Butterfield | |
| 4,743,228 | A | 5/1988 | Butterfield | |
| 4,816,019 | A | 3/1989 | Kamen | |
| 4,840,542 | A | 6/1989 | Abbott | |
| 4,867,744 | A | 9/1989 | Borsanyi | |
| 4,882,575 | A | 11/1989 | Kawahara | |
| 4,898,576 | A | 2/1990 | Philip | |
| 4,909,710 | A | 3/1990 | Kaplan et al. | |
| 4,954,046 | A * | 9/1990 | Irvin | A61M 5/14228 128/DIG. 12 |
| 4,979,940 | A | 12/1990 | Bobo, Jr. | |
| 5,078,682 | A | 1/1992 | Miki | |
| 5,087,245 | A | 2/1992 | Doan | |
| 5,092,749 | A | 3/1992 | Meijer | |
| 5,096,385 | A | 3/1992 | Georgi et al. | |
| 5,116,203 | A | 5/1992 | Natwick et al. | |
| 5,165,874 | A * | 11/1992 | Sancoff | A61M 5/14228 128/DIG. 12 |
| 5,190,522 | A | 3/1993 | Wojcicki et al. | |
| 5,211,548 | A * | 5/1993 | Okada | A61M 5/142 417/474 |
| 5,219,327 | A * | 6/1993 | Okada | A61M 5/14228 128/DIG. 12 |
| 5,242,408 | A | 9/1993 | Jhuboo et al. | |
| 5,292,306 | A | 3/1994 | Wynkoop et al. | |
| 5,295,967 | A | 3/1994 | Rondelet et al. | |
| 5,336,053 | A | 8/1994 | Wynkoop | |
| 5,354,273 | A | 10/1994 | Hagen | |
| 5,356,378 | A | 10/1994 | Doan | |
| 5,445,621 | A | 8/1995 | Poli et al. | |
| 5,472,420 | A | 12/1995 | Campbell | |
| 5,486,286 | A | 1/1996 | Peterson et al. | |
| 5,501,665 | A | 3/1996 | Jhuboo et al. | |
| 5,511,951 | A | 4/1996 | O'Leary | |
| 5,522,799 | A * | 6/1996 | Furukawa | A61M 5/142 128/DIG. 12 |
| 5,549,460 | A | 8/1996 | O'Leary | |
| 5,558,507 | A * | 9/1996 | Magnus | F04B 43/082 29/888.022 |
| 5,580,221 | A | 12/1996 | Triezenberg | |
| 5,609,576 | A | 3/1997 | Voss et al. | |
| 5,620,312 | A | 4/1997 | Hyman et al. | |
| 5,647,853 | A | 7/1997 | Feldmann et al. | |
| 5,695,473 | A | 12/1997 | Olsen | |
| 5,791,881 | A | 8/1998 | Moubayed et al. | |
| 5,803,712 | A | 9/1998 | Davis et al. | |
| 5,807,322 | A | 9/1998 | Lindsey et al. | |
| 5,808,203 | A | 9/1998 | Nolan, Jr. et al. | |
| 5,814,009 | A | 9/1998 | Wheatman | |
| 5,827,223 | A * | 10/1998 | Butterfield | A61M 5/16859 604/65 |
| 5,906,589 | A | 5/1999 | Gordon et al. | |
| 5,935,106 | A | 8/1999 | Olsen | |
| 5,938,413 | A * | 8/1999 | Makino | F04B 43/082 417/474 |
| 5,951,510 | A | 9/1999 | Barak | |
| 5,964,583 | A * | 10/1999 | Danby | F04B 43/082 417/474 |
| 5,980,490 | A | 11/1999 | Tsoukalis | |
| 5,988,983 | A | 11/1999 | Furusawa | |
| 5,989,222 | A | 11/1999 | Cole et al. | |
| 6,106,249 | A | 8/2000 | Barak | |
| 6,164,921 | A | 12/2000 | Moubayed et al. | |
| 6,203,296 | B1 | 3/2001 | Ray et al. | |
| 6,227,203 | B1 | 5/2001 | Rise et al. | |
| 6,253,968 | B1 * | 7/2001 | Van Dijk | G01F 11/088 222/181.2 |
| 6,358,225 | B1 | 3/2002 | Butterfield | |
| 6,371,732 | B1 | 4/2002 | Moubayed et al. | |
| 6,413,059 | B1 | 7/2002 | Pringle | |
| 6,416,291 | B1 | 7/2002 | Butterfield et al. | |
| 6,558,347 | B1 | 5/2003 | Jhuboo et al. | |
| 6,572,604 | B1 | 6/2003 | Platt et al. | |
| 6,620,151 | B2 | 9/2003 | Blischak et al. | |
| 6,656,148 | B2 | 12/2003 | Das et al. | |
| 6,659,980 | B2 | 12/2003 | Moberg et al. | |
| 6,786,885 | B2 | 9/2004 | Hochman et al. | |
| 6,942,637 | B2 | 9/2005 | Cartledge et al. | |
| 7,104,763 | B2 | 9/2006 | Bouton et al. | |
| 7,169,352 | B1 | 1/2007 | Felt et al. | |
| 7,241,115 | B2 | 7/2007 | Luongo et al. | |
| 7,255,680 | B1 | 8/2007 | Gharib | |
| 7,264,148 | B2 | 9/2007 | Tachibana | |
| 7,291,126 | B2 | 11/2007 | Shekalim | |
| 7,360,999 | B2 | 4/2008 | Nelson et al. | |
| 7,686,789 | B2 | 3/2010 | Nemoto et al. | |
| 7,867,192 | B2 | 1/2011 | Bowman et al. | |
| 7,881,883 | B2 | 2/2011 | Remde | |
| 7,955,060 | B2 * | 6/2011 | Gottschalk | F04B 43/082 417/477.1 |
| 7,998,111 | B2 | 8/2011 | Moberg et al. | |
| 8,111,159 | B2 | 2/2012 | Andreasson et al. | |
| 8,167,832 | B2 | 5/2012 | Bowman et al. | |
| 8,182,461 | B2 | 5/2012 | Pope et al. | |
| 8,317,099 | B2 | 11/2012 | Perkins et al. | |
| 8,317,770 | B2 | 11/2012 | Miesel et al. | |
| 8,330,579 | B2 | 12/2012 | Kneip et al. | |
| 8,371,832 | B2 | 2/2013 | Rotem et al. | |
| 8,378,837 | B2 | 2/2013 | Wang et al. | |
| 8,382,703 | B1 | 2/2013 | Abdelaal | |
| 8,394,081 | B2 | 3/2013 | Locke et al. | |
| 8,486,020 | B2 | 7/2013 | Hills et al. | |
| 8,500,673 | B2 | 8/2013 | Zanotti et al. | |
| 8,523,803 | B1 | 9/2013 | Favreau | |
| 8,535,025 | B2 | 9/2013 | Rotem et al. | |
| 8,547,239 | B2 | 10/2013 | Peatfield et al. | |
| 8,568,349 | B2 | 10/2013 | Shergold | |

(56) References Cited

U.S. PATENT DOCUMENTS

| | | |
|---|---|---|
| 8,591,448 B2 | 11/2013 | Powers et al. |
| 8,672,875 B2 | 3/2014 | Vanderveen et al. |
| 8,681,010 B2 | 3/2014 | Moberg et al. |
| 8,694,331 B2 | 4/2014 | DeBelser et al. |
| 8,734,376 B2 | 5/2014 | Simpson et al. |
| 8,752,436 B2 | 6/2014 | Beck et al. |
| 2002/0016568 A1 | 2/2002 | Lebel et al. |
| 2002/0128594 A1 | 9/2002 | Das et al. |
| 2002/0193679 A1 | 12/2002 | Malave et al. |
| 2003/0088238 A1 | 5/2003 | Poulsen et al. |
| 2003/0163088 A1 | 8/2003 | Blomquist |
| 2004/0051368 A1 | 3/2004 | Caputo et al. |
| 2005/0118048 A1 | 6/2005 | Traxinger |
| 2007/0179448 A1 | 8/2007 | Lim et al. |
| 2008/0273133 A1 | 11/2008 | Bae et al. |
| 2009/0067989 A1 | 3/2009 | Estes et al. |
| 2009/0275896 A1 | 11/2009 | Kamen et al. |
| 2010/0226101 A1 | 9/2010 | Yeates et al. |
| 2010/0296955 A1* | 11/2010 | Wolff .................... F04B 43/082 417/477.3 |
| 2011/0034900 A1 | 2/2011 | Yodfat et al. |
| 2011/0118694 A1 | 5/2011 | Yodfat et al. |
| 2011/0190852 A1 | 8/2011 | Dinsmoor et al. |
| 2011/0270219 A1 | 11/2011 | Friedli |
| 2012/0022833 A1 | 1/2012 | Sasaki |
| 2013/0211323 A1* | 8/2013 | Lee .................... A61M 5/14228 604/67 |
| 2013/0253419 A1 | 9/2013 | Favreau |
| 2013/0253472 A1 | 9/2013 | Cabiri |
| 2013/0296784 A1 | 11/2013 | Tsoukalis |
| 2014/0079590 A1 | 3/2014 | Rossi et al. |
| 2014/0107579 A1 | 4/2014 | Lanigan et al. |

FOREIGN PATENT DOCUMENTS

| | | |
|---|---|---|
| EP | 1 965 325 A1 | 9/2008 |
| GB | 1081818 | 9/1967 |
| GB | 2487040 | 7/2012 |
| WO | WO 2007/092618 A2 | 8/2007 |
| WO | WO 200859494 | 5/2008 |
| WO | WO 2009/032399 A1 | 3/2009 |

OTHER PUBLICATIONS

U.S. Appl. No. 14/586,930, filed Dec. 30, 2014.
U.S. Appl. No. 14/586,930, Aug. 10, 2017 Non-Final Office Action.
U.S. Appl. No. 14/586,927, Aug. 9, 2017 Restriction Requirement.
Low Electromagnetic Emissions Office Equipment. "Electromagnetic emissions of USB hubs," Retrieved Aug. 3, 2017, from https://www.lowemfoffice.com/usb_hubs.htm.
The Editors of Encyclopaedia Britannica. "Printed circuit," Encyclopaedia Britannica. Sep. 6, 2013, https://www.britannica.com/technology/printed-circuit (Accessed on Aug. 7, 2017).
European Search Report dated Mar. 12, 2018 in Application No. EP 17203875.
U.S. Appl. No. 14/586,927, Jan. 16, 2018 Non-Final Office Action.
U.S. Appl. No. 14/586,930, Feb. 28, 2018 Non-Final Office Action.
Stack. (n.d.). Dictionary.com Unabridged. Retrieved Feb. 23, 2018 from Dictionary.com website http://www.dictionary.com/browse/stack.

* cited by examiner

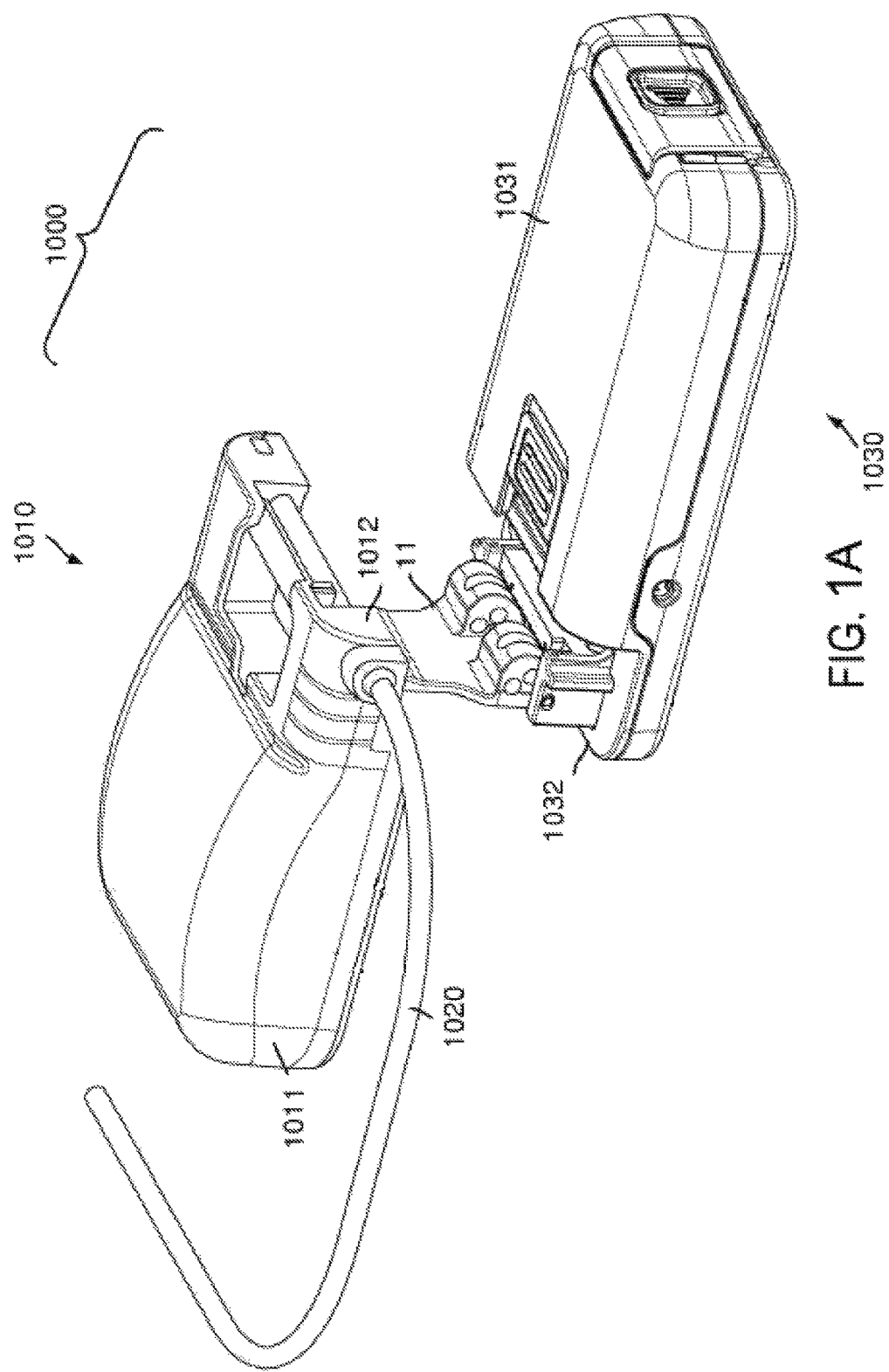

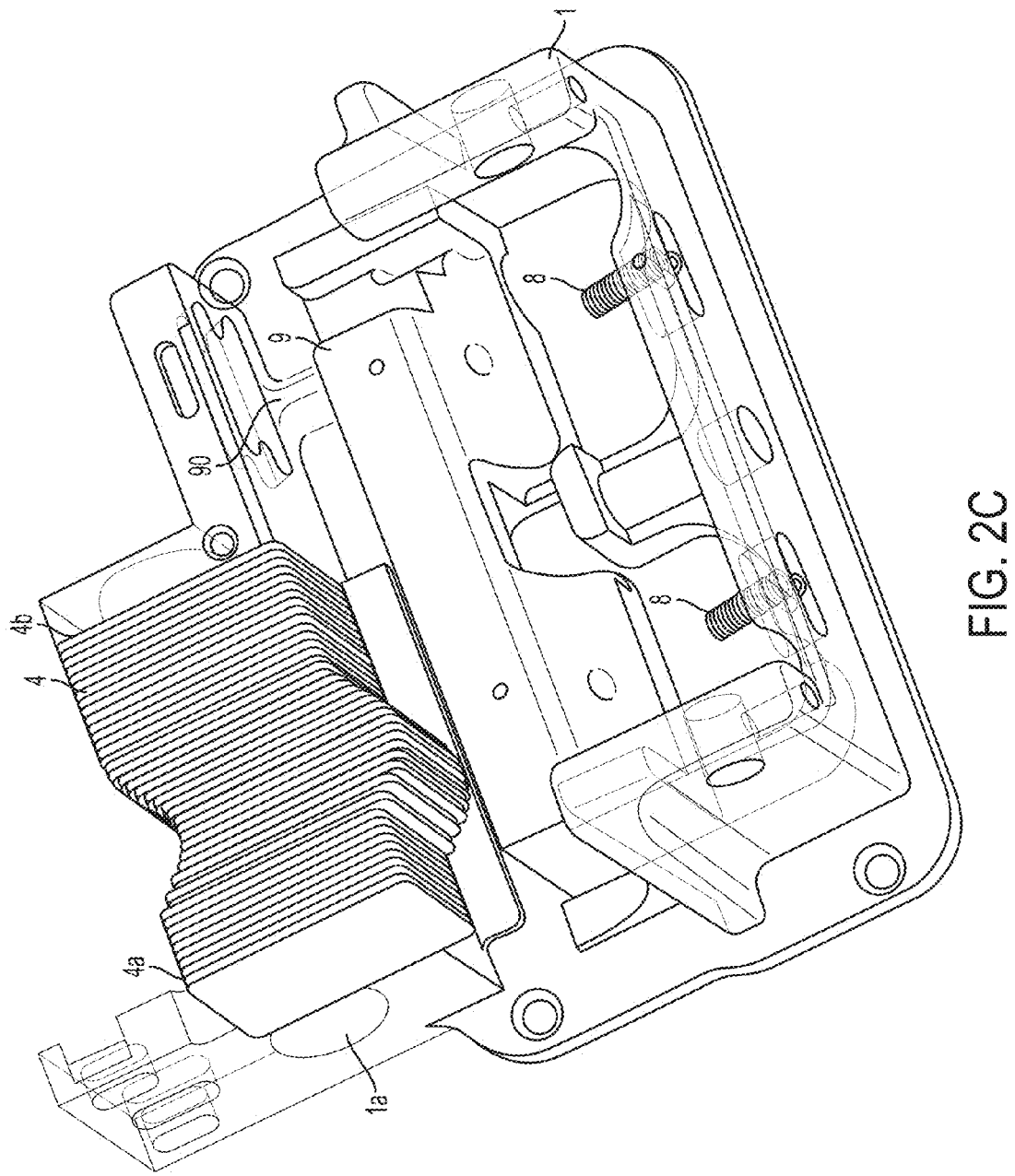

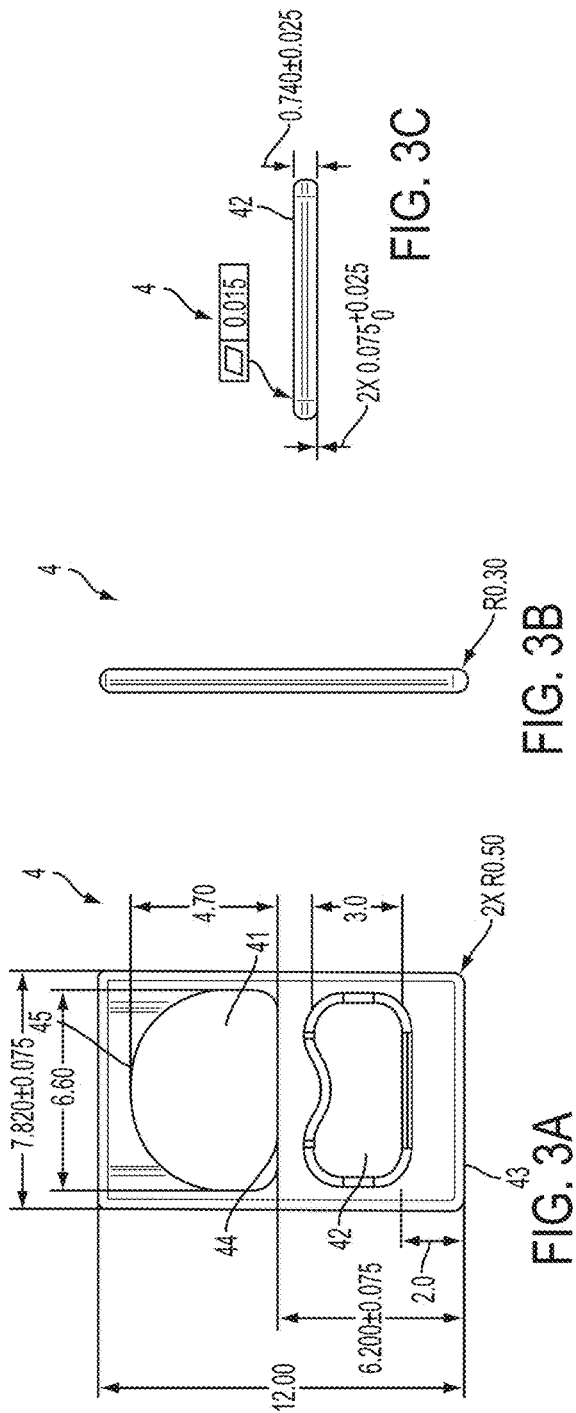
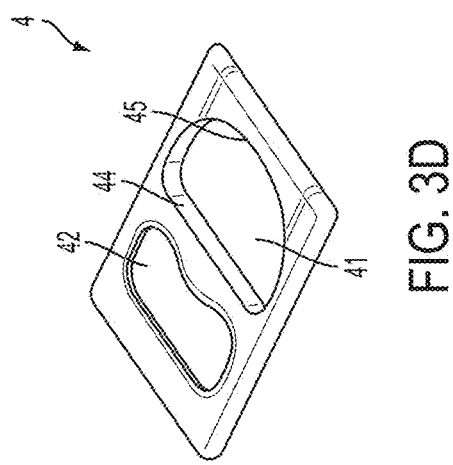
FIG. 3A  FIG. 3B  FIG. 3C  FIG. 3D

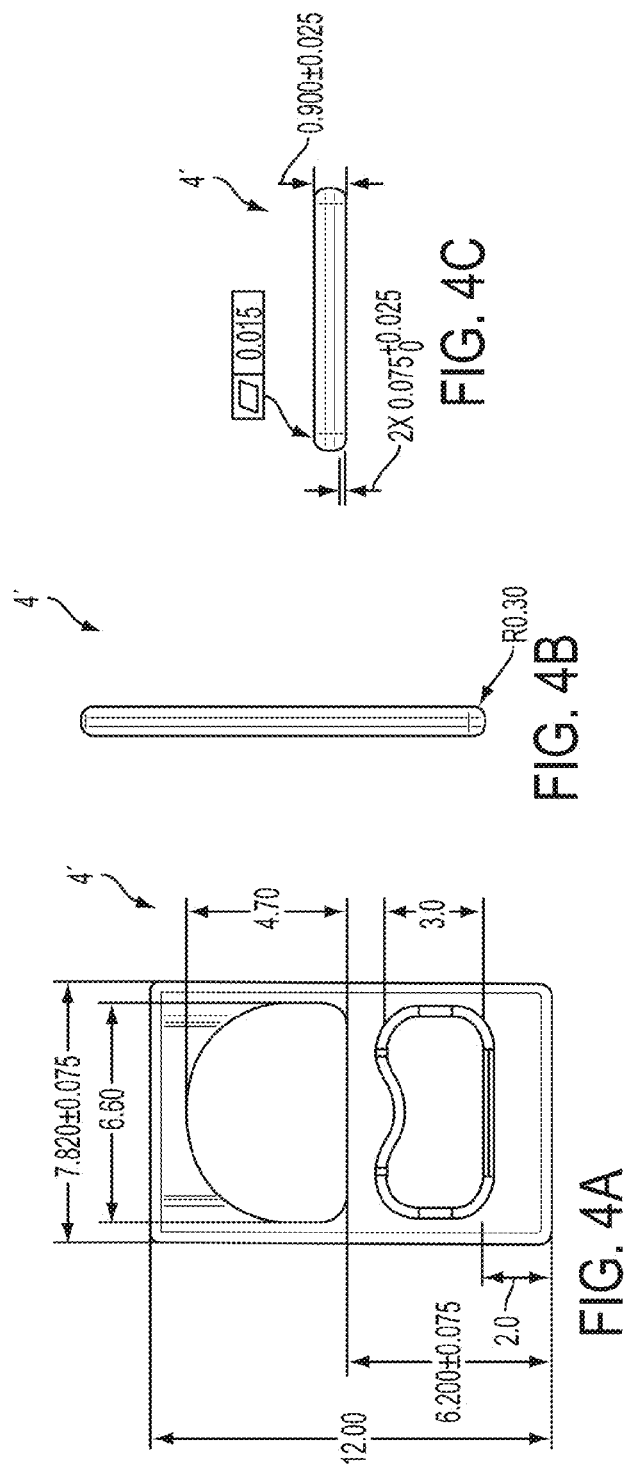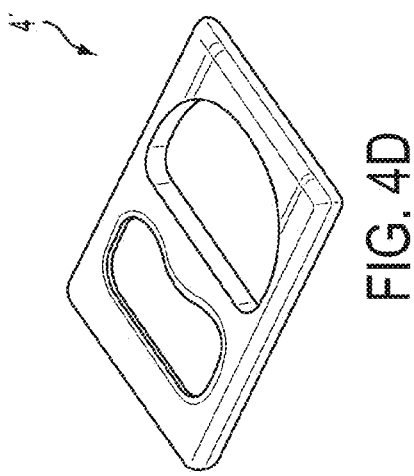

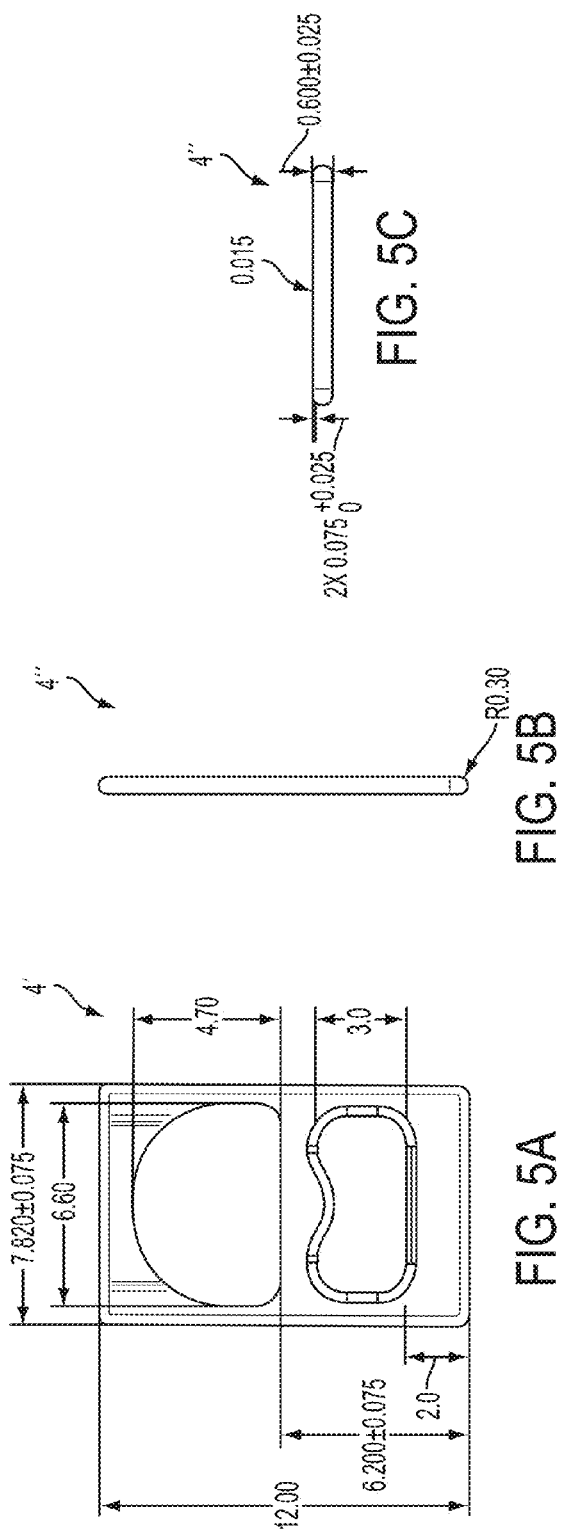

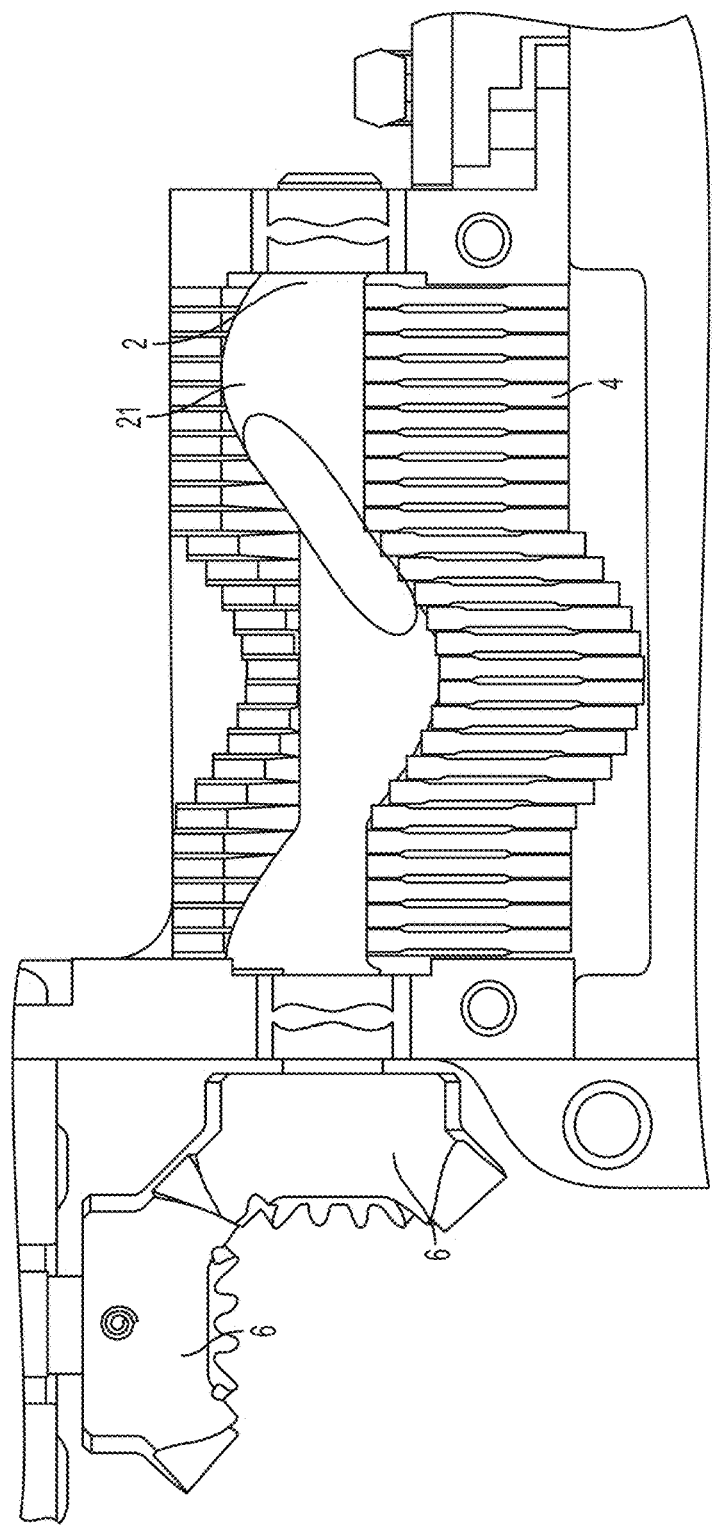

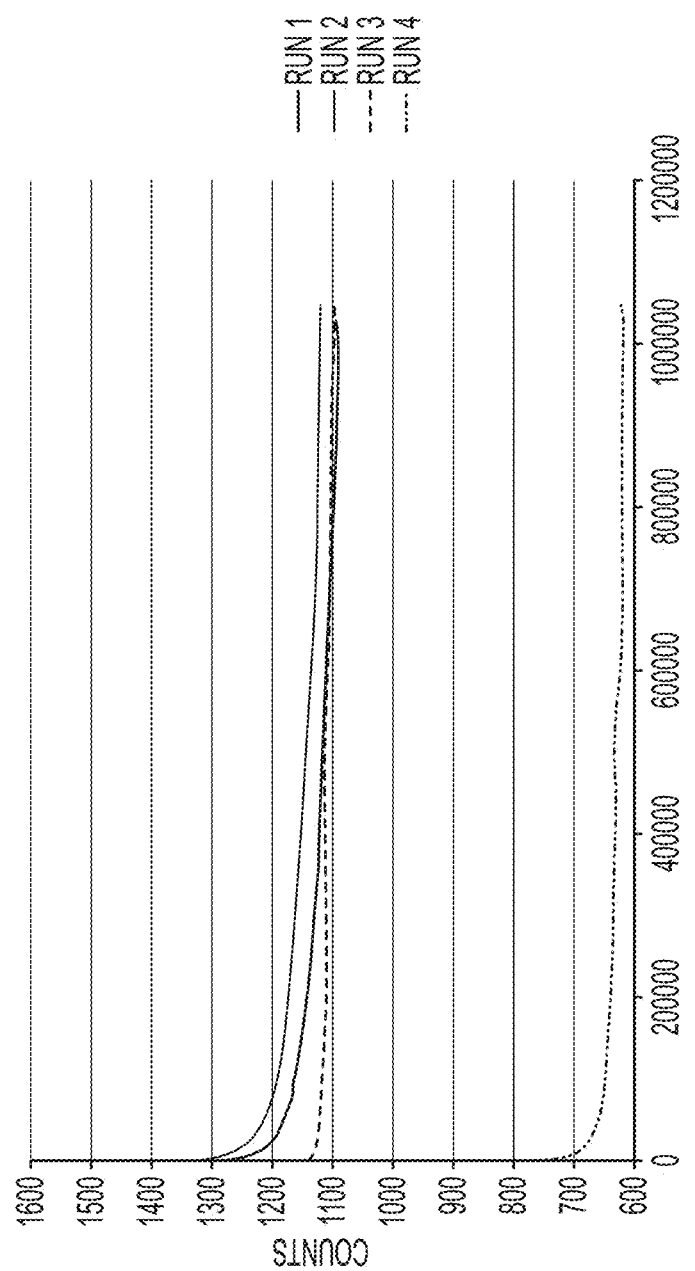

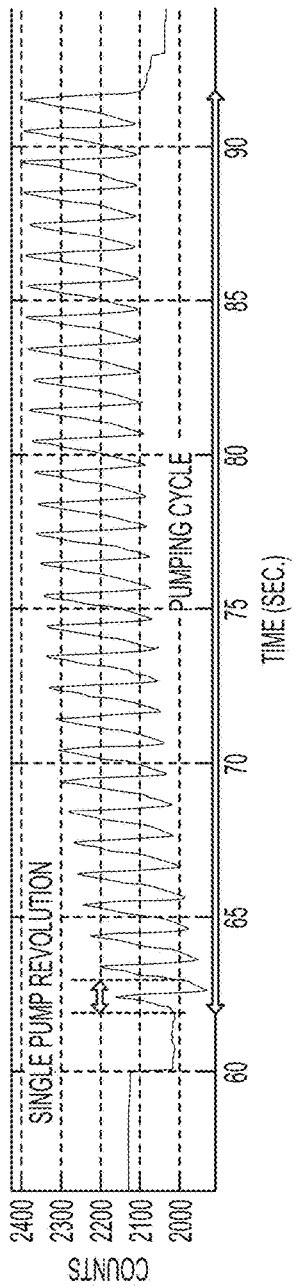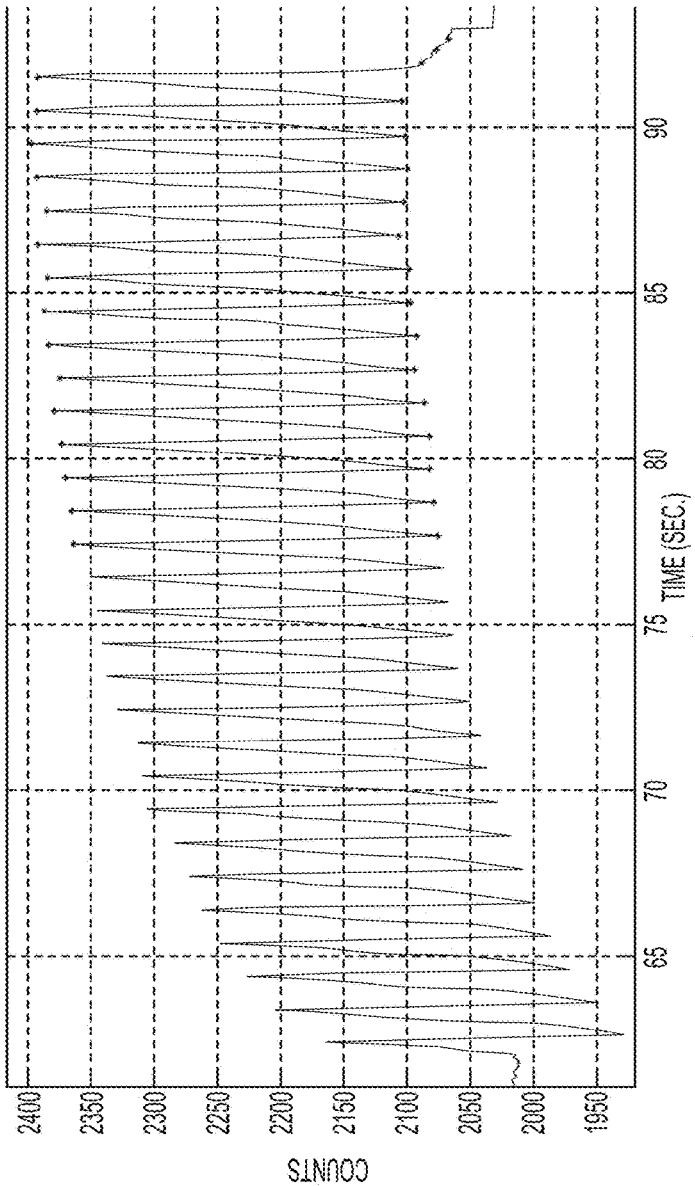

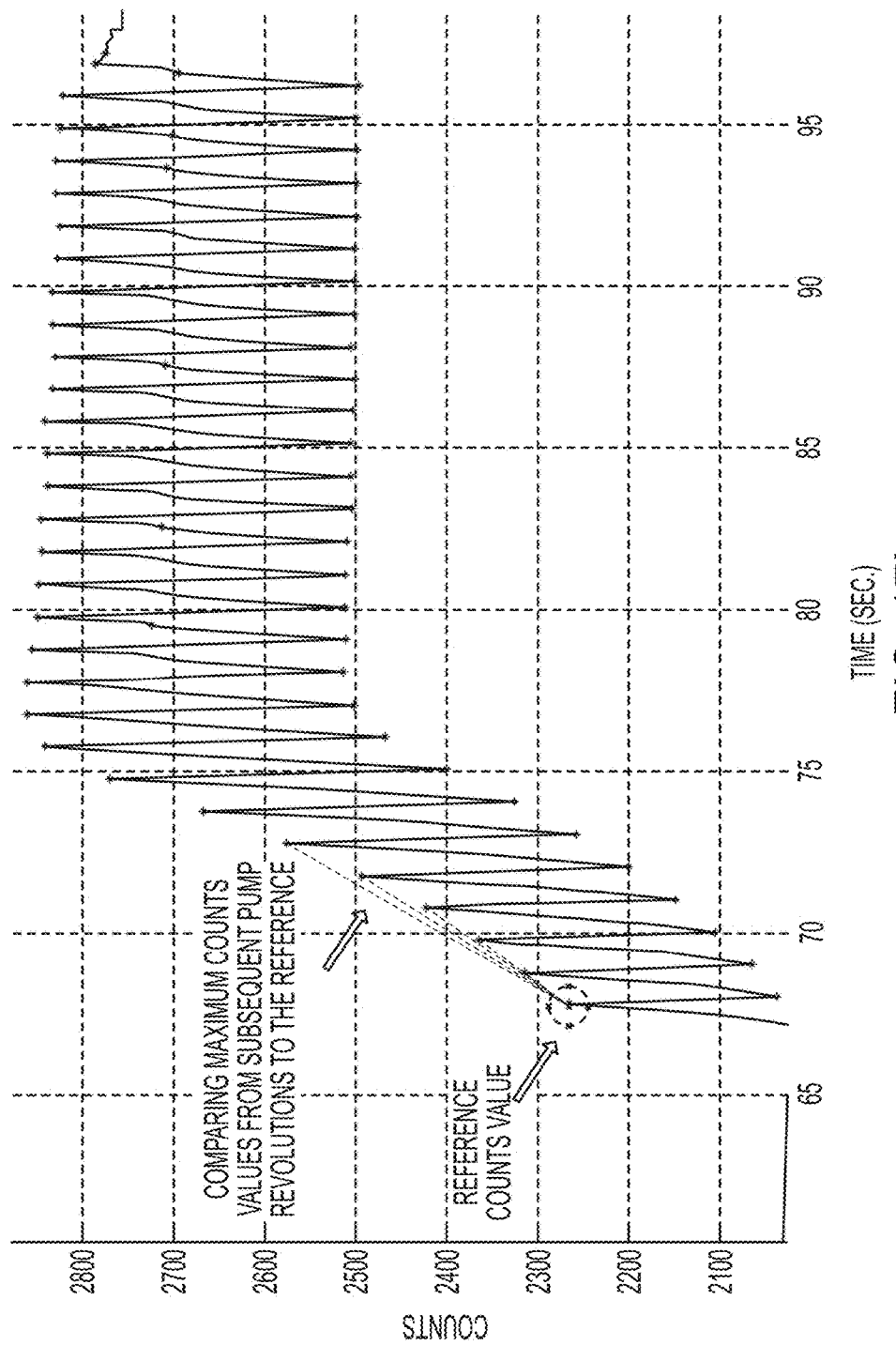

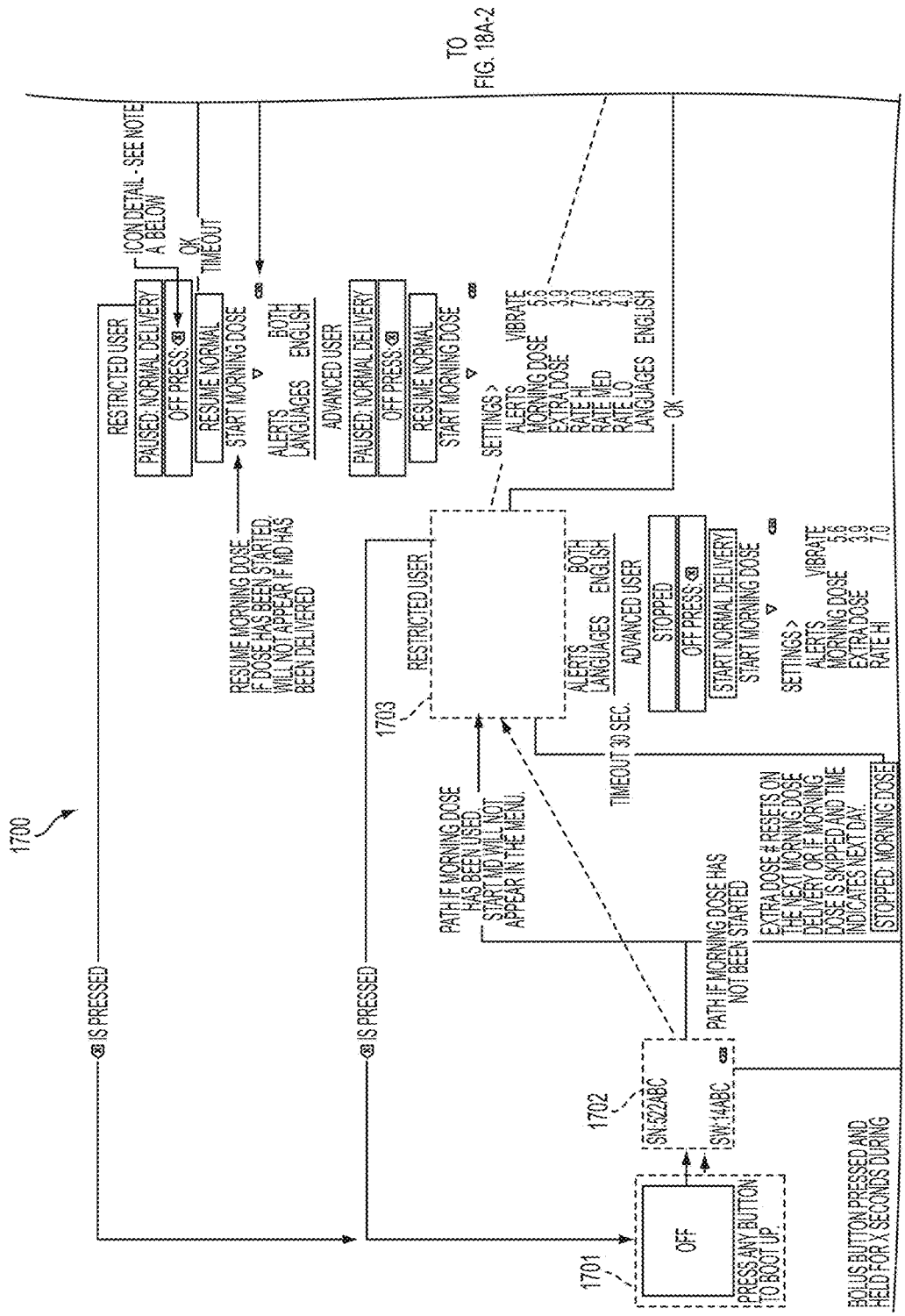

PUMP, MOTOR AND ASSEMBLY FOR BENEFICIAL AGENT DELIVERY

CROSS-REFERENCE TO RELATED APPLICATIONS

This application claims priority to U.S. Provisional Patent Application Nos. 61/922,709, filed Dec. 31, 2013; and 62/054,134, filed Sep. 23, 2014; each of which is incorporated by reference herein in its entirety.

BACKGROUND

Field of the Disclosed Subject Matter

The disclosed subject matter is generally related to devices, systems and methods for controlling and delivering fluids, for example for delivery of a beneficial agent to a user.

Description of Related Art

A variety of fluid transport devices and systems have been developed for controlling and delivering beneficial agents in fluid form. Such fluid flow systems can include 1) volumetric-based aspiration flow systems using positive displacement pumps, and 2) vacuum-based aspiration systems using a vacuum source. For example, volumetric aspiration systems include peristaltic pumps for the delivery of therapeutic agents to a user. Various forms of peristaltic pumps are known, such as using rotating rollers to press against a flexible tubing to induce flow therethrough. Cassette systems or other reservoir configurations can be coupled with the pump device to provide a source of beneficial agent fluid via the flexible tubing.

Such devices and systems are particularly beneficial as portable infusion pumps capable of being worn or carried by the user. However, there remains a need for improvement of such devices and systems. Such improvements include, among other things, improved energy consumption and battery life, improved pump efficiency and control, improved comfort and ergonomics, and improved cassette configuration for more complete access to the reservoir contents.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a peristaltic pump for delivery of a beneficial agent to a user. The pump includes a motor, a cam shaft coupled to the motor for rotation about a longitudinal axis of the cam shaft, the cam shaft having at least one radially-outward projection defining a helical engagement portion disposed along a length of the cam shaft, and a plurality of finger plates disposed along the length of the cam shaft, each finger plate mounted for movement in a transverse direction relative to the longitudinal axis of the cam shaft, each finger plate having an aperture defined therein to receive the cam shaft therethrough, each aperture having a substantially straight edge region and an opposing edge region. Engagement of the helical engagement portion with the substantially flat edge region during rotation of the cam shaft urges the finger plate transversely toward an extended position.

Additionally, and as embodied herein, the finger plate can be free of transverse movement as the helical engagement portion passes along at least a portion of the opposing edge region during rotation of the cam shaft. The opposing edge region can include an arcuate edge, and/or can include a gap. Each finger plate can have a recessed area in a surface proximate the aperture. The recessed area can be recessed 0.1 mm relative the surface of the finger plate. Each finger plate can include an end surface at an end facing the direction of the transverse movement. The recessed area can be disposed between the aperture and the end surface. Furthermore, the recessed area can be spaced from the end surface.

Additionally, and as embodied herein, with each finger plate having an end surface at an end facing the direction of the transverse movement, the end surfaces of the finger plates together can define a contiguous surface facing the direction of the transverse movement. Each finger plate can be unbiased, or each finger plate can be biased away from the extended position. The plurality of finger plates can be disposed parallel with each other and arranged for sequential movement toward the extended position.

In addition, and as embodied herein, the pump can further include a gap defined between an end plate of the plurality of finger plates and an interior wall of the peristaltic pump, wherein a filler plate can be disposed within the gap. The filler plate can have a different thickness than each of the plurality of finger plates. The different thickness can be less than each of the plurality of finger plates. Alternatively, the different thickness can be greater than each of the plurality of finger plates. The substantially straight edge region of the aperture likewise can have a thickness greater than the opposing edge region. Each finger plate can include a ceramic material. Additionally or alternatively, the camshaft can include a ceramic material.

Additionally, and as embodied herein, the pump can include one or more bevel gears coupling the motor to the cam shaft. The cam shaft can include a chamfered portion formed at a radial end of the helical engagement portion. The helical engagement portion can extend around the cam shaft greater than one revolution of the helical engagement portion.

Additionally, and as embodied herein, the pump can include a cassette including a cassette housing with a fluid reservoir defined therein and a delivery tube fluidly coupled with the fluid reservoir. The cassette housing can have a cassette base region, and the pump can include a receiving region to receive the cassette base region with, the plurality of finger plates disposed proximate the receiving region. Each finger plate thus can be configured to compress a portion the delivery tube in the extended position. When the cam shaft rotates out of engagement with the substantially straight edge region of each finger plate, the delivery tube can be configured to urge the finger plate away from the extended position. The plurality of finger plates can be disposed parallel with each other and arranged for sequential movement toward the extended position to sequentially compress the delivery tube to create a vacuum force to draw the beneficial agent from the fluid reservoir.

According to another aspect of the disclosed subject matter, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a fluid drive component disposed proximate the receiving region, a display to provide visual feedback to the user, a plurality of input buttons disposed on the pump housing, a first processor coupled to the fluid drive component and the display and configured to reduce power to or otherwise hibernate the fluid drive component and the display when the pump is in an inactive state, and a second processor coupled to the first processor and the plurality of input buttons. The second processor is configured to provide an activation signal to the first processor when one or more of the plurality of input buttons is deployed.

Additionally or alternatively, the pump assembly can further include a radio-frequency identification (RFID) transceiver coupled to the first processor, and the first processor can be is configured to reduce power to the RFID transceiver when the pump is in the inactive state. The pump assembly can further include an occlusion sensor coupled to the first processor, and the first processor can be configured to reduce power to the occlusion sensor when the pump is in the inactive state.

Furthermore, and as embodied herein, the pump assembly can further include a serial bus coupled to the first processor, and the first processor can be configured to reduce power to the serial bus when the pump is in the inactive state. The pump assembly can further include a power supply voltage monitor coupled to the second processor, and the second processor can be configured to maintain the power supply voltage monitor in an active state when the first processor is powered down. The pump assembly can further include one or more memories, a primary power supply and a backup power supply coupled to the second processor, and the second processor can be configured to utilize the backup power supply to save present data to the one or more memories when the second processor detects the primary power supply is removed or disabled.

In addition, and as embodied herein, the pump assembly can further include a battery coulomb counter coupled to the second processor, and the second processor can be configured to maintain the battery coulomb counter in an active state when the first processor is powered down. The pump assembly can further include a speaker, and the first processor and the second processor each can be coupled to the speaker and configured to send an audio signal to the speaker when a fault is detected.

According to another aspect of the disclosed subject matter, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a primary power source, a secondary power source coupled to the primary power source, a fluid drive component disposed proximate the receiving region and coupled to the primary power source isolated from the secondary power source, a first processor coupled to the primary power source and the secondary power source, a second processor coupled to the first processor, the primary power source and the secondary power source, one or more memories coupled to the first processor. At least one of the first processor and the second processor is configured, when the primary power source is removed or disabled, to utilize the secondary power source and the first processor to complete writing operations to the one or more memories prior to depletion of the secondary power source.

Additionally, and as embodied herein, the secondary power source can include a 1F capacitor. The secondary power source can be coupled to the primary power source via a secondary power source charger configured to charge the secondary power source when the primary power source is active. The one or more memories can include a nonvolatile memory storage.

Furthermore, and as embodied herein, the pump assembly can further include an RFID transceiver coupled to the secondary power source. The pump assembly can further include a speaker coupled to the secondary power source. The first processor and the second processor each can be coupled to the speaker, directly or via an audio amplifier, and configured to send an audio signal to the speaker when a fault is detected. The pump assembly can further include a display to provide visual feedback to the user. The display can be coupled to the primary power source and isolated from or otherwise not connected to the secondary power source. The pump assembly can further include an occlusion sensor coupled to the primary power source and isolated from the secondary power source.

According to another aspect of the disclosed subject matter, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a fluid drive component disposed proximate the receiving region, a main controller circuit board coupled to and configured to control the fluid drive component, and at least one secondary circuit board foldably joined to the main controller circuit board through a flexible substrate and disposed within the interior in a stacked relationship relative the main controller circuit board. A plurality of such secondary circuit boards can be provided, each joined to the main controller circuit board by a flexible substrate either directly or indirectly.

For example, and as embodied herein, the at least one secondary circuit board can include a power source controller board coupled to a power source. The at least one secondary circuit board can include an occlusion sensor controller board coupled to an occlusion sensor. The at least one secondary circuit board can include a serial bus controller board. The serial bus controller board can include an electromagnetic compatibility component. The serial bus controller board can include a serial bus port disposed proximate an exterior wall of the pump housing and aligned with an aperture in the exterior wall.

Furthermore, and as embodied herein, the at least one secondary circuit board can include a motor signal encoder coupled to the fluid drive component. The fluid drive component can be coupled to the motor signal encoder in a stacked relationship with the main controller circuit board. The at least one secondary circuit board can include a speaker, alone or with an audio amplifier. The at least one secondary circuit board can include a haptic actuator.

In addition, and as embodied herein, the at least one secondary circuit board can include a display controller coupled to a display. The display can further include a liquid crystal display (LCD). The display can further include a flexible light transmission component in optical communication with the LCD. The at least one secondary circuit board can include an input controller. The input controller board can include a plurality of input buttons disposed proximate an exterior wall of the pump housing and aligned with corresponding apertures in the exterior wall. The pump housing can have an interior having a height within a range of 18.5 mm to 20 mm. The flexible substrate can include polyimide, copper-clad polyimide, polyether ether ketone, transparent conductive polyester film, or a combination thereof. The flexible substrate can have a thickness within a range of 95 μm to 192.5 μm.

According to another aspect of the disclosed subject matter, a device for delivery of a beneficial agent to a user generally includes a cassette, a delivery tube, a pump and a contact force sensor. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component, the pump housing having a receiving region to receive the cassette base region, the fluid drive component disposed proximate the receiving region. The contact force sensor is in communication, such as by direct or indirect contact, with the delivery tube and arranged to measure a force or pressure in the delivery tube. The device includes one or more processors in communication with the contact force sensor to receive data representing the measured force or pressure from the contact force sensor, the one or more processors configured to determine a maximum force value detected by the contact force sensor during an initial pumping cycle, the maximum force value corresponding to a baseline maximum force value, obtain subsequent force values from the contact force sensor during each subsequent pumping cycle, and determine an occlusion is present if one or more of the subsequent force values exceed the baseline maximum force value by a threshold amount.

Additionally, and as embodied herein, the one or more processors can be further configured to determine a subsequent maximum force value during the subsequent pumping cycle, and adjust the baseline maximum force value to the subsequent maximum force value if the subsequent maximum force value is less than the baseline maximum force value. The threshold amount can be about 10% of the baseline maximum force value.

Furthermore, and as embodied herein, the one or more processors can be further configured to determine a local maximum force value during an initial pump revolution of each pump cycle, the local maximum force corresponding to a baseline local maximum force value, obtain a subsequent local force maximum during each subsequent pump revolution of each pump cycle, and determine an occlusion is present if one or more of the subsequent local force maxima exceeds the baseline local maximum force value by a local threshold amount. The local threshold amount can be about 13% of the baseline local maximum force value. The one or more processors can be further configured to determine the local maximum force value of each pump cycle when a flow rate of the fluid drive component is above a threshold flow rate. The threshold flow rate can be 10 mL/hr.

Furthermore, and as embodied herein, the one or more processors can be further configured to determine a local minimum force value detected by the contact force sensor during each revolution of each pumping cycle, and determine an error is present if the local minimum force value does not exceed the local maximum force value of a corresponding pump cycle by a local minimum threshold amount. The error can include a mechanical failure of the fluid drive component. The error can include an occlusion signal circuitry failure. A duration of each pumping cycle can be determined at least in part by a flow rate of the fluid drive component.

In addition, and as embodied herein, the device can further include a motor operatively coupled to the fluid drive component, and a rotational position sensor operatively coupled to the motor to determine a rotational position of the motor. The one or more processors can be further operatively coupled to the rotational position sensor, and the one or more processors can be further configured to determine each pump revolution from the rotational position sensor. The one or more processors can be further configured to stop the fluid drive component when the occlusion is determined to be present. The device can further include a display operatively coupled to the one or more processors, and the one or more processors can be further configured to display an error signal on the display when the occlusion is determined to be present. The contact force sensor can include a single contact force sensor. The one or more processors can be further configured to apply a four-sample moving average filter to the data representing the measured force or pressure from the contact force sensor.

According to another aspect of the disclosed subject matter, and further to the above, a device for delivery of a beneficial agent to a user generally includes a cassette, a delivery tube, a pump, a lock member, and a contact force sensor. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component, the pump housing having a receiving region to receive the cassette base region, the fluid drive component disposed proximate the receiving region. The lock member is coupled to the pump housing and movable between an open position and a closed position, the cassette capable of being inserted into and removed from the receiving region when the lock member is in the open position, and the cassette being secured to the pump with the cassette base region within the receiving region and a length of the delivery tube in operative engagement with the fluid drive component when the lock member is in the closed position. The lock member includes a proximity tag configured to be disposed proximate the proximity sensor when the lock member is in the closed position. The contact force sensor is in communication with the delivery tube and arranged to measure a force or pressure in the delivery tube. The device further includes one or more processors in communication with the proximity sensor and the contact force sensor to receive a proximity signal and contact force data, respectively, therefrom, the one or more processors configured to determine whether the lock member is in the closed position using the proximity signal, determine whether the delivery tube is in operative engagement with the fluid drive component using the contact force data; and enable operation of the fluid drive component if the lock member is determined to be in the closed position and the delivery tube is determined to be in operative engagement with the fluid drive component.

Additionally, and as embodied herein, the proximity sensor can include a reed switch. The proximity tag can include a magnet. The one or more processors can be further configured to compare the contact force data to a threshold value, and determine the delivery tube is in operative engagement with the fluid drive component if the contact force data exceeds the threshold value. The one or more processors can be further configured to determine a local minimum force value detected by the contact force sensor during each revolution of each pumping cycle, and determine the delivery tube is in operative engagement with the fluid drive component if the local minimum force value exceeds the local maximum force value of a corresponding pump cycle by a local minimum threshold amount.

Furthermore, and as embodied herein, a cassette base region can include a RFID tag. The receiving region can include a RFID reader configured to read the RFID tag when the cassette is secured to the pump. The one or more processors can be further configured to receive identification information for the cassette encoded on the RFID tag from the RFID reader, determine whether the identification information is valid, and enable operation of the fluid drive component if the identification information is valid. The RFID tag can further include an expiration date of the beneficial agent, and the one or more processors can be further configured to receive the expiration date of the beneficial agent from the RFID reader, determine whether the expiration date is exceeded, and enable operation of the fluid drive component if the expiration date is not exceeded. The RFID tag can include high or ultra-high radio frequency ID.

According to another aspect of the disclosed subject matter, a device for delivery of a beneficial agent to a user generally includes a cassette, a delivery tube, a pump, a lock member, and a contact force sensor. The cassette includes a cassette housing with a fluid reservoir defined therein. The cassette housing has a cassette base region including a RFID tag. The delivery tube is fluidly coupled with the fluid reservoir. The pump includes a pump housing containing a pump assembly having a fluid drive component, a proximity sensor and a RFID reader, the pump housing having a receiving region to receive the cassette base region, the fluid drive component, proximity sensor and RFID reader disposed proximate the receiving region. The lock member is coupled to the pump housing and movable between an open position and a closed position, the cassette capable of being inserted into and removed from the receiving region when the lock member is in the open position, and the cassette being secured to the pump with the cassette base region within the receiving region and a length of the delivery tube in operative engagement with the fluid drive component when the lock member is in the closed position. The lock member includes a proximity tag configured to be disposed proximate the proximity sensor when the lock member is in the closed position. The contact force sensor is in communication with the delivery tube and arranged to measure a force or pressure in the delivery tube. The device further includes one or more processors in communication with the proximity sensor, the contact force sensor and the RFID reader to receive a proximity signal, contact force data and identification information for the cassette encoded on the RFID tag, respectively, therefrom, the one or more processors configured to determine whether the lock member is in the closed position using the proximity signal, determine whether the delivery tube is in operative engagement with the fluid drive component using the contact force data, determine whether the identification information is valid, and enable operation of the fluid drive component if the lock member is determined to be in the closed position, the delivery tube is determined to be in operative engagement with the fluid drive component, and the identification information is determined to be valid.

Furthermore, and as embodied herein, the one or more processors can be further configured to receive identification information for the cassette encoded on the RFID tag from the RFID reader, determine whether the identification information is valid, and enable operation of the fluid drive component if the identification information is valid. The RFID tag can further include an expiration date of the beneficial agent, and the one or more processors can be further configured to receive the expiration date of the beneficial agent from the RFID reader, determine whether the expiration date is exceeded, and enable operation of the fluid drive component if the expiration date is not exceeded. The RFID tag can include high or ultra-high radio frequency ID.

For each of the aspects described above, the device and/or cassette can include a beneficial agent contained in the fluid reservoir. The beneficial agent can include one or more of levodopa and carbidopa. Furthermore, the various aspects above can be combined to provide a device, pump and/or cassette with selected features and combinations of features as desired.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIG. 1A is an exploded perspective view of an exemplary device for delivering a beneficial agent according to the disclosed subject matter.

FIG. 2C is a perspective view of exemplary finger plates joined to the base block of FIG. 2B.

FIG. 3A is a front view of an exemplary embodiment of a finger plate for use with the pump assembly of FIG. 1B, the rear view being substantially similar.

FIG. 3B is a left side view of the finger plate of FIG. 3A, the right side view being substantially similar.

FIG. 3C is a bottom view of the finger plate of FIG. 3A.

FIG. 3D is a top right perspective view of the finger plate of FIG. 3A.

FIG. 4A is a front view of an alternative embodiment of a finger plate for use with the pump assembly of FIG. 1B, the rear view being substantially similar.

FIG. 4B is a left side view of the finger plate of FIG. 4A, the right side view being substantially similar.

FIG. 4C is a bottom view of the finger plate of FIG. 4A.

FIG. 4D is a top right perspective view of the finger plate of FIG. 4A.

FIG. 5A is a front view of another alternative embodiment of a finger plate for use with the pump assembly of FIG. 1B, the rear view being substantially similar.

FIG. 5B is a left side view of the finger plate of FIG. 5A, the right side view being substantially similar.

FIG. 5C is a bottom view of the finger plate of FIG. 5A.

FIG. 5D is a top right perspective view of the finger plate of FIG. 5A.

FIG. 6F is a right side view of the exemplary bevel gear of FIG. 6E, the left side view being substantially similar.

FIG. 8C is a partial cross-sectional view taken parallel to a longitudinal axis of the exemplary cam shaft and through a portion of the projection of the cam shaft, illustrating the portion of the projection interacting with exemplary finger plates of the pump assembly of FIG. 1B

FIGS. 17A-17M are diagrams illustrating exemplary techniques for occlusion detection and/or fault detection for a beneficial agent delivery device according to the disclosed subject matter.

FIGS. 18A-1 to 18A-4 together are a schematic diagram illustrating exemplary techniques for providing a graphical user interface for a beneficial agent delivery device according to the disclosed subject matter.

FIGS. 18C-1 and 18-C-2 together are a schematic diagram illustrating an exemplary technique for providing a graphical user interface for a beneficial agent delivery device according to the disclosed subject matter.

FIGS. 18D-1 to 18D-4 together are a schematic diagram illustrating exemplary techniques for providing a graphical user interface for a beneficial agent delivery device according to the disclosed subject matter.

DESCRIPTION

Figure 1B:
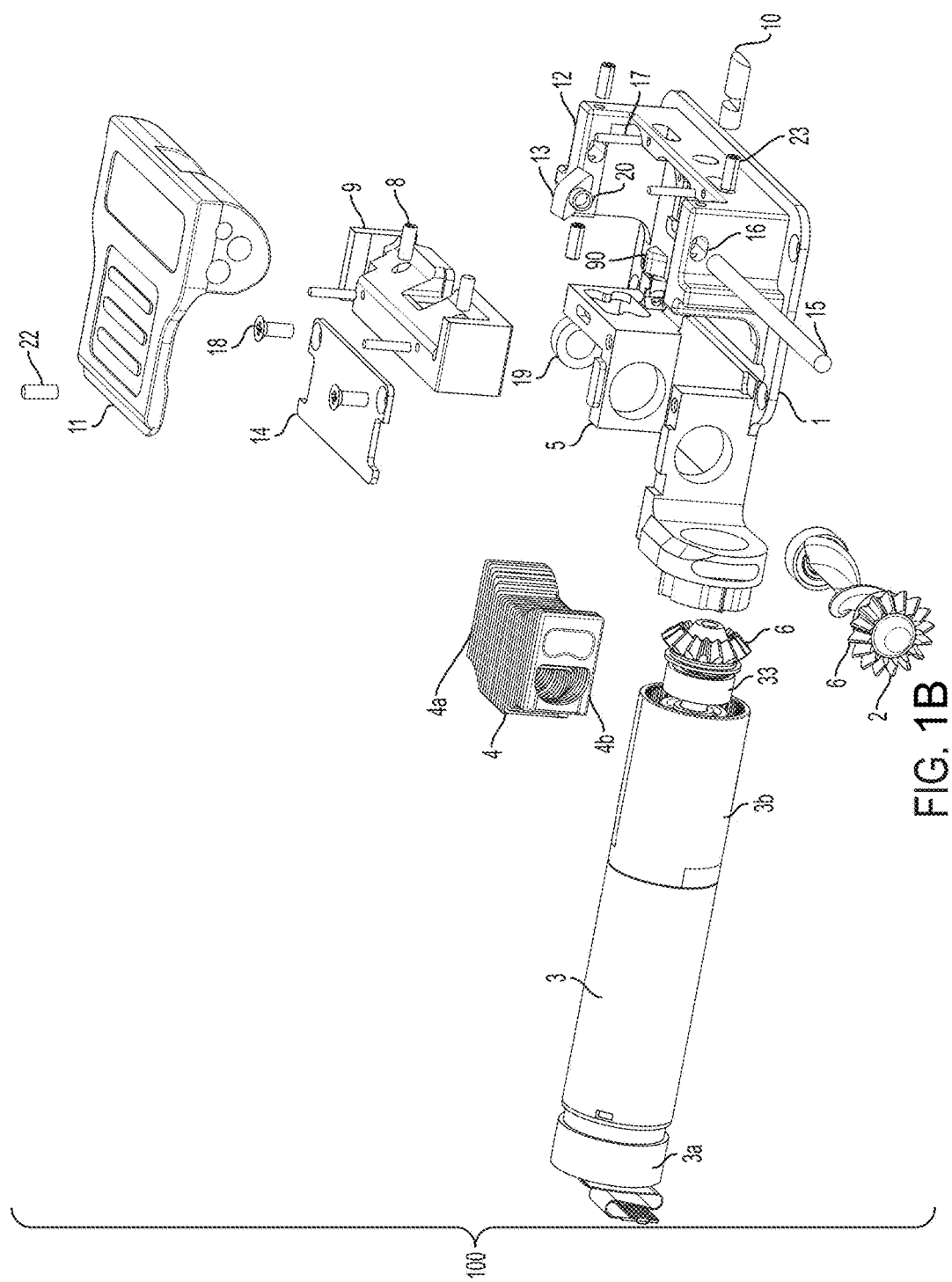
FIG. 1B is an exploded schematic view of an exemplary embodiment of a pump assembly according to the disclosed subject matter.

Reference will now be made in detail to the various exemplary embodiments of the disclosed subject matter, exemplary embodiments of which are illustrated in the accompanying drawings. The structure and corresponding method of operation of and method of using the disclosed subject matter will be described in conjunction with the detailed description of the system.

The apparatus and methods presented herein can be used for administering any of a variety of suitable therapeutic agents or substances, such as a drug or biologic agent, to a patient. For example, and as embodied herein, the device can include a pump joined to a cassette, which can include a fluid reservoir containing a fluid substance and can be joined to a delivery tube system. In operation, the pump can operate on the cassette to deliver the fluid substance through the tubing system. In this manner, the device is capable of administering a dosage of the fluid substance, such as a therapeutic agent, including a formulation in a liquid or gel form, through the delivery tube system and to a patient. In some embodiments, the fluid therapeutic agent can include one or more pharmaceutical or biologic agents. For example and without limitation, one such fluid therapeutic agent can be a central nervous system agent, such as levodopa. The central nervous system agent can be administered alone or in combination with, for example and without limitation, a decarboxylase inhibitor, such as carbidopa.

In accordance with one aspect of the disclosed subject matter, a peristaltic pump for delivery of a beneficial agent to a user includes a motor, a cam shaft coupled to the motor for rotation about a longitudinal axis of the cam shaft, the cam shaft having at least one radially-outward projection defining a helical engagement portion disposed along a length of the cam shaft, and a plurality of finger plates disposed along the length of the cam shaft, each finger plate mounted for movement in a transverse direction relative to the longitudinal axis of the cam shaft, each finger plate having an aperture defined therein to receive the cam shaft therethrough, each aperture having a substantially straight edge region and an opposing edge region. Engagement of the helical engagement portion with the substantially flat edge region during rotation of the cam shaft urges the finger plate transversely toward an extended position.

Additionally, and as embodied herein, the finger plate can be free of transverse movement as the helical engagement portion passes along at least a portion of the opposing edge region during rotation of the cam shaft. The opposing edge region can include an arcuate edge, and/or can include a gap. Each finger plate can have a recessed area in a surface proximate the aperture. The recessed area can be recessed 0.1 mm relative the surface of the finger plate. Each finger plate can include an end surface at an end facing the direction of the transverse movement. The recessed area can be disposed between the aperture and the end surface. Furthermore, the recessed area can be spaced from the end surface.

Additionally, and as embodied herein, with each finger plate having an end surface at an end facing the direction of the transverse movement, the end surfaces of the finger plates together can define a contiguous surface facing the direction of the transverse movement. Each finger plate can be unbiased, or each finger plate can be biased away from the extended position. The plurality of finger plates can be disposed parallel with each other and arranged for sequential movement toward the extended position.

In addition, and as embodied herein, the pump can further include a gap defined between an end plate of the plurality of finger plates and an interior wall of the peristaltic pump, wherein a filler plate can be disposed within the gap. The filler plate can have a different thickness than each of the plurality of finger plates. The different thickness can be less than each of the plurality of finger plates. Alternatively, the different thickness can be greater than each of the plurality of finger plates. The substantially straight edge region of the aperture likewise can have a thickness greater than the opposing edge region. Each finger plate can include a ceramic material. Additionally or alternatively, the camshaft can include a ceramic material.

Additionally, and as embodied herein, the pump can include one or more bevel gears coupling the motor to the cam shaft. The cam shaft can include a chamfered portion formed at a radial end of the helical engagement portion. The helical engagement portion can extend around the cam shaft greater than one revolution of the helical engagement portion.

Additionally, and as embodied herein, the pump can include a cassette including a cassette housing with a fluid reservoir defined therein and a delivery tube fluidly coupled with the fluid reservoir. The cassette housing can have a cassette base region, and the pump can include a receiving region to receive the cassette base region with, the plurality of finger plates disposed proximate the receiving region. Each finger plate thus can be configured to compress a portion the delivery tube in the extended position. When the cam shaft rotates out of engagement with the substantially straight edge region of each finger plate, the delivery tube can be configured to urge the finger plate away from the extended position. The plurality of finger plates can be disposed parallel with each other and arranged for sequential movement toward the extended position to sequentially compress the delivery tube to create a vacuum force to draw the beneficial agent from the fluid reservoir.

Furthermore, and as embodied herein, the pump can further include a beneficial agent contained in the fluid reservoir. The beneficial agent can include one or more of levodopa and carbidopa.

The accompanying figures, where like reference numerals refer to identical or functionally similar elements throughout the separate views, serve to further illustrate various embodiments and to explain various principles and advantages all in accordance with the disclosed subject matter. For purpose of explanation and illustration, and not limitation, exemplary embodiments of the pump assembly of the disclosed subject matter and components thereof are shown in the accompanying FIGS. 1-8C. Furthermore, FIGS. 9 to 18D-4 each depicts techniques and corresponding systems for delivery of a beneficial agent to a user. Additionally, for example and without limitation, further details of exemplary cassettes and lock members for use with the pump assembly for delivery of a beneficial agent to a user, as discussed further below, are described in concurrently filed applications by Applicant, each entitled "DEVICES AND METHODS FOR DELIVERING A BENEFICIAL AGENT TO A USER," Ser. Nos. 14/586,916 and 14/586,912, each of which is incorporated by reference in its entirety.

While the disclosed subject matter is described with respect to a delivery device to administer a dose of therapeutic agent, one skilled in the art will recognize that the disclosed subject matter is not limited to the illustrative embodiment, and that the devices disclosed herein can be configured for delivering any suitable substance therethrough. In addition, the components and the method of using the delivery device are not limited to the illustrative embodiments described or depicted herein. For example, the delivery device embodied herein can be used with other tubing assemblies and components thereof for similar benefits and advantages, and are not limited for use with the delivery tubing herein.

Referring to an illustrative embodiment of FIG. 1A, a delivery device 1000 includes a cassette 1010 and a pump 1030. Cassette 1010 includes a cassette housing 1011 with a fluid reservoir defined therein and a cassette base region 1012. A delivery tube 1020 is fluidly coupled with the fluid reservoir. Pump 1030 or pump device can include a pump housing 1031 with a pump assembly 100 disposed therein. Pump housing 1031 can include a receiving region 1032 configured to receive cassette base region 1012. As described further below, pump assembly 100 includes a lock member 11 coupled to pump housing 1031 and movable between an open position and a closed position. Cassette 1010 is capable of being inserted into and removed from the receiving region 1032 when the lock member 11 is in the open position, and the cassette 1010 is secured to the pump 1030 with the cassette base region 1012 within the receiving region 1032 and a length of the delivery tube 1020 in operative engagement with the pump 1030 when the lock member 11 is in the closed position.

Referring to an illustrative embodiment of FIG. 1B, pump assembly 100 can include a pump mechanism base block 1 and a cam shaft 2 joined thereto. A motor assembly 3 can be joined to the cam shaft 2, for example and as embodied herein, using bevel gears 6 disposed at a 90 degree angle from each other to transmit rotational force from the motor assembly 3 to the cam shaft 2. A plurality of finger plates 4 can be disposed along the longitudinal axis of the cam shaft 2. As embodied herein, each of the finger plates 4 can have the same dimensions. Additionally or alternatively, finger plates can be included that have different dimensions than other finger plates. For example and not limitation, finger plate 4a can have a thickness less than the thickness of the finger plates 4, and/or finger plate 4b can have a thickness greater than the thickness of the finger plates 4. For purpose of illustration and not limitation, as embodied herein, finger plate 4a can have a thickness of 0.60 mm, finger plates 4 can have a thickness of 0.74 mm, and finger plate 4b can have a thickness of 0.90 mm. For purpose of illustration and not limitation, and as embodied herein, the tolerance of the finger thickness can be +/−0.025 mm.

With reference to FIG. 1B, base block 1 can be provided to mount an occlusion sensor on the base block 1, as discussed further herein. For example and not limitation, such mounting can reduce the space occupied by the occlusion sensor and improve its accuracy compared to mounting the occlusion sensor on the pump housing. As embodied herein, motor 3 can be cylindrical. For example and not limitation, the motor 3 can have a length-to-width ratio of about 3.5:1 or greater, and as embodied herein can have a length-to-width ratio of about 5.1:1. Furthermore, and as embodied herein, motor 3 can be a coreless DC motor.

For purpose of illustration and not limitation, base block 1 can be formed by any suitable material (e.g., plastic, composites, metal, etc.), such as by machining, molding or the like. For example and not limitation, the material can be a metal such as 6061-T6 aluminum alloy. Additionally or alternatively, the base block 1 can include a finish, such as hard anodized per MIL-A-8625, TYPE III, class 2. The finish can be any desired or suitable color (e.g. black), and can have any suitable thickness, for example a thickness of at least 0.015 mm. Anodization can be applied selectively to pump components, such as base block 1, including for example pump components in electrical communication to provide suitable equipment grounding. For purpose of illustration and not limitation, a label including a part number can be included, for example, on the bottom side of the base block 1.

As embodied herein, an occlusion block 9 can be provided. Extension springs 8 can be secured to occlusion block 9, for example by inserting each spring 8 through clearance holes in occlusion block 9, inserting spring retention pins (not shown) through the holes and urging the pins into the occlusion block 9. The assembled occlusion block 9 can be inserted into the pump mechanism base block 1.

Additionally, a lock member 11 can be assembled onto the pump base 1. For example, a rear pin 10 can be inserted into the pump base 1 to secure a pin driver 13, which can be configured with an upward-facing notch. The lock member 11, pin driver 13 and torsion springs 12, 20 can be aligned and a latch hinge pin 15 can be inserted into lock member 11 and through the pin driver 13 and torsion springs 12, 20. One or more set screws 23 can be inserted into pump base 1 to adjust the occlusion block 9 position, as discussed herein. Spring retainer pins 17 can be inserted into pump mechanism base 1, and a free end of extension springs 8 can be urged over spring the retainer pins 17, which can be press fit into pump mechanism base 1 to secure the extension springs 8.

For example and not limitation, the occlusion block 9 can be moved into place by the lock member 11. The occlusion block 9 can be positioned to correspond to a desired occlusion percentage, for example within a range of 20% to 30% occlusion. Occlusion percentage O can be calculated based on the tubing wall thickness W and the occlusion distance D (e.g. the distance between the occlusion block 9 and the finger plates 4) using the equation $O=100\%*(1-(D/(2*W)))$. For purpose of illustration and not limitation, 100% occlusion can occur when D=0, which can correspond to the finger plates 4 in engagement with the occlusion block 9, that is without any space for a tube therebetween. Similarly, 0% occlusion can occur when D=2*W, which can correspond to the tubing being compressed by the finger plates 4 and occlusion block 9 such that inner walls of the tubing are proximate to or engaging each other. Accordingly, a 25% occlusion can correspond to the thickness of the walls of the tubing being compressed by 25% by the finger plates 4 and occlusion bock 9. Occlusion percentage can refer to the peak occlusion caused by the finger plates 4 during the overall stroke of the finger plates 4. Suitable occlusion, which can be within a range of about 24% to about 29%, and as embodied herein at about 27.5%, can prevent backflow and increase repeatability. Additionally, the lock member 11 configured to move the occlusion block 9 into place can affect the occlusion percentage tolerance, as discussed further herein.

For purpose of illustration and not limitation, an alignment pin 10 can be included and configured to move with the lock member 11 to insert into a drug cartridge brought into alignment with the pump and secured with the lock member 11. Insertion of the alignment pin 10 into the cartridge can reduce rocking of the drug cartridge and ensure proper alignment of the cartridge with the pump. Additionally or alternatively, the base block 1 can be adjusted to support greater pin stroke. For purpose of illustration and not limitation, mounting for torsion springs 12, 20 can be mounted to or integral with the base block 1.

A plurality of finger plates 4 can be placed in the cavity of the pump mechanism base block 1, as discussed herein. A gap can be defined between an end finger plate 4 and the inside wall of the base block 1, and as such, a non-standard thickness finger plate(s) 4a, 4b can be selected with a suitable thickness(es) and inserted to fill any such gap remaining between the end finger plate 4 and the inside wall of the base block 1. As discussed herein, the cam shaft 2 can be threaded through the apertures of the finger plates 4 and rotatably mounted at either end by mounting holes in the pump mechanism base block 1 for cam shaft bearings 19. Cam shaft bearings 19 can be inserted into pump mechanism base block 1 and press fit to secure the cam shaft 2 to the base block 1. Bevel gear 6 can be disposed at an exposed end of cam shaft 2, as discussed herein.

The distance or gap between the occlusion block 9 and the peristaltic finger plates 4 can be adjusted using set screws 23 to adjust the location of the hinge pin 15. For purpose of illustration and not limitation, the hinge pin 15 can determined the position of the lock member 11 and the location of the occlusion block 9. Set screws 23 can be tightened to urge the latch hinge pin 15 to an initial position. The bevel gears 6 can be rotated to position the finger plates 4, as shown for purpose of illustration and not limitation. The outer finger plates 4 can initially be closest to the occlusion block 9. The rear pin 10 can be inserted and the lock member 11 can be closed. To calibrate the distance or gap between the finger plates 4 and the occlusion block 9, an object of a known thickness can be inserted into the gap formed between the finger plates 4 and the occlusion block 9. For example and not limitation, as embodied herein, the object can be a pin with a known thickness, such as a 0.112" gauge pin. For purpose of illustration and not limitation, the object can be inserted into the gap formed between the finger plates 4 and the occlusion block 9 on the inlet side. If the object drops passes through the gap, the set screws 23 on that side can be adjusted to decrease the gap. The inserting of the object through the gap can be repeated on the inlet side until the object does not pass through. Additionally, another object of a slightly less thickness can be passed through the gap to confirm that the gap has the desired size. For example and not limitation, as embodied herein, the other object can be a pin of a smaller gauge such as a 0.111" gauge pin. If the other object passes through the gap, the gap is appropriately sized. If the other object does not pass through the gap, the set screws can be adjusted to increase the gap. This process can be repeated at the outlet side.

The lock member 11 can be configured as a cam lever and actuated to move the occlusion block 9 into place when loading a new tube. The rear pin 10 can operate to stabilize the tubing cartridge in the housing, and can be actuated when lock member 11 is actuated. Torsion springs 12, 20 can lift the lock member 11, for example, when the lock member 11 is not fully seated. Extension spring(s) 8 can urge the occlusion block away from the finger plates 4 when the lock member 11 is lifted.

For purpose of illustration and not limitation, a top cover 14 can be provided. The top cover 14 can be secured with screws 18. Additionally or alternatively, a magnet 22 can be included. For example and not limitation, the magnet 22 can be included in the lock member 11. A sensor (not pictured) can be added to the base block 1 to sense the magnet 22. For example, the sensor can be a reed switch, which can be operated by the magnetic field of the magnet 22 when lock member 11 is in the closed position. As such the magnet 22 and sensor can help to ensure proper and safe operation of the pump assembly 100.

As embodied herein, the motor assembly 3 can be mounted to the base block. For example and not limitation, such mounting can reduce the space occupied by the pump assembly 1700 compared to mounting the motor assembly 3 to the pump housing.

Figure 2A:
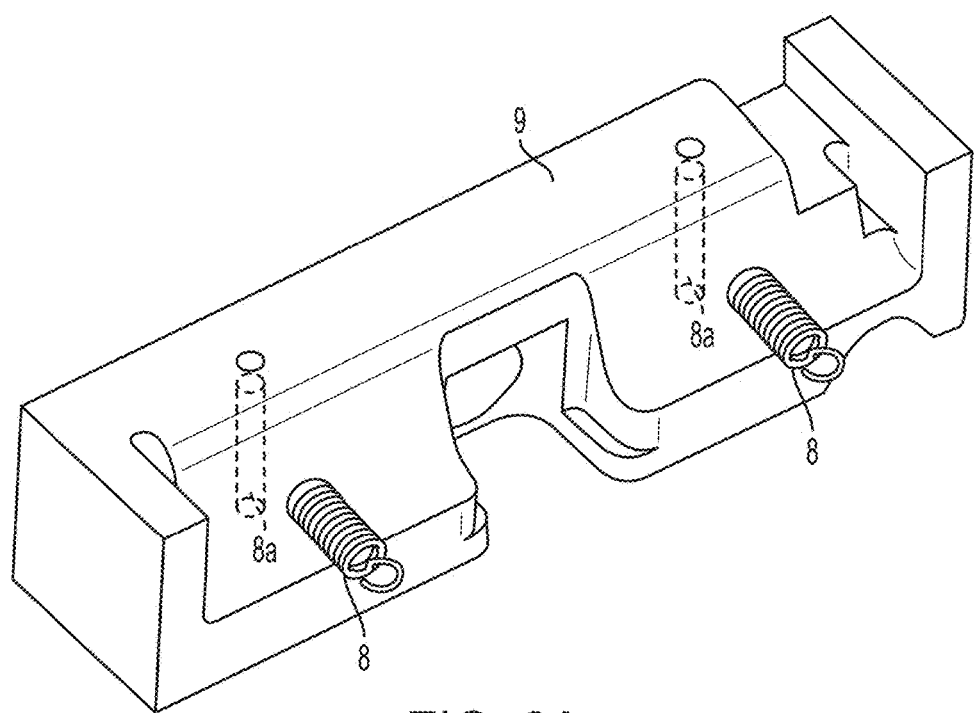
FIG. 2A is a perspective view of an exemplary occlusion block of the pump assembly of FIG. 1B.
Figure 2B:
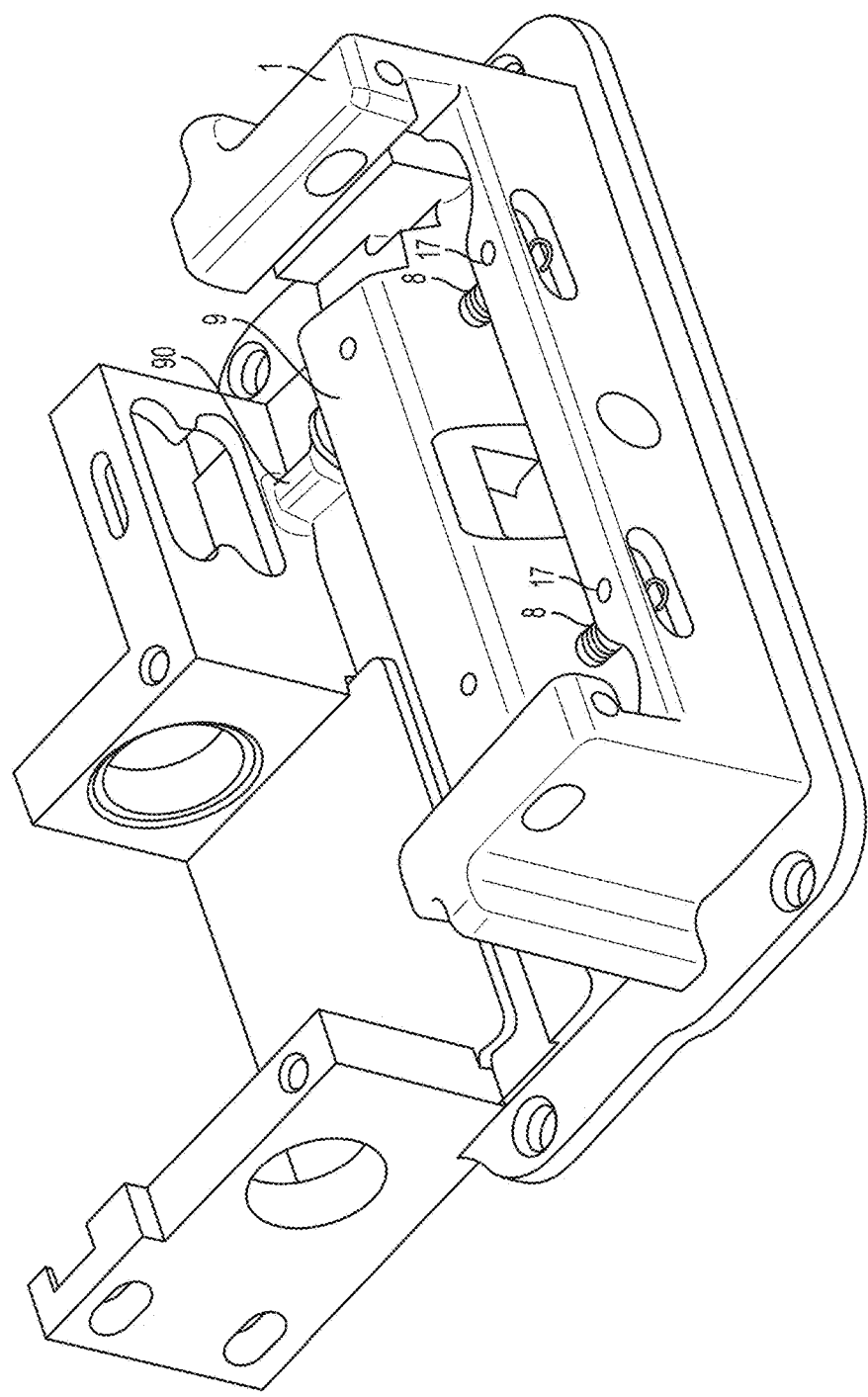
FIG. 2B is a perspective view of the occlusion block of FIG. 2A joined to an exemplary base block of the pump assembly of FIG. 1B.

With reference to views of the various components as depicted in FIGS. 2A-2H, the pump assembly 100 can be configured as follows. An occlusion block 9 can be provided, for example as shown in FIG. 2A. Extension springs 8 can be secured to occlusion block 9, for example by inserting each spring 8 through clearance holes in occlusion block 9 and insert spring retention pins 8a through the holes and pressing the pins into the occlusion block 9. The assembled occlusion block 9 can be inserted into the pump mechanism base block 1, as shown for example in FIG. 2B. Spring retainer pins 17 can be inserted into pump mechanism base 1, and a free end of extension springs 8 can be urged over spring retainer pin, which can be press fit into pump mechanism base 1 to secure the extension springs 8.

A plurality of finger plates 4 can be placed in the cavity of the pump mechanism base block 1, as shown for example in FIG. 2C. As embodied herein, for purpose of illustration, twenty-seven finger plates 4 are depicted, and are slidably disposed between end walls of the base block 1. A gap can be defined between an end finger plate 4 and the inside wall of the base block 1, and as such, a non-standard thickness finger plate 4a, 4b can be selected with a suitable thickness and inserted to fill any such gap remaining between the end finger plate 4 and the inside wall of the base block 1. Each finger plate 4 has an aperture 41 defined therethrough, as described further below, which is aligned with mounting holes 1a shown in FIG. 2C.

Figure 2D:
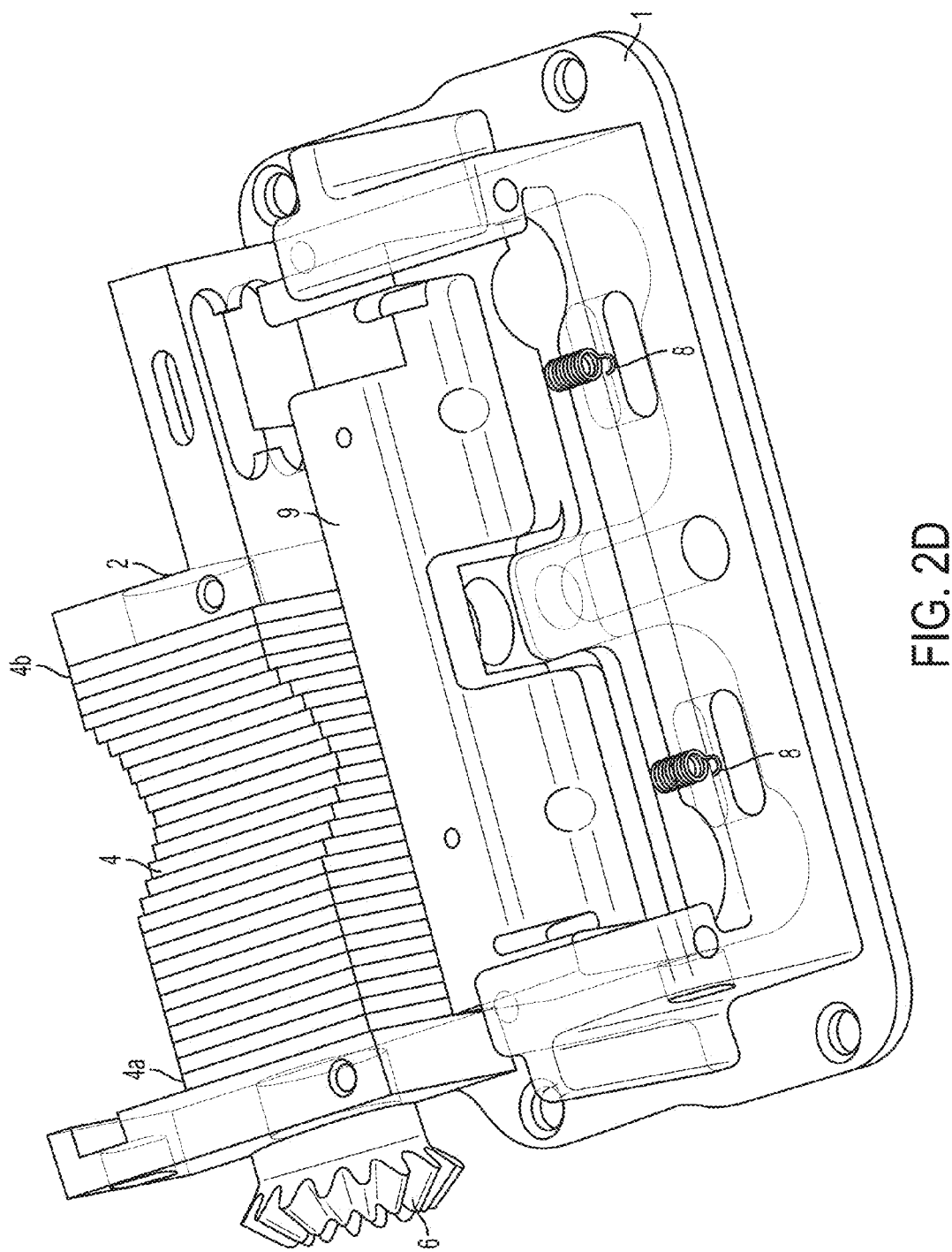
FIG. 2D is a perspective view of an exemplary cam shaft joined to the base block of FIG. 2C.

The cam shaft 2 is provided with a radially-outward projection 21 as described further below, and threaded through the apertures 41 of the finger plates 4 and mounting holes 1a of base block 1, as shown for example in FIG. 2D. In this manner, cam shaft 2 is rotatably mounted at either end by mounting holes 1a in the pump mechanism base block 1 with cam shaft bearings 19, as described further below. That is, cam shaft bearings 19 can be inserted into pump mechanism base block 1 and press fit to secure the cam shaft 2 to the base block 1. A bevel gear 6 can be disposed at an exposed end of cam shaft 2. As embodied herein, a pin hole on bevel gear 6 and cam shaft 2 can be aligned, and a bevel gear retaining pin (not shown) can be inserted therein and press fit into the gear/shaft assembly.

Figure 2E:
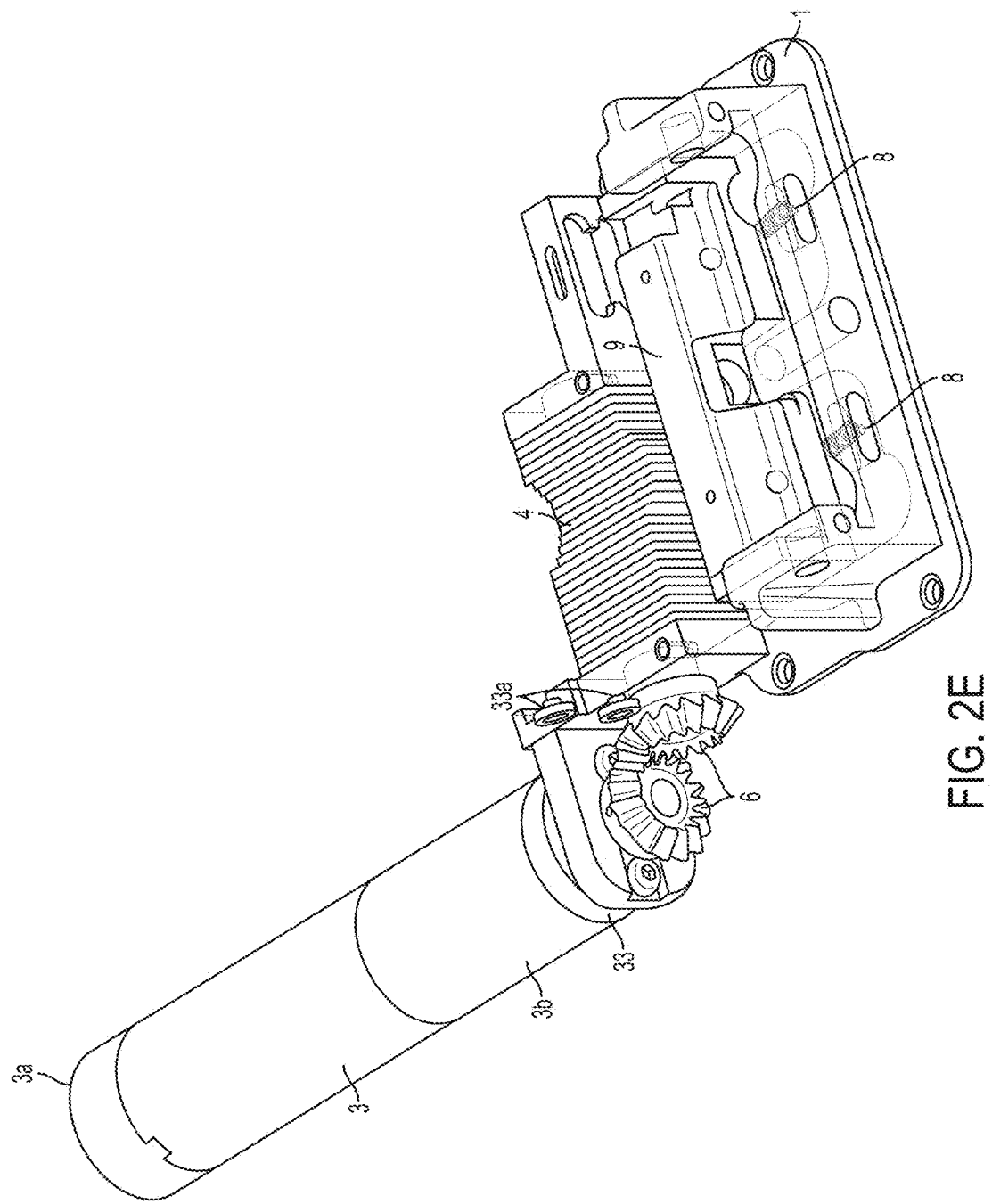
FIG. 2E is a perspective view of an exemplary motor assembly joined to the base block and cam shaft of FIG. 2D, with portions cut away for purpose of illustration.

With reference to FIG. 2E, the motor assembly can include a motor, gearbox and encoder. A side mount bracket 33 can be installed over a face of the motor 3, as shown, and can be secured to the motor 3, for example using screws 33a. Alternatively, a mount bracket for the motor assembly can be integral with base block 1. A bevel gear 6 can be inserted onto an end of a shaft of motor 3, and a pin hole in bevel gear 6 can be aligned with a pin hole on the shaft. A gear pin can be inserted into the pin hole and press fit to secure the bevel gear 6 to the motor 3. In this manner, the motor assembly is adjustable relative the bevel gear 6 and cam shaft 2 for proper alignment. Motor assembly can include an encoder 3a configured to provide position and/or speed control of motor 3, as described further herein.

Mount bracket to mount motor assembly 3 can be aligned with mounting holes provided in the pump mechanism base block 1 and secured, for example using mounting screws. A gap between the occlusion block face 9 and the surface of the finger plates 4 can be formed, and can be adjusted using the occlusion block set screws, as discussed herein, to a predetermined dimension. The dimension can be suitable to allow the finger plates to contact and compress a liquid or gel-containing peristaltic tube therein.

Figure 2F:
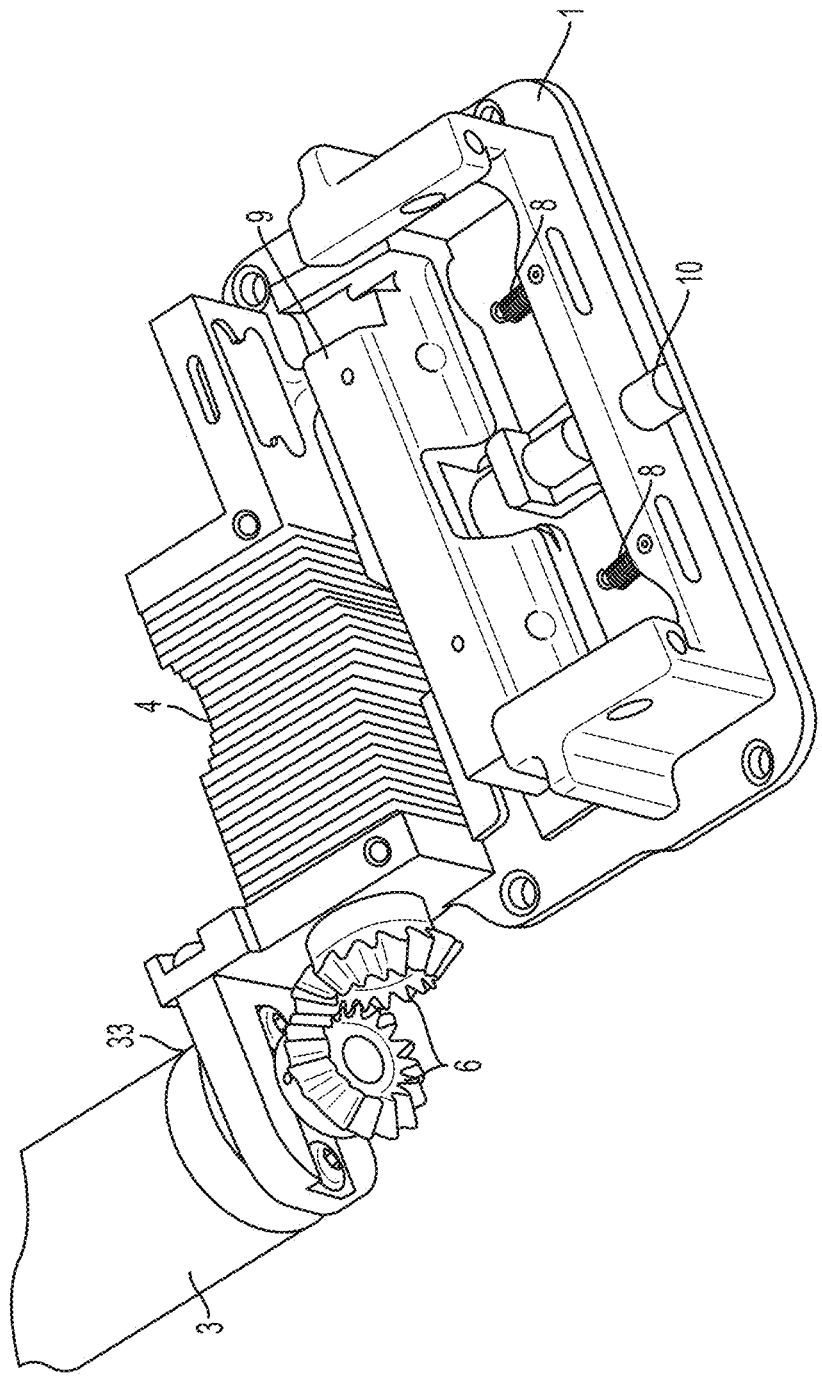
FIG. 2F is a detail view of a portion of FIG. 2E.
Figure 2G:
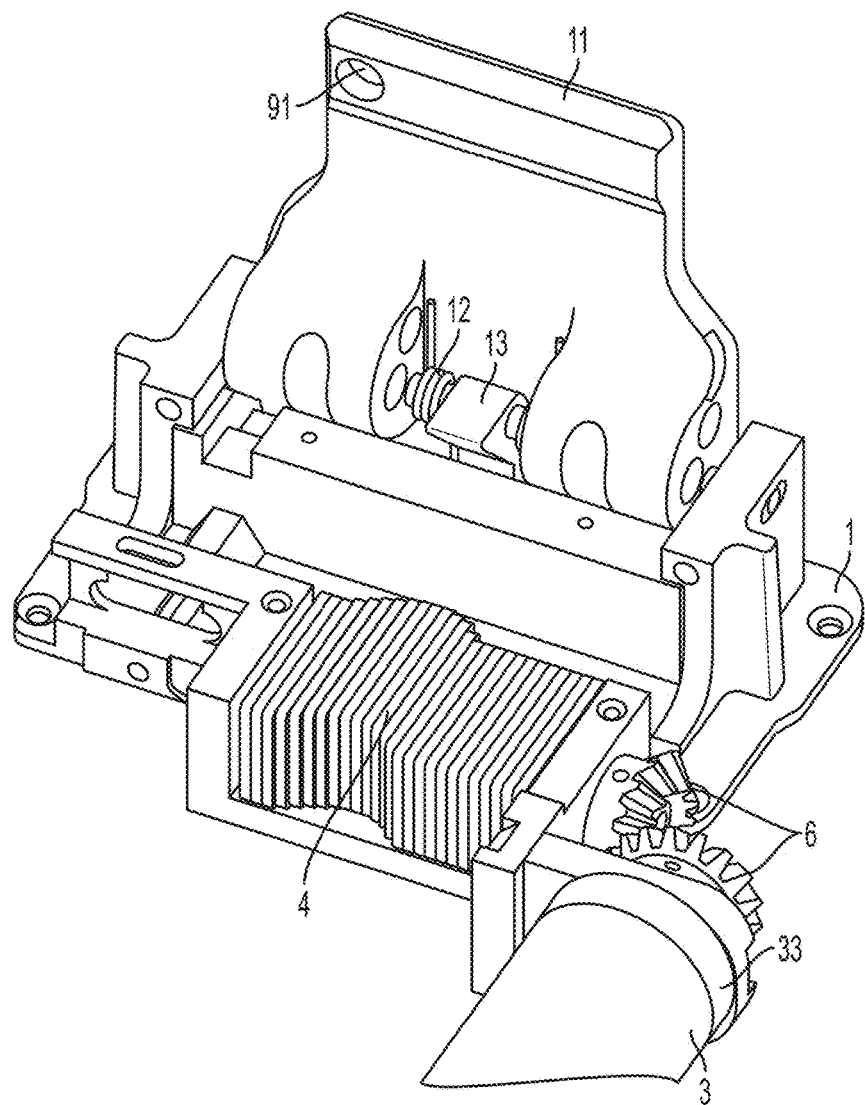
FIG. 2G is a detail perspective view of an exemplary lock member joined to the base block of FIG. 2F.
Figure 2H:
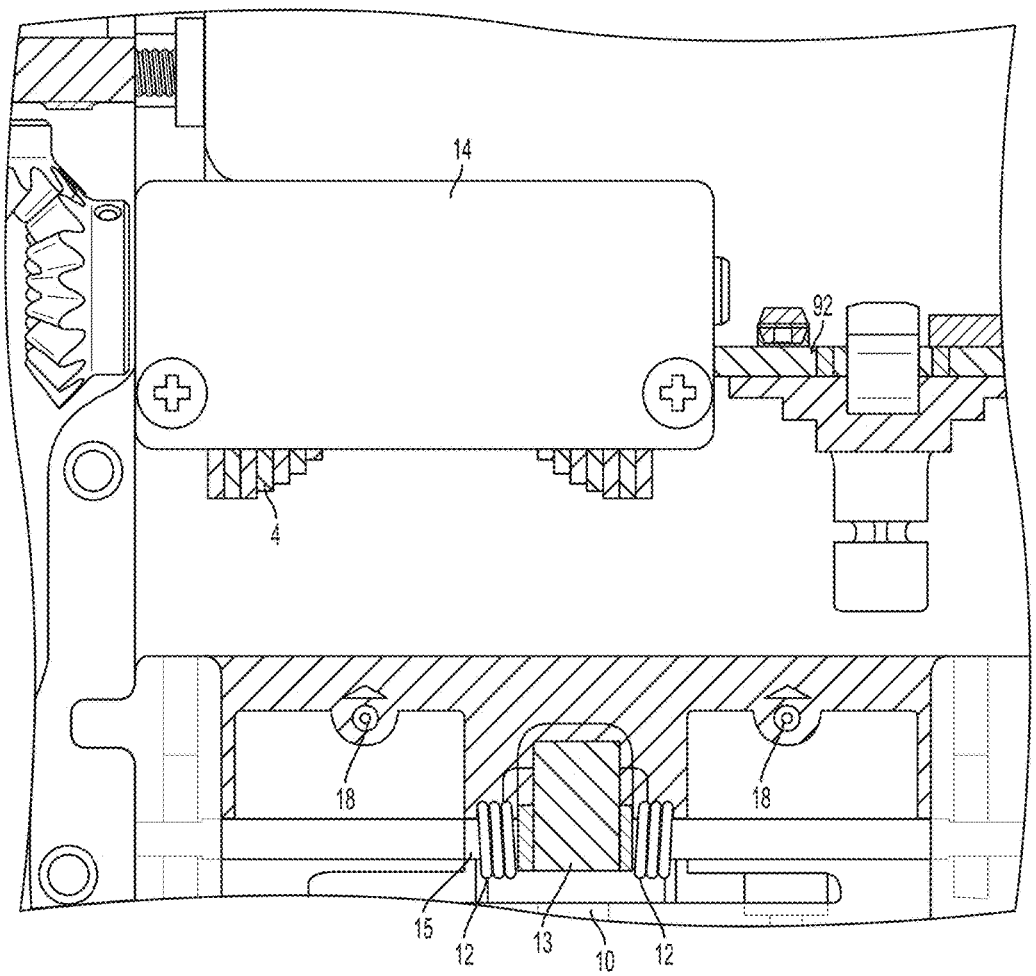
FIG. 2H is a bottom plan view of the pump assembly of FIG. 2G.

As shown for example in FIGS. 2F-2H, a lock member 11 can be assembled onto the pump base 1. For example, a rear pin 10 can be inserted into the pump base 1 to secure a pin driver 13 having an upward-facing notch, as shown for example in FIG. 2F. The lock member 11, pin driver 13 and torsion spring 12 can be aligned and a latch hinge pin 15 can be inserted into the lock member 11 and through the pin driver 13 and torsion spring 12. One or more set screws 18 can be inserted into pump base 1 to adjust the occlusion block 9 position, as discussed further herein.

Referring now to FIGS. 3A-3D, an exemplary embodiment of a finger plate 4 is shown. Finger plates 4 each have recessed areas 42 in at least one side surface thereof, proximate opening 41. As depicted herein, the recessed areas 42 reduce surface friction between adjacent finger plates 4 during movement relative one another. For example, and as embodied herein, each recess 42 can have a depth of about 0.1 mm relative to the corresponding surface of the finger plate 4. As further depicted herein, the recessed area of each finger plate 4 does not extend to the surface of the finger plate disposed adjacent the peristaltic tube. In this manner, the tube interaction surface 43 of each finger plate 4 is generally planar and together the finger plates 4 can define a contiguous surface for improved pumping performance and accuracy.

As embodied herein, the finger plates 4 can be symmetrical. For purpose of illustration and not limitation, the finger plate 4 can have a D-shaped opening 41. The shape of opening 41 can improve moldability, for example by allowing material to flow into each part of a mold more easily compared to other opening shapes, e.g., rectangular. To strengthen the flat portion of the D-shape opening 41, the amount of material proximate the area of contact with camshaft 2 can be increased. For purpose of illustration and not limitation, the finger plates 4 can be made of any suitable material (e.g., plastic, ceramic, composites, metal, etc.). For example, the finger plates can be made out of a plastic, such as commercially available Delrin 520 MP or RTP 1399, or ceramic material.

With reference to FIGS. 4A-4D, an alternative embodiment of a finger plate 4' is shown, having alternative dimensions compared to finger plate 4. Referring now to FIGS. 5A-5D, an alternative embodiment of a finger plate 4" is shown, having alternative dimensions compared to finger plate 4. For purpose of illustration and not limitation, optional smaller finger plate(s) 4a and larger finger plate(s) 4b can be included. For example and not limitation, during assembly the overall dimensions of the combined finger plates 4 can be evaluated, and certain finger plates 4, for example one or more end finger plates 4 can be replaced with a smaller finger plate 4a or a larger finger plate 4b to achieve a desired fit.

Figure 6A:
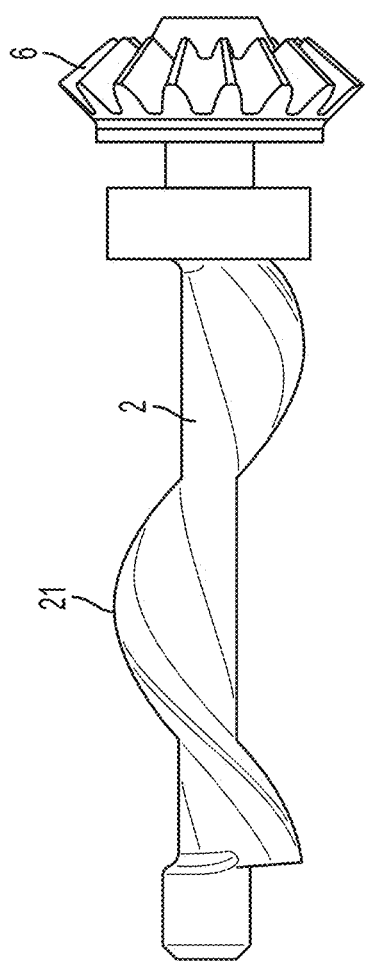
FIG. 6A is a plan view of an exemplary cam shaft joined with an exemplary bevel gear for use with the pump assembly of FIG. 1B.
Figure 6C:
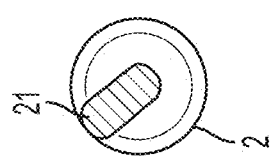
FIG. 6C is a cross-sectional view of the exemplary cam shaft taken along line 6C-6C of FIG. 6B.
Figure 6B:
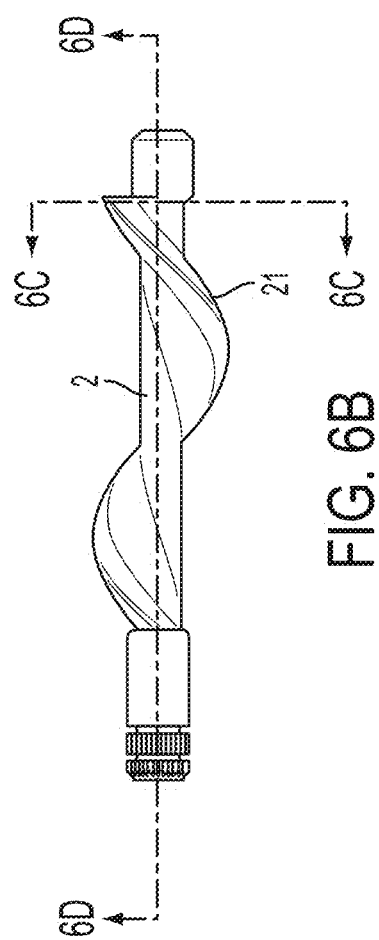
FIG. 6B is a plan view of the exemplary cam shaft of FIG. 6A.
Figure 6D:
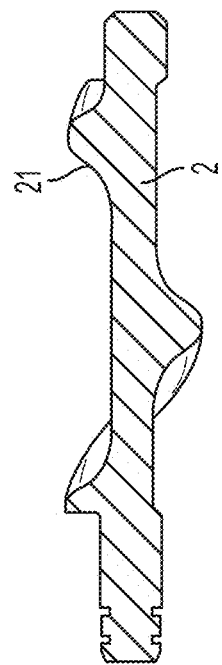
FIG. 6D is a cross-sectional view of the exemplary cam shaft taken along line 6D-6D of FIG. 6B.
Figure 6H:
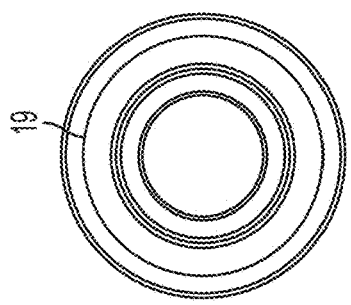
FIG. 6H is a cross-sectional view of the exemplary bearing of FIG. 6G taken along line 6H-6H of FIG. 6G.
Figure 6G:
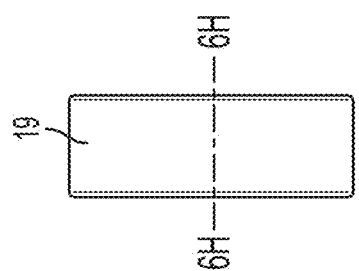
FIG. 6G is a side view of the exemplary bearing of FIG. 6A.
Figure 6F:
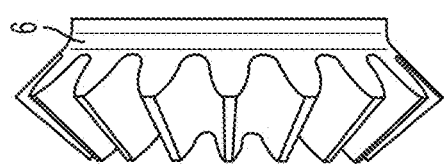
Figure 6E:
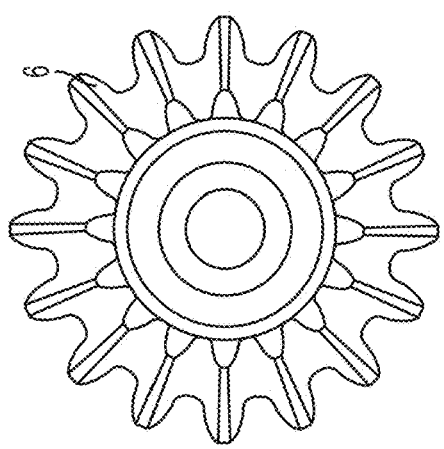
FIG. 6E is a front view of the exemplary bevel gear of FIG. 6A.

FIG. 6A illustrates an exemplary camshaft 2, bearing 19, and bevel gear 6. FIGS. 6B-6D illustrate further features of exemplary camshaft 2. Additionally FIGS. 6E-6F illustrate further features of exemplary bearing 19. FIGS. 6G-6H illustrate further features of exemplary bevel gear 6. With reference to FIGS. 6A-6H, for purpose of illustration and not limitation, camshaft 2 can have increased load capacity compared to certain cam shafts for similar applications. For example and not limitation, the journal diameter can be 50% greater than certain camshafts for similar applications. Additionally, the camshaft 2 can be made of any suitable material (e.g., plastic, ceramic, composites, metal, etc.). For example, and as embodied herein, the material can be a ceramic material, such as and without limitation, zirconium oxide ceramic. Camshaft 2 can be lubricated with any suitable lubricant to reduce frictional forces, such as, without limitation, DuPont™ Krytox® GPL205, TURMOGREASE Highspeed L 182 (LUBCON Turmo® Lubrication), TURMOPOL GREASE LC 2201 (LUBCON Turmo® Lubrication) and Turmopol Oil 68 HT (LUBCON Turmo® Lubrication). Furthermore, and as embodied herein, the cam shaft 2 can include a chamfered portion formed at the end of the helical portion to prevent contact with the outer bearing 19. Additionally, and as embodied herein, the tolerances of the attachment of the camshaft 2 to the bevel gear 6 can be improved by using an over molded bevel gear 6, as compared to, e.g., a pin. Using an over molded bevel gear 6 can also reduce manufacturing steps of the pump assembly 1700.

Figure 7C:
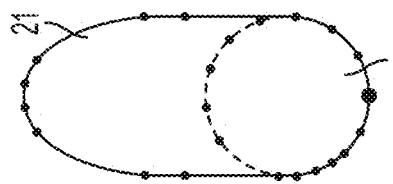
FIGS. 7A-7C each is an alternative embodiment of a cam shaft protrusion according to the disclosed subject matter, each illustrating an alternative cam shaft contacting surface.
Figure 7B:
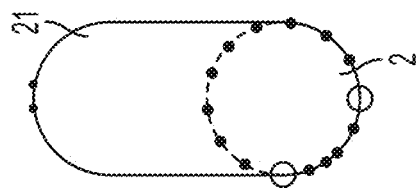
Figure 7A:
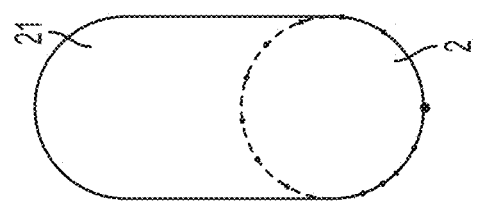

FIGS. 7A-7C show the profile for the contacting surfaces of exemplary camshafts. For purpose of illustration and not limitation, certain other camshafts for similar applications can be configured with a generally flat surface to contact the finger plates. For purpose of comparison, as shown for example in FIG. 7A, a rounded profile for contacting can create a point contact that can wear down the flat section of the opening in the finger plates 4 and distort the shape of the opening. As embodied herein, the exemplary camshaft 2 can have a flattened egg shape for the profile of the helical camshaft, as shown for example in FIG. 7C. The egg shape can distribute the force from the camshaft 2 to the finger plates 4 over a larger surface. As such, the overall wear of the camshaft 2 on the finger plates 4 can be reduced.

Figure 8A:
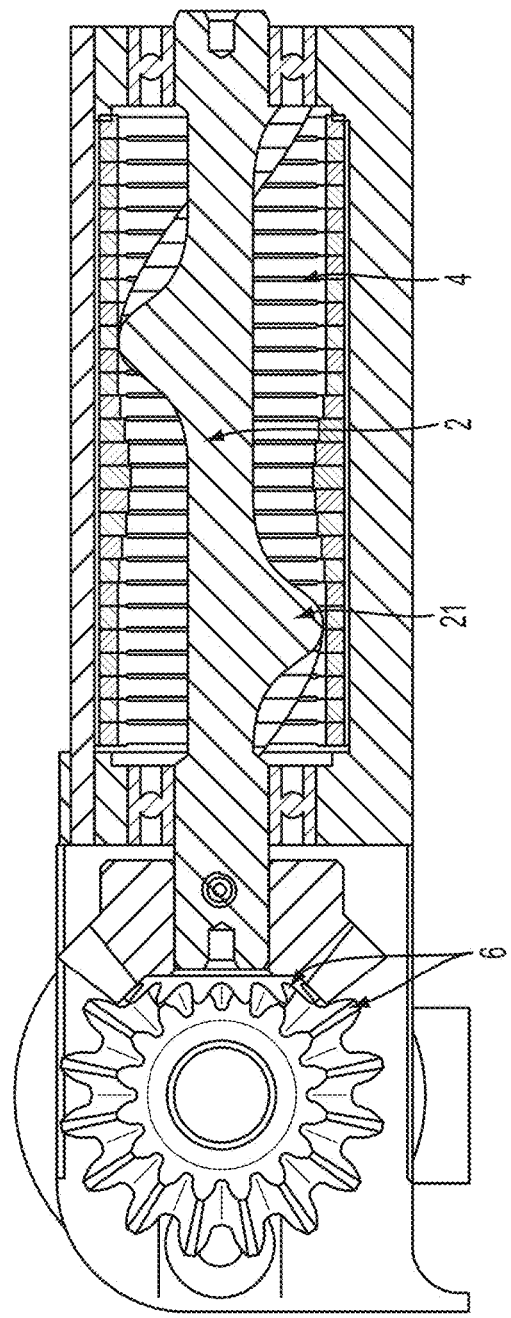
FIG. 8A is a partial cross-sectional view taken along a longitudinal axis of the exemplary cam shaft, illustrating the cam shaft interacting with exemplary finger plates of the pump assembly of FIG. 1B.
Figure 8B:
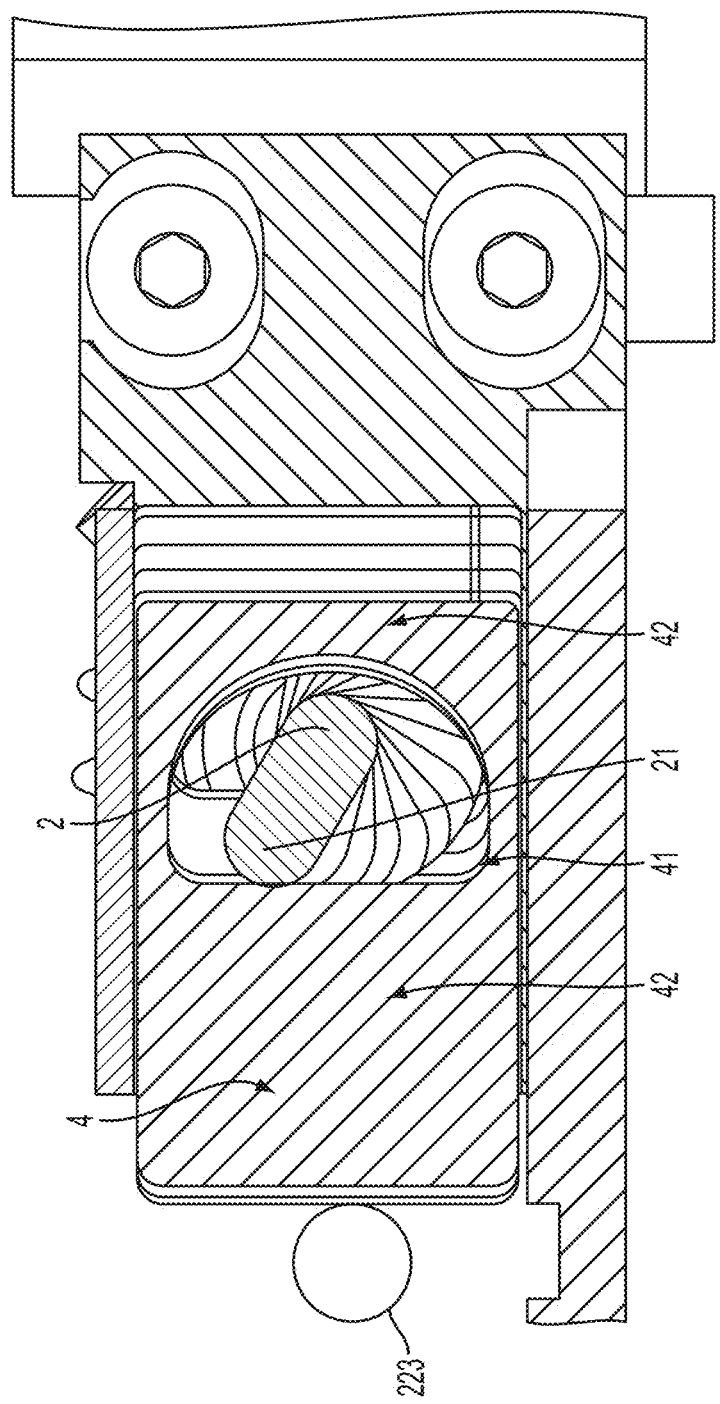
FIG. 8B is a partial cross-sectional view taken along an axis transverse to the longitudinal axis of the cam shaft of FIG. 8A, illustrating the cam shaft interacting with exemplary finger plates of the pump assembly of FIG. 1B.

Referring now to FIGS. 8A-8C, exemplary features of the interaction of camshaft 2 with finger plates 4 are illustrated. In operation, the pump assembly 100 can operate as a fluid drive component. As embodied herein, the motor 3 turns bevel gears 6, which turns cam shaft 2. As shown for example in FIGS. 6A-6D, cam shaft 2 has a radially-outward projection 21 defining a helical engagement portion disposed along a length of the cam shaft 2. FIGS. 8A-8C each is a cross-sectional schematic diagram illustrating the finger plates 4 interacting with the cam shaft 2 and the occlusion block 9. As shown in FIG. 8A, projection 21 engages finger plates 4 to urge each finger plate 4 transversely in sequence toward occlusion block 9 to compress an adjacent portion of a peristaltic tube (not shown) disposed proximate occlusion block 9. The compression of the peristaltic tube urges a liquid or gel within the peristaltic tube in a direction out of the peristaltic tube. Further rotation of the cam shaft 2 urges each finger 4 plate away from occlusion block 9 to release the peristaltic tube. The release of the compressed peristaltic tube thus can create a vacuum force within the peristaltic tube to draw additional fluid from the fluid source into the peristaltic tube. In this manner, and as discussed further herein, the position of the finger plates 4 with respect to the peristaltic tube is controlled by the angular position of the rotatable cam shaft 2 within the aperture 41. Additionally or alternatively, the finger plates 4 can be biased, for example toward the return position away from occlusion block 9.

As embodied herein, the camshaft 2 can have a round lobe or projection 21 that wraps around the shaft in a helical shape. The helical shape of the projection 21 can wrap around the camshaft 2 slightly greater than one revolution. As such, in operation, as the camshaft 2 rotates, at least a portion of the camshaft 2 can be acting on a sufficient number of finger plates 4 to ensure the tubing interfacing with the finger plates 4 remains occluded throughout each rotation. In this manner, fluid can be urged to flow in a single direction.

The interaction of the camshaft 2 with the D-shaped opening 41 of a series finger plates 4 can produce a peristaltic pumping motion. The helical lobe 21 can exert a force on the finger plates 4 as it rotates, which can result in motion of the finger plates 4 perpendicular to the camshaft 2, as shown for example in FIG. 8C. Additionally, as shown for example in FIG. 8B, as the camshaft 2 rotates, the portion of the camshaft 2 projection 21 engaging the finger plate 4 can urge the finger plate 4 at different locations within the D-shaped opening 41. For example and not limitation, the camshaft 2 and the opening 41 can be configured such that contact can be made with a central portion of the flat and curved portions of the D-shaped opening 41 and no contact can be made with outer corner portions of the opening 41, for example as illustrated in FIG. 8B. As no contact can be made with the outer corner portions of the D-shaped opening 41, the finger plates 4 can be urged to move in a single axis. The camshaft 2 can also include an over molded bevel gear 6 formed at an end thereof for coupling with the motor 3 and mounting features of the base block 1 to hold the camshaft 2 in the pump assembly 100, as described herein.

Referring now to FIG. 8B, each finger plate 4 has an aperture 41 to receive the cam shaft 2 proximate a segment of engagement portion 21. Each aperture 41 depicted herein has a substantially flat edge 44 at a first end proximate the occlusion block 9, and a substantially arcuate edge 45 at a second end opposite the first end. With reference to FIG. 8B, rotation of the cam shaft 2 and engagement portion 21 rotates engagement portion 21 into engagement with the substantially flat edge 44, and urges finger plate 4 toward occlusion block 9 a distance to urge the peristaltic tube engagement surface 43 into engagement with a peristaltic tube disposed therein. Further rotation of the cam shaft 2 maintains engagement portion 21 in engagement with flat edge 44 and maintains finger plate 4 in engagement with the peristaltic tube. Rotation of cam shaft 2 and engagement portion 21 beyond flat edge 44 moves engagement portion 21 along a side of the aperture 41 and into engagement with arcuate edge 45, which urges finger plate 4 away from occlusion block 9 and out of engagement with the peristaltic tube. Alternatively, for purpose of illustration and not limitation, finger plates 4 can be biased away from occlusion block 9 along the single axis. For example, finger plates 4 can be biased away from occlusion block 9 by force exerted from peristaltic tube 223 to urge finger plates 4 away from peristaltic tube 223 when not engaged by camshaft 2. As such, camshaft 2 can be configured to engage flat edge 44 to engage peristaltic tube 223 and not engage arcuate edge 45.

The cam shaft 2 is coupled to the motor 3 for rotation about a longitudinal axis of the cam shaft 2, and has at least one radially-outward projection 21 defining a helical engagement portion disposed along a length of the cam shaft. The plurality of finger plates 4 are disposed along the length of the cam shaft. Each finger plate 4 is mounted for movement in a transverse direction relative to the longitudinal axis of the cam shaft, and is in operative engagement with the helical engagement portion to move transversely between an extended position and a return position. The processor is in operative communication with the encoder 3b to receive rotation data to determine an amount of rotation of motor 3.

As discussed further herein, one or more processors can determine an amount of rotation of motor 3 and/or cam shaft 2. The processor can be in communication with one or more memories to store the rotation data from encoder 3b over time. Using the rotation data from encoder 3b, the processor can determine an amount of rotation of the motor 3 or cam shaft 2 over a certain period of time, for example to determine a motor velocity. A predetermined relationship between the rotation of the motor 3 or cam shaft 2 and a sequential movement of finger plates 4 resulting in an amount of beneficial agent dispensed can be utilized to determine an amount of beneficial agent dispensed using the amount of rotation of the motor 3 or cam shaft 2. Additionally or alternatively, the processor can be operative to activate the motor 3 for a certain period of time, for example by operating the motor 3 until a desired amount of beneficial agent has been dispensed.

According to another aspect of the disclosed subject matter, and further to the above, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a fluid drive component disposed proximate the receiving region, a main controller circuit board coupled to and configured to control the fluid drive component, and at least one secondary circuit board foldably joined to the main controller circuit board through a flexible substrate and disposed within the interior in a stacked relationship relative the main controller circuit board. A plurality of such secondary circuit boards can be provided, each joined to the main controller circuit board by a flexible substrate either directly or indirectly.

For example, and as embodied herein, the at least one secondary circuit board can include a power source controller board coupled to a power source. The at least one secondary circuit board can include an occlusion sensor controller board coupled to an occlusion sensor. The at least one secondary circuit board can include a serial bus controller board. The serial bus controller board can include an electromagnetic compatibility component. The serial bus controller board can include a serial bus port disposed proximate an exterior wall of the pump housing and aligned with an aperture in the exterior wall.

Furthermore, and as embodied herein, the at least one secondary circuit board can include a motor signal encoder coupled to the fluid drive component. The fluid drive component can be coupled to the motor signal encoder in a stacked relationship with the main controller circuit board. The at least one secondary circuit board can include a speaker, alone or with an audio amplifier. The at least one secondary circuit board can include a haptic actuator.

In addition, and as embodied herein, the at least one secondary circuit board can include a display controller coupled to a display. The display can further include a liquid crystal display (LCD). The display can further include a flexible light transmission component in optical communication with the LCD. The at least one secondary circuit board can include an input controller. The input controller board can include a plurality of input buttons disposed proximate an exterior wall of the pump housing and aligned with corresponding apertures in the exterior wall. The pump housing can have an interior having a height within a range of 18.5 mm to 20 mm. The flexible substrate can include polyimide, copper-clad polyimide, polyether ether ketone, transparent conductive polyester film, or a combination thereof. The flexible substrate can have a thickness within a range of 95 µm to 192.5 µm.

In accordance with this aspect of the disclosed subject matter, the apparatus and methods herein can include one or more of the features described above. For purpose of illustration and not limitation, with reference to FIG. 9, the pump assembly includes a pump printed circuit board (PCB) assembly 200 joined to pump components. The pump PCB assembly 200 can include a main controller circuit board 202, which, for purpose of illustration and not limitation, can be configured as a rigid flex PCB assembly using known construction techniques as illustrated for example in FIG. 9. A remainder of the PCB assembly 200 can articulate around main controller circuit board 202 at several flex sections 204 to allow the PCB to conform and fold to fit the enclosure. In this manner, several secondary or satellite boards can provide functionality for certain functions proximate their point of use.

For purpose of illustration and not limitation, and as embodied herein, a secondary circuit board can include battery PCB assembly 206, which can provide reverse battery protection, fusing, and proper creepage or clearance to meet regulatory requirements as well as including a battery connection 208, e.g., springs, to join a power source 210, embodied herein as batteries 210, to pump PCB assembly 200. Occlusion sensing can be performed in the pump mechanism, as described further herein, and a secondary circuit board can include a dedicated occlusion sensing PCB assembly 212, which can provide, for purpose of illustration and not limitation, latch detection. Additionally or alternatively, and as embodied herein, a secondary board can include a serial bus PCB assembly 214, which can include EMC components and can provide a suitable mounting location for a serial bus connector 216, which can be any suitable connector for data bus communication, including but not limited to a USB connector. Furthermore, and as embodied herein, a secondary circuit board can include a button PCB assembly 224, which can have buttons joined thereto and disposed on an exterior face of the pump housing to provide input from a user to the pump assembly 100.

Figure 9:
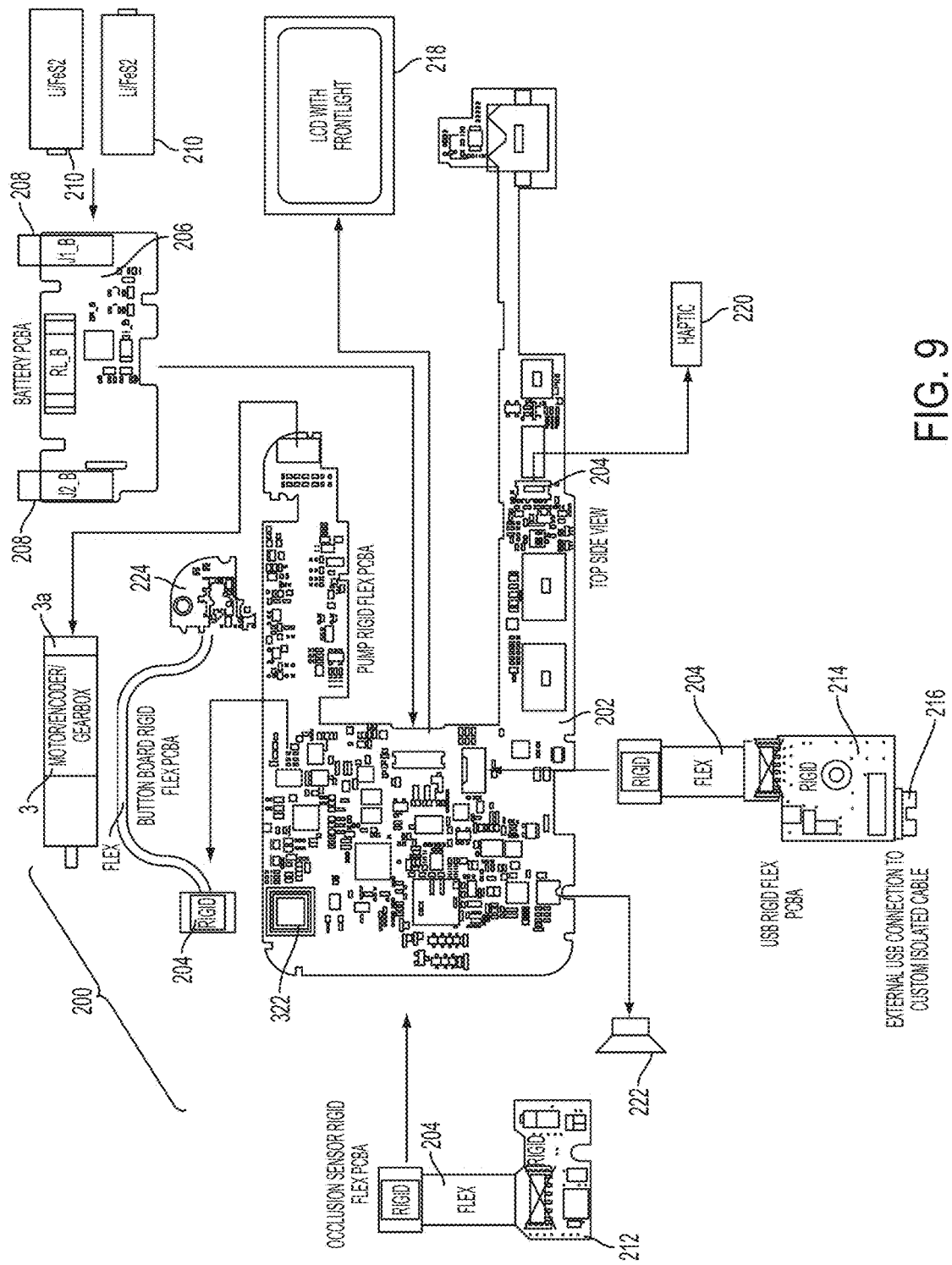
FIG. 9 is a schematic diagram illustrating an exemplary circuit board assembly for a beneficial agent delivery device according to the disclosed subject matter.
Figure 10A:
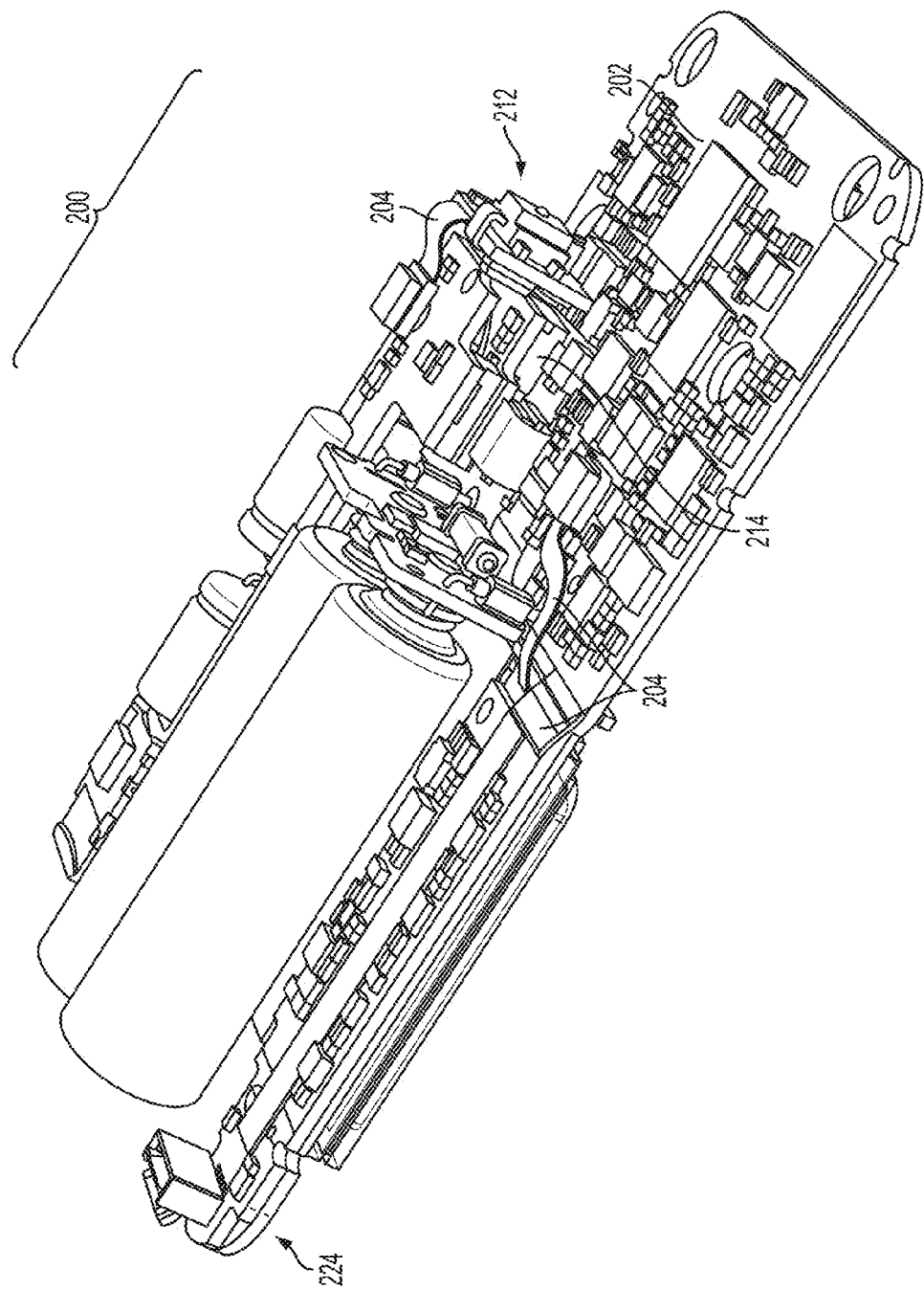
FIG. 10A is a perspective view of a physical layout of an exemplary circuit board assembly for a beneficial agent delivery device according to the disclosed subject matter.
Figure 10B:
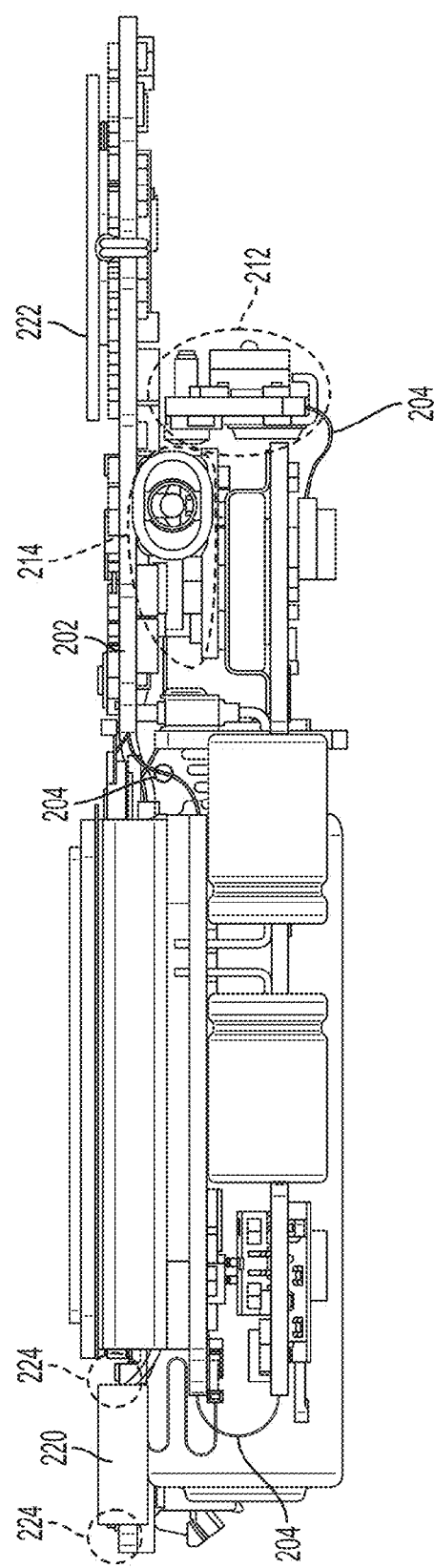
FIG. 10B is a side view of the exemplary circuit board assembly of FIG. 10A.
Figure 10C:
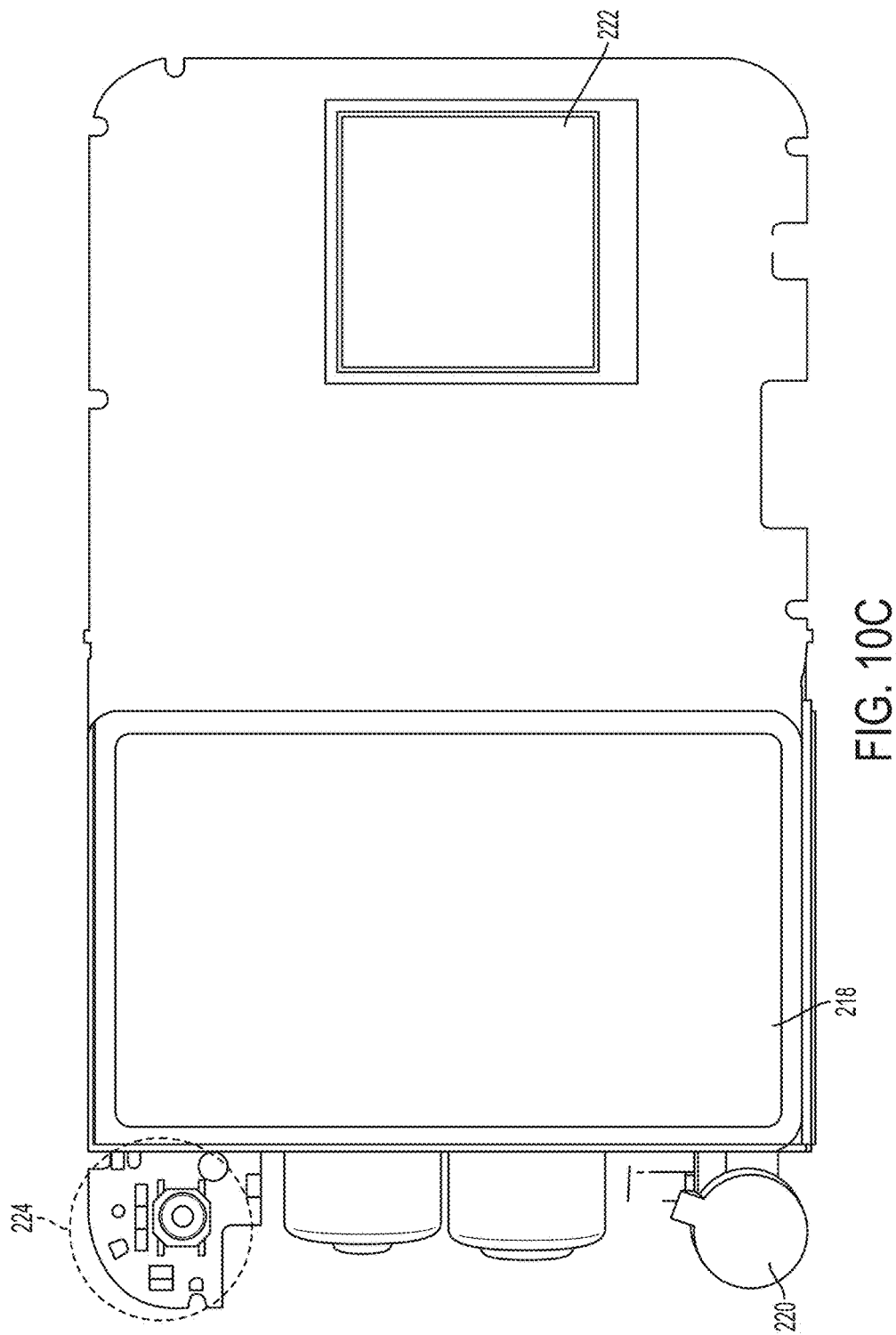
FIG. 10C is a top plan view of the exemplary circuit board assembly of FIG. 10A.
Figure 10D:
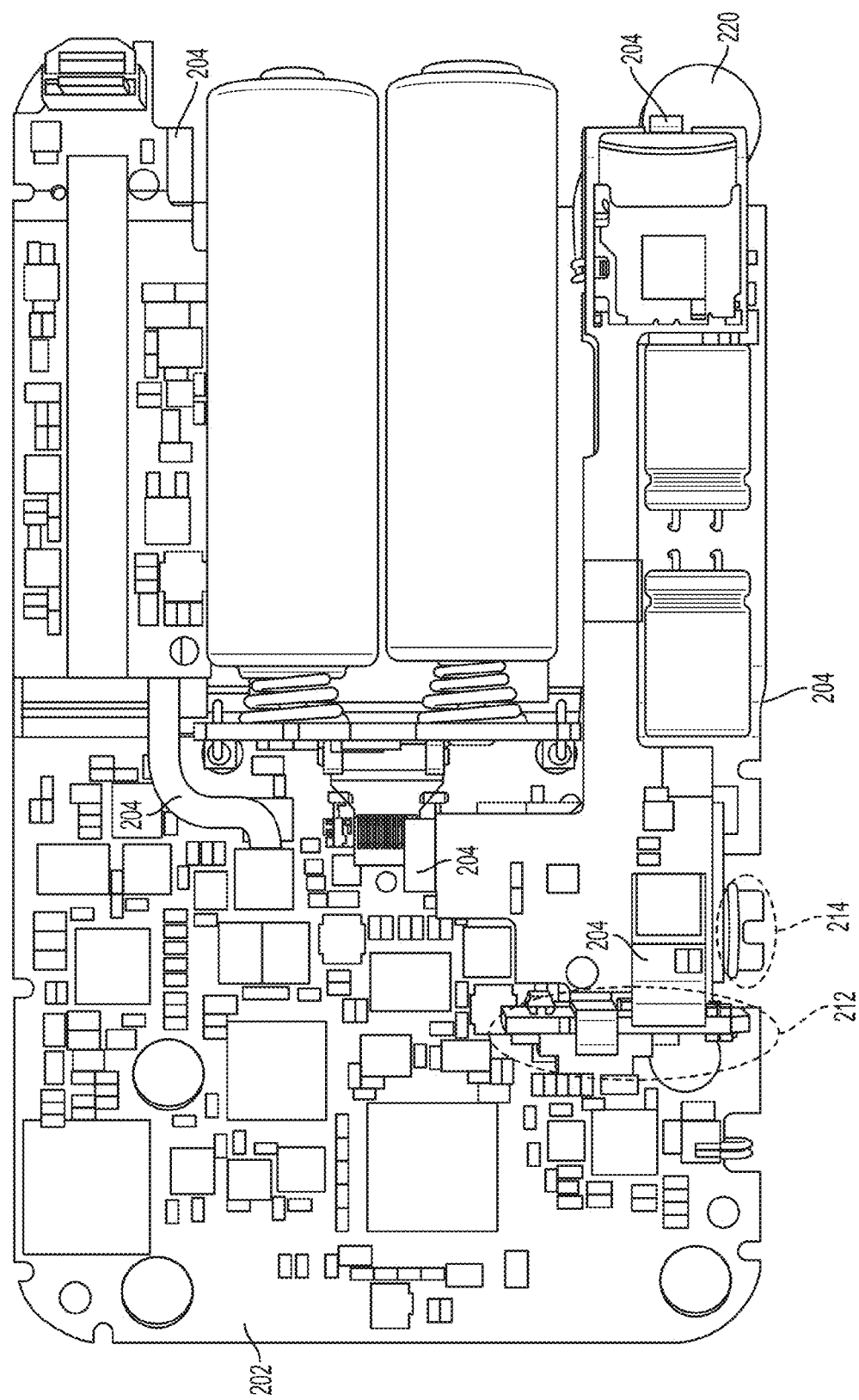
FIG. 10D is a bottom plan view of the exemplary circuit board assembly of FIG. 10A.

Referring still to FIG. 9, pump PCB assembly 200 can have various off-board components joined thereto. For purpose of illustration, and not limitation, pump PCB assembly 200 can have a motor 3 with an encoder 3a joined to main controller board 202. Additionally or alternatively, pump PCB assembly 200 can have a display 218, embodied herein as a liquid crystal display (LCD) with flexlight joined to main controller board 202. As a further alternative, pump PCB assembly 200 can have a haptic actuator 220 and/or a speaker 222 joined to main controller circuit board 202, for example to provide tactile or audible feedback to a user. The off-board components can be joined to pump PCB assembly by any suitable connection, including but not limited to rigid flex connection and/or discrete wire connections of suitable construction as known.

Referring now to FIGS. 10A-10D, an exemplary physical layout of pump PCB assembly 200 is shown, for purpose of illustration and not limitation. As shown for example in FIGS. 10A-10D, occlusion sensing PCB assembly 212, serial bus PCB assembly 214, haptic actuator 220 and button PCB assembly 224 each are joined to main controller circuit board 202 via rigid flex portions 204. For purpose of illustration, and not limitation, the exemplary physical layout of pump PCB assembly 200 can allow pump PCB assembly to be utilized in a relatively low-profile enclosure having a reduced footprint and thickness. For example, and as embodied herein, pump PCB assembly 200 can be assembled in an enclosure having a length within a range of 110 mm to 115 mm, a width within a range of 63 mm to 65.7 mm and a thickness within a range of 18.45 mm to 20 mm.

According to another aspect of the disclosed subject matter, and further to the aspects above, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a fluid drive component disposed proximate the receiving region, a display to provide visual feedback to the user, a plurality of input buttons disposed on the pump housing, a first processor coupled to the fluid drive component and the display and configured to reduce power to or otherwise hibernate the fluid drive component and the display when the pump is in an inactive state, and a second processor coupled to the first processor and the plurality of input buttons. The second processor is configured to provide an activation signal to the first processor when one or more of the plurality of input buttons is deployed.

Additionally or alternatively, the pump assembly can further include a radio-frequency identification (RFID) transceiver coupled to the first processor, and the first processor can be is configured to reduce power to the RFID transceiver when the pump is in the inactive state. The pump assembly can further include an occlusion sensor coupled to the first processor, and the first processor can be configured to reduce power to the occlusion sensor when the pump is in the inactive state.

Furthermore, and as embodied herein, the pump assembly can further include a serial bus coupled to the first processor, and the first processor can be configured to reduce power to the serial bus when the pump is in the inactive state. The pump assembly can further include a power supply voltage monitor coupled to the second processor, and the second processor can be configured to maintain the power supply voltage monitor in an active state when the first processor is powered down. The pump assembly can further include one or more memories, a primary power supply and a backup power supply coupled to the second processor, and the second processor can be configured to utilize the backup power supply to save present data to the one or more memories when the second processor detects the primary power supply is removed or disabled.

In addition, and as embodied herein, the pump assembly can further include a battery coulomb counter coupled to the second processor, and the second processor can be configured to maintain the battery coulomb counter in an active state when the first processor is powered down. The pump assembly can further include a speaker, and the first processor and the second processor each can be coupled to the speaker and configured to send an audio signal to the speaker when a fault is detected.

According to another aspect of the disclosed subject matter, a device for delivery of a beneficial agent to a user generally includes a cassette, a delivery tube and a pump. The cassette includes a cassette housing with a fluid reservoir defined therein. The cassette housing has a cassette base region. The delivery tube is fluidly coupled with the fluid reservoir. The pump includes a pump housing containing a pump assembly and has a receiving region to receive the cassette base region. The pump assembly includes a primary power source, a secondary power source coupled to the primary power source, a fluid drive component disposed proximate the receiving region and coupled to the primary power source isolated from the secondary power source, a first processor coupled to the primary power source and the secondary power source, a second processor coupled to the first processor, the primary power source and the secondary power source, one or more memories coupled to the first processor. At least one of the first processor and the second processor is configured, when the primary power source is removed or disabled, to utilize the secondary power source and the first processor to complete writing operations to the one or more memories prior to depletion of the secondary power source.

Additionally, and as embodied herein, the secondary power source can include a 1F capacitor. The secondary power source can be coupled to the primary power source via a secondary power source charger configured to charge the secondary power source when the primary power source is active. The one or more memories can include a nonvolatile memory storage.

Furthermore, and as embodied herein, the pump assembly can further include an RFID transceiver coupled to the secondary power source. The pump assembly can further include a speaker coupled to the secondary power source. The first processor and the second processor each can be coupled to the speaker, directly or via an audio amplifier, and configured to send an audio signal to the speaker when a fault is detected. The pump assembly can further include a display to provide visual feedback to the user. The display can be coupled to the primary power source and isolated from or otherwise not connected to the secondary power source. The pump assembly can further include an occlusion sensor coupled to the primary power source and isolated from the secondary power source.

Figure 11A:
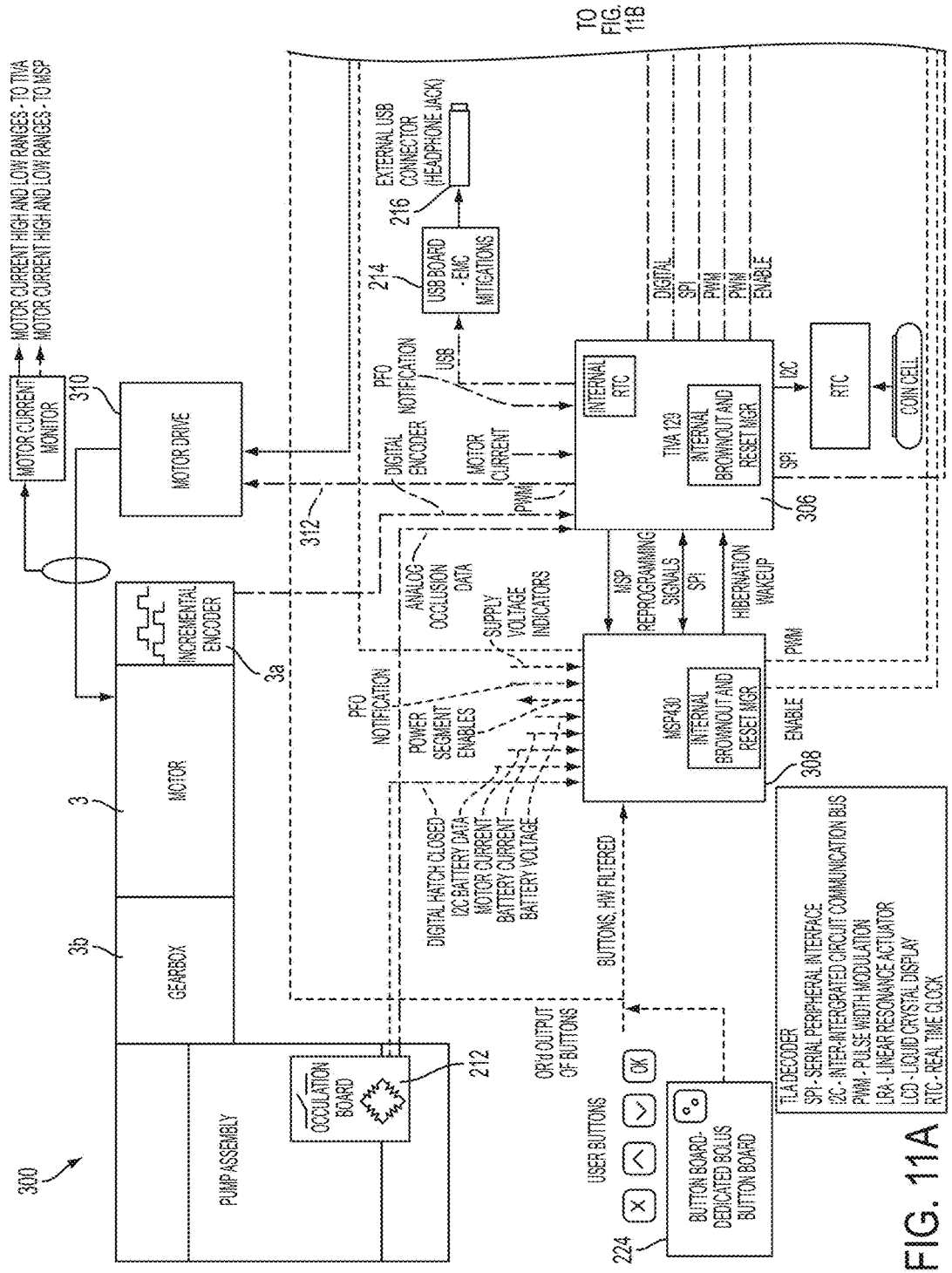
FIGS. 11A-11B together are a schematic diagram illustrating an exemplary delivery system for a beneficial agent delivery device according to the disclosed subject matter.
Figure 11B:
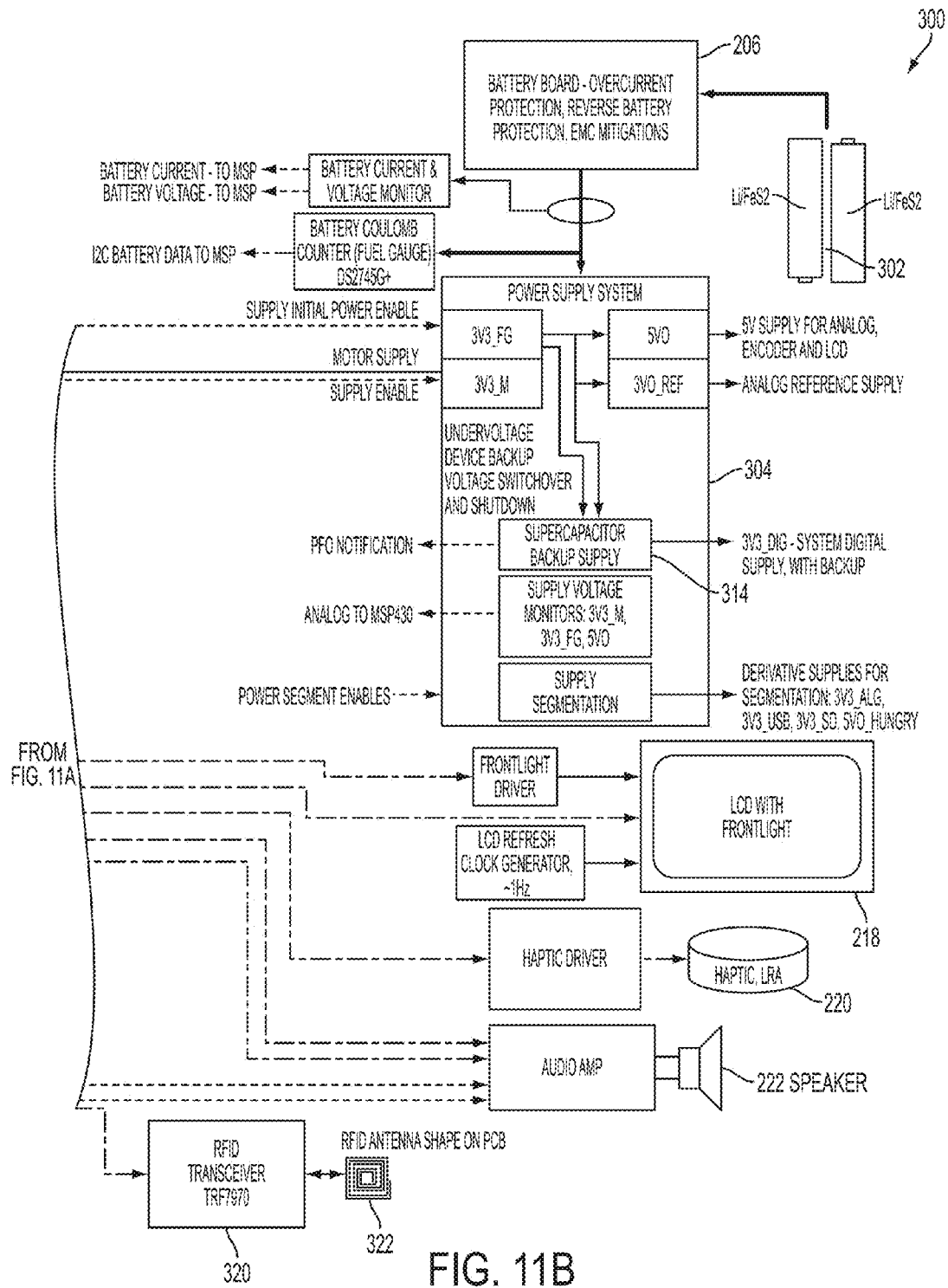

In accordance with these aspects, the pump assembly and related features as described above can be included individually or in combination. Referring now to FIGS. 11A-11B, a block diagram of an exemplary delivery system 300 is illustrated. For purpose of illustration and not limitation, a primary power source 302 provides power to the pump assembly 100. Primary power source 302 can be any suitable power source, and as embodied herein is a pair of series connected AA batteries. A power supply system 304 provides appropriate voltages for the digital and analog functions of the pump assembly 100. The power supply system 302 can include mitigations for electromagnetic compatibility (EMC) events and circuitry to allow for segmentation of the power supply system 304, which can improve battery life performance.

With reference to FIGS. 11A-11B, a system of processor components can provide overall control of the system. One of ordinary skill in the art will appreciate that any of the system can be implemented using one or more processors configured to perform the techniques described herein. For example, a software application can be stored on a non-transitory computer readable medium, such as a CD-ROM, DVD, Magnetic disk, ROM, RAM, or the like, the instructions of which can be read into a memory coupled to the one or more processors of the system. When executed, the software can instruct the processor to perform a particular function. As described herein below, for purposes of clarity, functionality of the system may be described generally, without recitation that one or more processor of the system is configured to perform the functionality. Alternatively, the system can be implemented in hard-wired circuitry in place of, or in combination with, software instructions for implementation of the presently disclosed subject matter. Thus, embodiments of the presently disclosed subject matter are not limited to any specific combination of hardware and software, provided such hardware and software are configured to perform the method as disclosed herein.

For purpose of illustration and not limitation, with reference to FIGS. 11A-11B, a first processor 306 can be configured to provide motor control and UI functions. For example, and as embodied herein, first processor 306 can be configured as an ARM-based processor, such as a Texas Instruments Tiva processor, or any other suitable processor. The first processor 306 can be configured to hibernate, i.e., to enter an inactive state for example to utilize less power when certain pump functions are not necessary or desired, and a second processor 308 can be configured to perform certain background tasks while first processor 306 hibernates. For example, and as embodied herein, second processor 308 can be configured as a mixed-signal microcontroller, such as a Texas Instruments MSP430, or any other suitable processor. Additionally, and as embodied herein, a number of sensing components can be operably coupled to the first processor 306 and/or second processor 308, for example and without limitation, to sense occlusion, battery voltage and current, and communicate with an RFID tag in a beneficial agent container, as discussed further herein.

For purpose of illustration and not limitation, as embodied herein, motor control system 300 includes a motor drive 310 configured to provide amplification of motor control output 312 from first processor 306 to drive motor 3, embodied herein as a brush DC motor coupled through a gearbox to the remainder of pump assembly 100. Feedback from encoder 3a can be conditioned, for purpose of illustration and not limitation in the motor drive block, to allow for closed loop control of motor velocity and position, as shown for example in FIGS. 11A-11B.

Additionally, as embodied herein, motor control system 300 can include a number of user interface (UI) components in communication with first processor 306 and/or second processor 308. UI components can include, for purpose of illustration and not limitation, display 218, embodied herein as an LCD display, speaker 222, embodied herein as a piezo ceramic speaker, and/or a haptic actuator 220, configured to provide visual, audible and tactile feedback to a user, as discussed further herein.

Figure 12A:
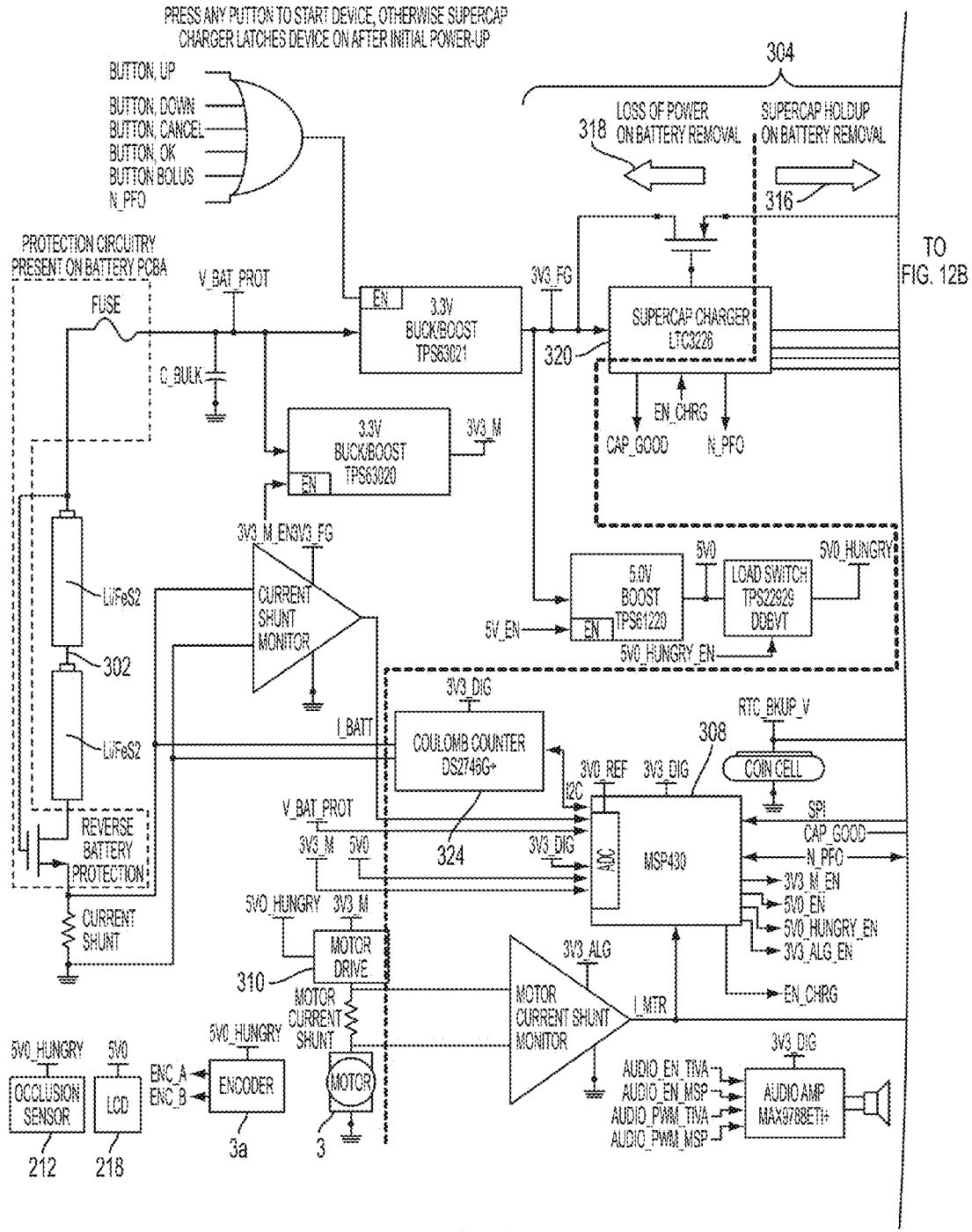
FIGS. 12A-12B together are a schematic diagram illustrating exemplary power distribution for the delivery system of FIGS. 11A-11B.
Figure 12B:
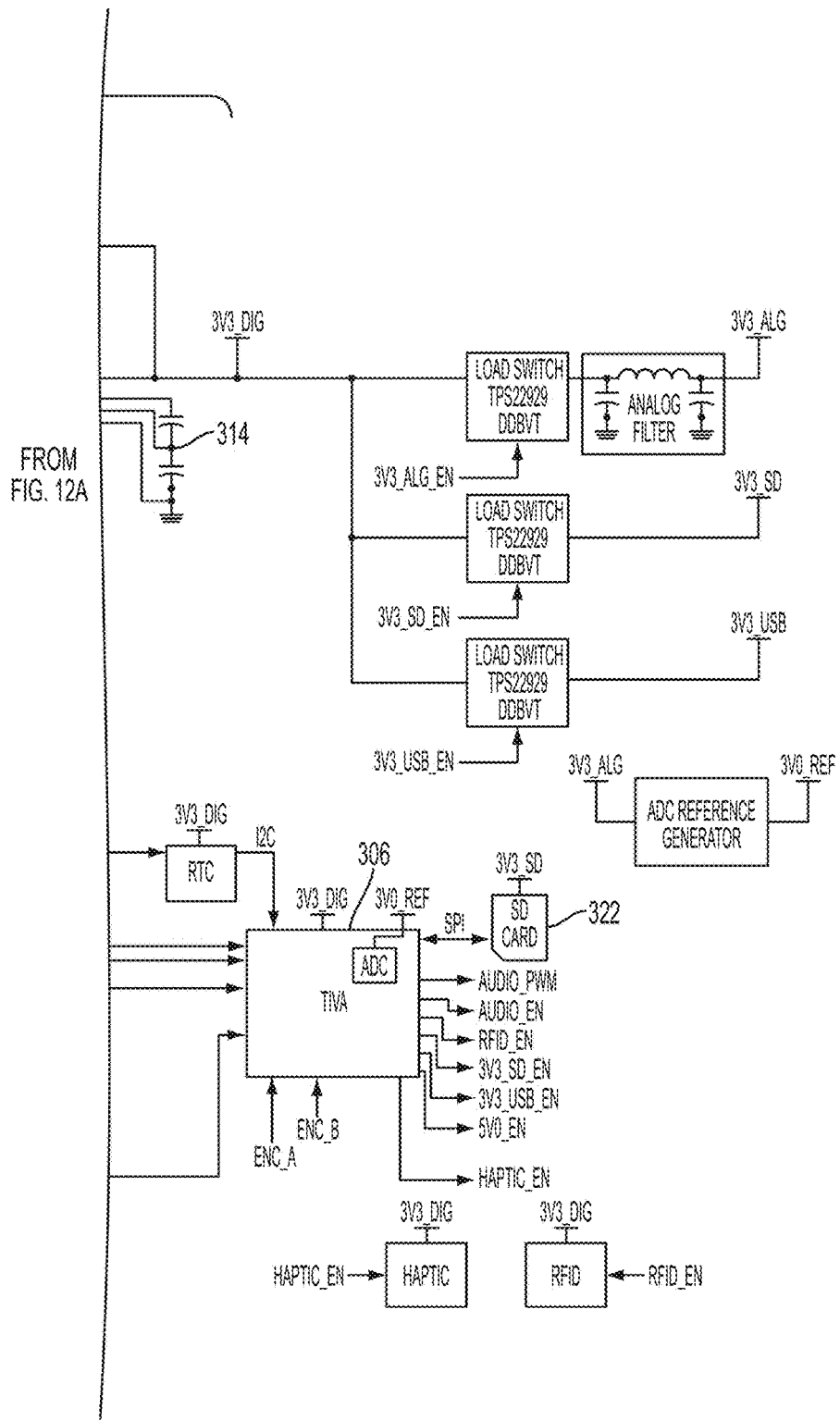

Referring now to FIGS. 12A-12B, an exemplary block diagram of a power supply system 304 is illustrated. For purpose of illustration and not limitation, as embodied herein, power supply system 304 includes a secondary power source 314. Secondary power source 314 can be any suitable power source, and as embodied herein is a pair of 1F capacitors. Power supply system 304 can be divided into two subsets of power supplies, for example and without limitation as illustrated by the dashed line of FIGS. 12A-12B, including a first power subset 316 (e.g., right of dashed line) configured to receive backup power from secondary power source 314 when primary power source 302 is removed or disabled, e.g., upon failure or depletion thereof, and a second power subset 318 (e.g., left of the dashed line) configured to lose power upon removal or disabling of primary power source 302.

For purpose of illustration and not limitation, as embodied herein, power supply system 304 can provide backup of digital hardware power supplies, for example and without limitation to allow for cleanup and user notification activities to complete upon removal or disabling of primary power source 302. A supercapacitor manager 320 can provide charging control, balancing, and protection to the secondary power source 314. For purpose of illustration, upon removal or disabling of primary power source 302, the supercapacitor manager can switch first power subset 316 to receive power from secondary power source 314. For example, can provide backup power to certain digital circuitry operating in a mid/high power state for a period of time until depletion of secondary power source 314, and as embodied herein, the period of time can be approximately 4 seconds. For example, and as embodied herein, power supply system 304 can provide backup power to a removable non-volatile memory storage 322, such as a secure digital memory card, to allow for storage of files on memory storage 322. As such, if primary power source 302 is removed or becomes disabled during a writing process to memory storage 322, sufficient time can be provided by secondary power source 314 to ensure internal processes of the memory storage 322 complete before secondary power source 314 fails. Additionally or alternatively, and as embodied herein, a Swissbit power fault tolerant SD card can be utilized in memory storage 322 to reduce or prevent hard failures of the filesystem in the event of removal or disabling of primary power source 302.

Additionally, and as embodied herein, power supply system 304 includes a number of power supplies to provide, for purpose of illustration and not limitation, appropriate voltage levels, references, and division of noisy and clean power. A first power path for the system can be derived from a first power supply 3V3_FG. As embodied herein, first power supply 3V3_FG can be implemented with a buck/boost low standby current supply to allow for primary power supply 302 input voltages between 1.8 and ~3.5V, which can represent a suitable range of input voltages provided by AA batteries, including without limitation, alkaline and Lithium Iron Disulfide cell batteries. First power supply 3V3_FG can supply power to, for example and without limitation, supercapacitor manager 320 and fuel gauging circuits, including a coulomb counter 324. Supercap manager 320 can provide a second power supply 3V3_DIG, which can represent a main power supply for all digital circuitry.

Power supply system 304 can include a third power supply 3V3_M, which can be a 3.3V power supply configured to provide noise isolation to motor drive 310. Third power supply 3V3_M can utilize a similar regulator as first power supply 3V3_FG, and as embodied herein, can be controlled by second processor 306 to allow independent shutdown of power supply to motor 3, for example and without limitation to prevent or mitigate uncommanded motor operation.

Additionally or alternatively, and as embodied herein, a fourth power supply 5V0 can be derived from first power supply 3V3_FG, and can be configured to provide power to, for purpose of illustration and not limitation, analog sensors and display 218, as discussed further herein.

Furthermore, and as embodied herein, a plurality of power segments can be included in one or more of the power supplies described herein. For example and without limitation, as embodied herein, the second power supply 3V3_DIG and fourth power supply 5V0 domains can each include a plurality of power segments to reduce or inhibit power used by individual peripherals. That is, certain peripherals of pump assembly 100 do not allow for appropriately low power consumption when disabled. Thus, such high loss peripherals can be segmented behind, for example and without limitation, load switches. Other peripherals, for example and without limitation peripherals having an acceptably low loss, can be attached to their "parent" power supply rail, e.g., first power supply 3V3_FG or fourth power supply 5V0, as appropriate, and controlled by an appropriate enable signal.

For example and not limitation, as embodied herein, power segments can include a first supply segment 3V3_SD for the memory storage 322 and second supply segment 3V3_USB for the serial bus 214 (shown for example in FIG. 11A), each implemented from second power supply 3V3_DIG. Additionally or alternatively, as embodied herein, a third supply segment 5V0_HUNGRY can be provided to power the encoder 3a and occlusion sensor 212, and can be implemented from fourth power supply 5V0, as shown for example in FIGS. 12A-12B.

In addition, and as embodied herein, motor 3 can be powered by motor drive 310, configured for example and as embodied herein as a single switch buck style motor drive. As embodied herein, motor inductance and back EMF can maintain supply currents to motor 3 within an acceptable level. As such, motor 3 can be prevented or inhibited from receiving a reversed supply voltage, for example and without limitation due to certain failures (e.g., short or open) of any parts of motor drive 310, thus preventing motor 3 from operating in reverse.

Figure 13:
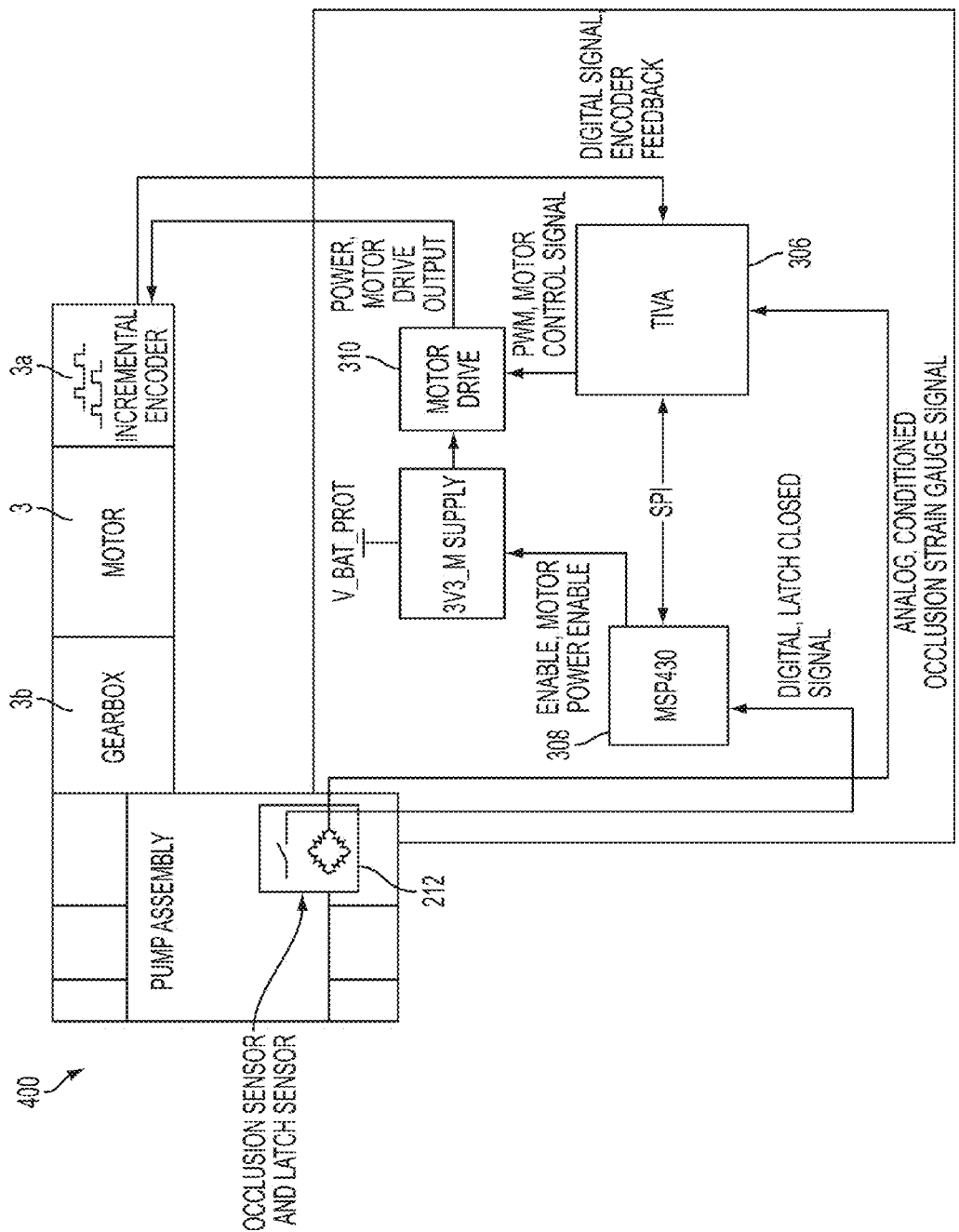
FIG. 13 is a schematic diagram illustrating exemplary fluid drive component controller portion of the delivery system of FIGS. 11A-11B.

Referring now to FIG. 13, an exemplary fluid drive control system 400 for pump assembly 100 is illustrated. As described further herein, as embodied herein, pump assembly 100 can be implemented as a linear peristaltic pump. Pump assembly 100 can include, as described herein, a motor 3 with encoder 3a and gearbox mated to the components interface with the peristaltic tube 223, including cam shaft 2 and finger plates 4. In operation, pump assembly 100 can urge fluid through a tubing system joined to peristaltic tube 223 by engaging peristaltic tube 223 in a linear fashion from inlet to outlet, which can provide an inherent pinch valve function preventing the fluid moving from outlet to inlet.

For purpose of illustration and not limitation, motor 3 can be any suitable motor 3, for example and embodied herein as a cordless DC brushed motor. The windings of motor 3 can be selected having a size suitable to provide a torque and speed profile to drive the linear peristaltic pump with the voltage provided by the two AA batteries. For example and without limitation, as embodied herein, motor 3 can include suitable windings to provide a nominal terminal inductance of about 0.0354 mH. In operation, motor 3 provides rotational energy suitable to move the cam shaft 2 and finger plates 4 to act upon the fluid in fluid communication with peristaltic tube 223.

Additionally, and as embodied herein, gearbox 3b can be disposed at the output of motor 3 and configured to translate torque provided from motor 3 to provide higher torque to cam shaft 2 at the expense of lower output speed. For purpose of illustration, and as embodied herein, gearbox 3b can have a gear ratio within a range between 67:1 and 131:1. Furthermore, and as embodied herein, bevel gears 6 can provide a 1:1 translation of torque and speed from the output of gearbox 3b to cam shaft 2. As such, motor 3 and gearbox 3b can be oriented 90 degrees relative to cam shaft 2 to allow these components to fit within the desired enclosure.

With continued reference to FIG. 13, as embodied herein, a motor control loop and motor drive signal can be implemented to utilize one or more processors. For purpose of illustration, and not limitation, as embodied herein, the motor control loop and motor drive signal each can be implemented to utilize first processor 306.

Figure 14:
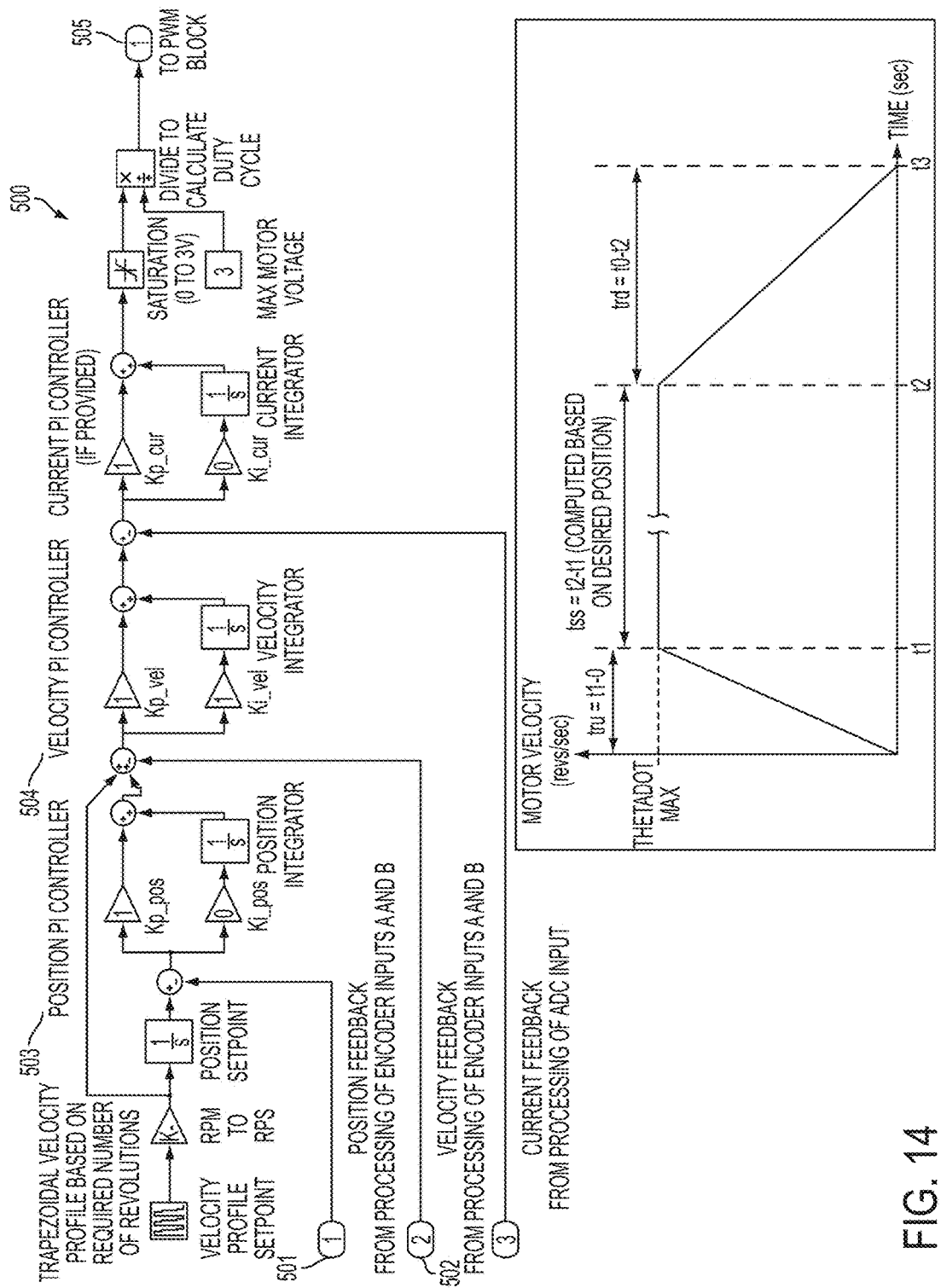
FIG. 14 is a schematic diagram illustrating exemplary techniques to control a fluid drive component for a beneficial agent delivery device according to the disclosed subject matter.

For example, and as embodied herein, an exemplary technique for a motor control loop 500 is illustrated in FIG. 14. Referring now to FIG. 14, in operation, motor control loop 500 can receive electrical pulses from encoder 3a as motor 3 rotates. The electrical pulses from encoder 3a can be analyzed by first processor 306 to determine a change of position, at 501, of motor 3 by counting a total number of pulses and to determine a velocity, at 502, by measuring an amount of time between pulses. The calculated position and velocity information can thus provide inputs to the motor control loop 500.

With continued reference to FIG. 14, for purpose of illustration and not limitation, as embodied herein, two proportional integration (PI) controllers can be utilized: a position PI controller 503 and a velocity PI controller 504. The calculated velocity can be input thereto. For example and not limitation, the input can be a trapezoid velocity profile, as illustrated herein. The present run duration and the present current position and velocity information can be updated based on the position feedback 501 and the velocity feedback 502 at regular intervals. For example and not limitation, as embodied herein, the regular intervals can be chosen as 1 millisecond. The present run duration can be compared to the determined run duration to determine whether the present run duration has exceeded the determined run duration. If the present run duration is exceeded, motor 3 can be stopped. A present position error can be calculated, which can be represented as a difference between the present run duration and the determined run duration. To continue driving the ramp up of the trapezoid profile, position PI controller can adjust for the position error to include the present position error, e.g., by decreasing the duration of the driving signal corresponding to the amount of the present run duration exceeding the determined run duration or by increasing the duration of the driving signal corresponding to the amount of the determined run duration that is less than the present run duration. Next the velocity error can be calculated, and the velocity PI controller can correct for the velocity error in a similar manner as the position error. The output from the velocity PI controller can be checked for saturation. The updated driving voltage can be outputted to the motor 3.

The inset of FIG. 14 shows an exemplary trapezoidal velocity profile. For purpose of illustration and not limitation, an exemplary calculation for the trapezoidal velocity profile for a volume setpoint VSP of 25 μL can be performed as follows. The volume per revolution RPUMP of the camshaft 2 of the pump assembly 100 can be a known constant based on camshaft design, for example and without limitation, as embodied herein 18 μL/rev. The gear ratio G between motor 3 and cam shaft 2 can also be a known constant based on the motor and pump design, for example and without limitation, embodied herein as chosen within a range of 67:1 to 131:1. The volume per revolution of the motor RMOTOR can be represented as RPUMP/G=0.280597015 μL/rev. The number of revolutions of the motor TSP to deliver the volume set point can be represented as VSP/RMOTOR. A maximum velocity TDMAX can be selected based on the motor specification, for example and without limitation, embodied herein as 55.8 rev/s. The ramp up time tRU and ramp down time tRD each can be chosen based on the motor, and can be the same or different, for example and as embodied herein, each can be 0.1 s. The time tSS during which the motor is supplied with normal operating voltage corresponding to the max velocity can be represented as tSS=(TSP/TDMAX)−0.5*(tRU+tRD). Accordingly, a smaller volume setpoint can correspond to a smaller tSS. For example and not limitation, a volume setpoint of 1 μL can have a smaller tSS than described above.

Furthermore, and as embodied herein, the output of the motor control loop 500, at 505, can provide a signal used to generate a pulse-width-modulation (PWM) signal for the motor drive 310. The PWM can provide a lower resultant voltage to motor 3 as a function of the PWM duty cycle. The motor speed can be proportional to voltage, so the motor speed (and as a result, position) can be changed based on PWM duty cycle. The duty cycle can be determined by the output of the motor control loop 500. In this manner, the PWM can provide a signal for the motor drive 310 to control the voltage being applied to the motor.

For purpose of illustration and not limitation, as embodied herein, motor drive 310 can be operated to apply an initial operating signal (e.g., a voltage or current) to motor 3. The initial operating signal can start the operation of the motor at a relatively low level, which can reduce or prevent strain on the motor 3 during activation. Motor drive 310 can be operated to increase a magnitude of the operating signal to the motor 3 up to a normal operating signal, which is greater than the initial operating signal. The magnitude of the operating signal can be increased, for example and without limitation, in a linear manner, a stepped manner with any number of steps between the initial operating signal and the normal operating signal, a gradual manner, an exponential manner, or any other suitable manner of increasing the operating signal from the initial operating signal to the normal operating signal.

In addition, and as embodied herein, motor drive 310 can receive the PWM signal provided from first processor 306 to control the operating signal applied to the motor 3. Motor drive 310, for purpose of illustration and not limitation, can be implemented as a power MOSFET, which can be controlled by the PWM signal and switch on/off the operating signal applied to motor 3. In this manner, motor drive 310 can convert battery energy to the desired operating signal for motor 3 to maintain suitable control of velocity and position of motor 3.

Motor 3 can be driven to operate the pump assembly 100 in a manner to improve battery life. For purpose of illustration and not limitation, as embodied herein, motor 3 can be operated in bursts at higher speed, compared to continuous operation at low speeds. As such, the motor 3 can operated at a cadence, e.g., by performing a pumping event at a selected time interval. A processor can control the motor assembly 3, as described herein. For example and not limitation, processor 306 can cause motor drive 310 to apply an increasing magnitude of operating signal (e.g., voltage or current) to motor 3 from an initial operating signal magnitude up to a normal operating signal magnitude, as described herein. Additionally, the processor can cause motor drive 310 to apply a decreasing magnitude of operating signal to motor 3 from the normal operating signal magnitude back down to the initial operating signal magnitude. The operating signal magnitude can be increased or decreased, for example and without limitation, in a linear manner, a stepped manner with any number of steps between the initial magnitude and the normal operating magnitude, a gradual manner, an exponential manner, or any other suitable manner, as described herein. For purpose of illustration and not limitation, as embodied herein, the applied signal magnitude can correspond to a trapezoidal velocity profile of the motor 3. Additionally, as described herein, processor 306 can control the motor assembly 3 based on various input and/or feedback signals. For example, the input and/or feedback signals can include the position, velocity, and/or current of the motor assembly 3, as described herein.

For example and not limitation, the selected time interval for the cadence can be any suitable time period, for example and without limitation, selected between 1-15 minutes. Any suitable technique can be utilized to determine the appropriate operating time for each time interval to achieve a desired flow rate. For example, and as embodied herein, a lookup table can be used to determine an operating time for each time interval to achieve a selected flow rate. Alternatively, the cadence or operating time can be calculated based on a formula or other suitable technique. For purpose of illustration and not limitation, a base packet size can be selected to correspond to a base amount of fluid to be dispensed. For example, the base packet size can be any suitable volume, such as 1 μL, 12.5 μL, or 25 μL. A lookup table can provide fluid amounts, which can correspond to integer multiples of the base packet size being delivered at a selected time interval, embodied herein as a 1-minute time interval. For illustration and not limitation, a flow rate of 0.1 ml/h corresponds to one 25 μL packet every 15 minutes during the hour, 0.2 ml/h corresponds to one packet every eight minutes plus one extra packet during the hour (e.g. at the last minute 0), 0.3 ml/h corresponds to one packet every five minutes, etc. For example and not limitation, a pumping cadence for a flow rate of 0.6 mL/hr can be calculated as follows. 0.6 ml·hr can be equivalent to 600 μL/hr. Assuming an exemplary packet size of 25 μL, 600/25=24 packets to be delivered to achieve the flow rate. 24 packets divided over 60 minutes yields 2.5 minutes per packet. Rounding to the nearest whole number results in 3 minutes per packet, which yields 20 packets over the hour. The remaining 4 packets divided over 60 minutes results in 15 minutes per packet. The resulting cadence therefore can be one packet every 3 minutes and one additional packet every 15 minutes.

Figure 15:
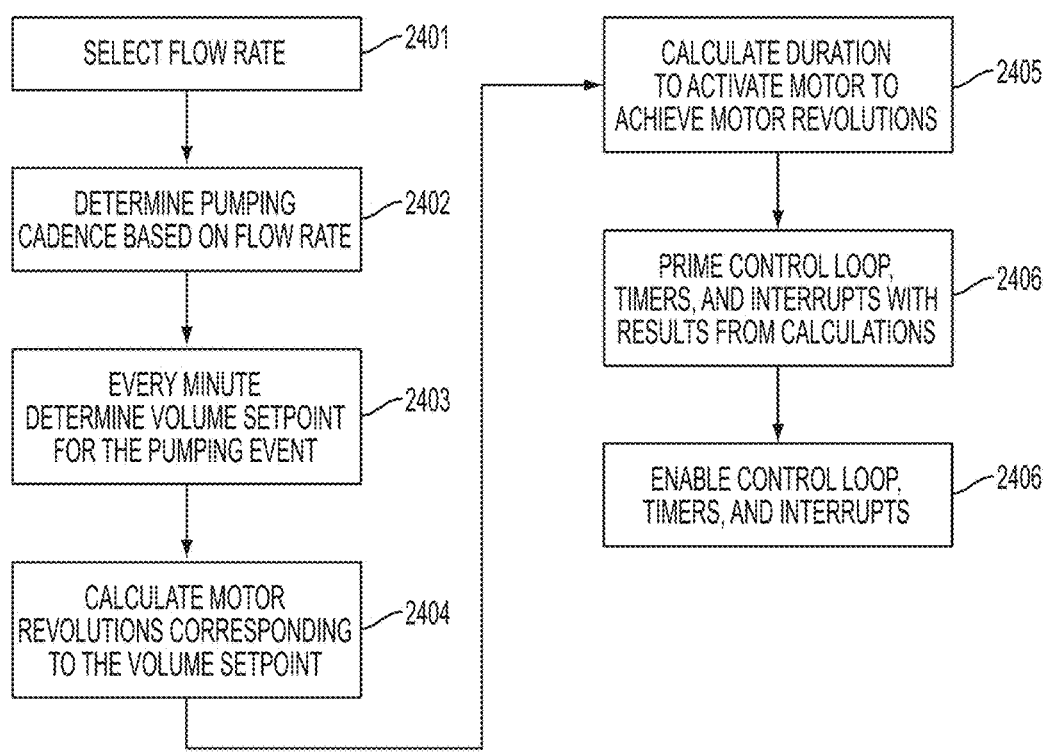
FIG. 15 is a flow chart illustrating an exemplary technique for delivering a beneficial agent to a patient according to the disclosed subject matter.

FIG. 15 is a diagram illustrating exemplary techniques for delivery of a beneficial agent to a user. At 2401, a flow rate is selected. Next, at 2402, a pumping cadence is determined based on flow rate. For example and not limitation, the pumping cadence can be calculated or can be determined from a lookup table accessible, as embodied herein by first processor 306, and additionally or alternatively by second processor 308. At 2403, a volume setpoint for a pumping event is determined for each time interval. For example, the volume setpoint can be calculated or looked up e.g., in a database or lookup table. At 2404, a number of motor revolutions corresponding to the volume setpoint can be calculated. For example, the number of motor revolutions can be determined from on a known ratio of revolutions to volume delivered. At 2405, a duration to activate the motor 3 to achieve motor revolutions can be calculated. For example, the duration for activating the motor 3 can be determined from a known motor velocity to achieve the number of determined motor revolutions. At 2406, the control loop, timers, and interrupts can be primed with results from the determined velocity and duration. Then at 2406, the control loop, timers, and interrupts can be enabled to activate the motor 3 at the determined velocity and duration. For each time interval, any suitable combination of the aforementioned events can be repeated to update the determined values for the time interval and to produce or adjust the motor control loop.

According to another aspect of the disclosed subject matter, and further to the above, a device for delivery of a beneficial agent to a user generally includes a cassette, a delivery tube, a pump, a lock member, and a contact force sensor. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component, the pump housing having a receiving region to receive the cassette base region, the fluid drive component disposed proximate the receiving region. The lock member is coupled to the pump housing and movable between an open position and a closed position, the cassette capable of being inserted into and removed from the receiving region when the lock member is in the open position, and the cassette being secured to the pump with the cassette base region within the receiving region and a length of the delivery tube in operative engagement with the fluid drive component when the lock member is in the closed position. The lock member includes a proximity tag configured to be disposed proximate the proximity sensor when the lock member is in the closed position. The contact force sensor is in communication with the delivery tube and arranged to measure a force or pressure in the delivery tube. The device further includes one or more processors in communication with the proximity sensor and the contact force sensor to receive a proximity signal and contact force data, respectively, therefrom, the one or more processors configured to determine whether the lock member is in the closed position using the proximity signal, determine whether the delivery tube is in operative engagement with the fluid drive component using the contact force data; and enable operation of the fluid drive component if the lock member is determined to be in the closed position and the delivery tube is determined to be in operative engagement with the fluid drive component.

Additionally, and as embodied herein, the proximity sensor can include a reed switch. The proximity tag can include a magnet. The one or more processors can be further configured to compare the contact force data to a threshold value, and determine the delivery tube is in operative engagement with the fluid drive component if the contact force data exceeds the threshold value. The one or more processors can be further configured to determine a local minimum force value detected by the contact force sensor during each revolution of each pumping cycle, and determine the delivery tube is in operative engagement with the fluid drive component if the local minimum force value exceeds the local maximum force value of a corresponding pump cycle by a local minimum threshold amount.

Furthermore, and as embodied herein, a cassette base region can include a RFID tag. The receiving region can include a RFID reader configured to read the RFID tag when the cassette is secured to the pump. The one or more processors can be further configured to receive identification information for the cassette encoded on the RFID tag from the RFID reader, determine whether the identification information is valid, and enable operation of the fluid drive component if the identification information is valid. The RFID tag can further include an expiration date of the beneficial agent, and the one or more processors can be further configured to receive the expiration date of the beneficial agent from the RFID reader, determine whether the expiration date is exceeded, and enable operation of the fluid drive component if the expiration date is not exceeded. The RFID tag can include high or ultra-high radio frequency ID.

According to another aspect of the disclosed subject matter, a device for delivery of a beneficial agent to a user generally includes a cassette, a delivery tube, a pump, a lock member, and a contact force sensor. The cassette includes a cassette housing with a fluid reservoir defined therein. The cassette housing has a cassette base region including a RFID tag. The delivery tube is fluidly coupled with the fluid reservoir. The pump includes a pump housing containing a pump assembly having a fluid drive component, a proximity sensor and a RFID reader, the pump housing having a receiving region to receive the cassette base region, the fluid drive component, proximity sensor and RFID reader disposed proximate the receiving region. The lock member is coupled to the pump housing and movable between an open position and a closed position, the cassette capable of being inserted into and removed from the receiving region when the lock member is in the open position, and the cassette being secured to the pump with the cassette base region within the receiving region and a length of the delivery tube in operative engagement with the fluid drive component when the lock member is in the closed position. The lock member includes a proximity tag configured to be disposed proximate the proximity sensor when the lock member is in the closed position. The contact force sensor is in communication with the delivery tube and arranged to measure a force or pressure in the delivery tube. The device further includes one or more processors in communication with the proximity sensor, the contact force sensor and the RFID reader to receive a proximity signal, contact force data and identification information for the cassette encoded on the RFID tag, respectively, therefrom, the one or more processors configured to determine whether the lock member is in the closed position using the proximity signal, determine whether the delivery tube is in operative engagement with the fluid drive component using the contact force data, determine whether the identification information is valid, and enable operation of the fluid drive component if the lock member is determined to be in the closed position, the delivery tube is determined to be in operative engagement with the fluid drive component, and the identification information is determined to be valid.

Furthermore, and as embodied herein, the one or more processors can be further configured to receive identification information for the cassette encoded on the RFID tag from the RFID reader, determine whether the identification information is valid, and enable operation of the fluid drive component if the identification information is valid. The RFID tag can further include an expiration date of the beneficial agent, and the one or more processors can be further configured to receive the expiration date of the beneficial agent from the RFID reader, determine whether the expiration date is exceeded, and enable operation of the fluid drive component if the expiration date is not exceeded. The RFID tag can include high or ultra-high radio frequency ID.

Each of these aspects can be combined with one or more of the various features of the apparatus and method described above. For purpose of illustration and not limitation, as embodied herein, pump assembly 100 can include one or more sensors to provide information regarding the operation of the pump. For example and without limitation, pump assembly 100 can include an occlusion sensor 90 (shown in FIG. 1B). As embodied herein, occlusion sensor 90 can include a Honeywell silicon strain gauge configured to measure a force of peristaltic tube 223 against occlusion block 9. Occlusion sensor 90 can be coupled to occlusion board 212 to provide force data received by occlusion sensor 90 to first processor 306, as shown for example in FIGS. 11A-11B. For purpose of illustration and not limitation, as embodied herein, occlusion board 212 can include an amplifier in line with occlusion sensor 90 to converts the output of occlusion sensor 90 to a single ended signal suitable for processing by first processor 306. As discussed further herein, first processor 306 can perform calculations using the output of occlusion board 212 during operation of the fluid drive component to determine whether an occlusion is present in a tubing system in communication with peristaltic tube 223, as discussed further herein.

Figures 2, 18A:
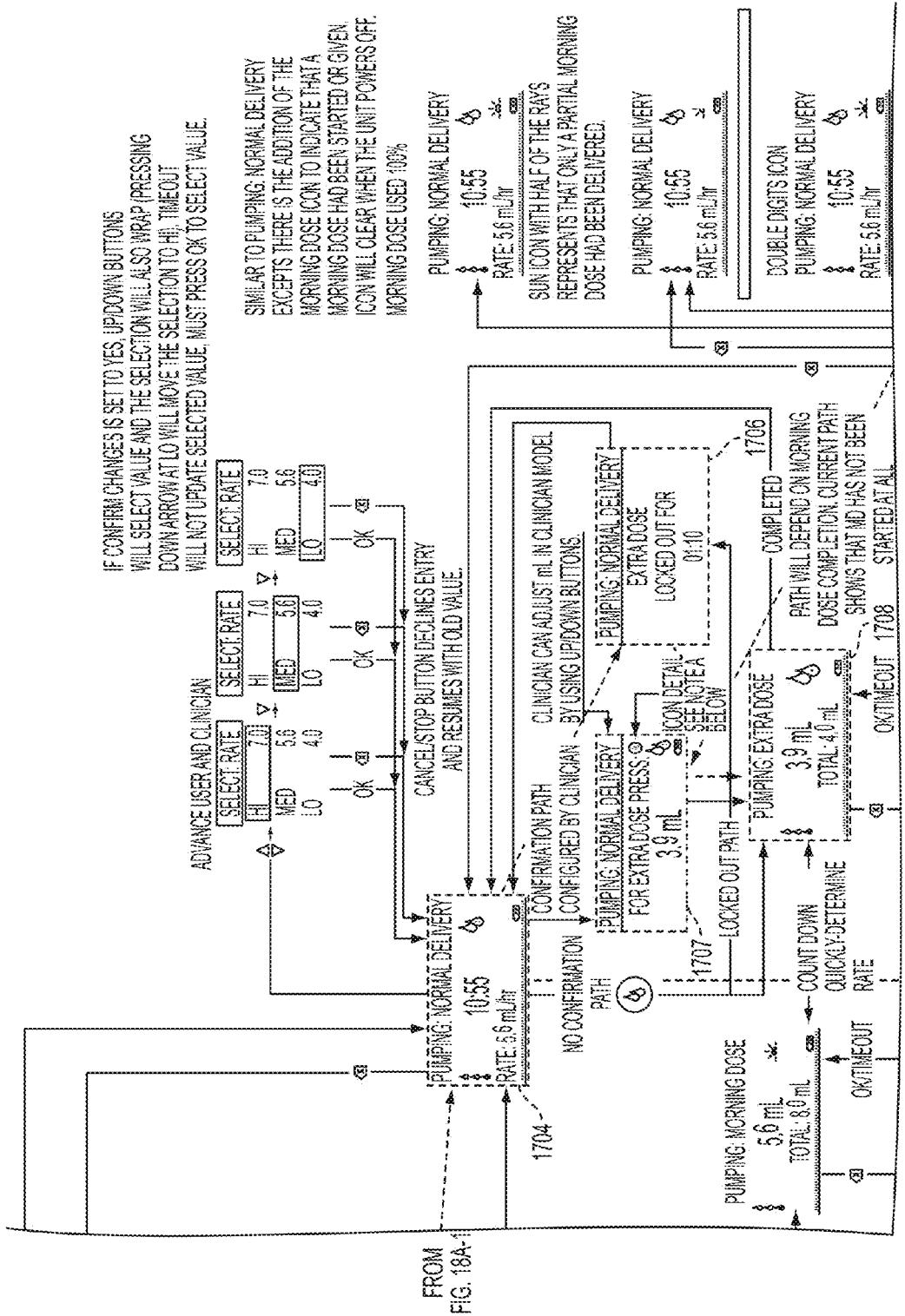
Figures 3, 18A:
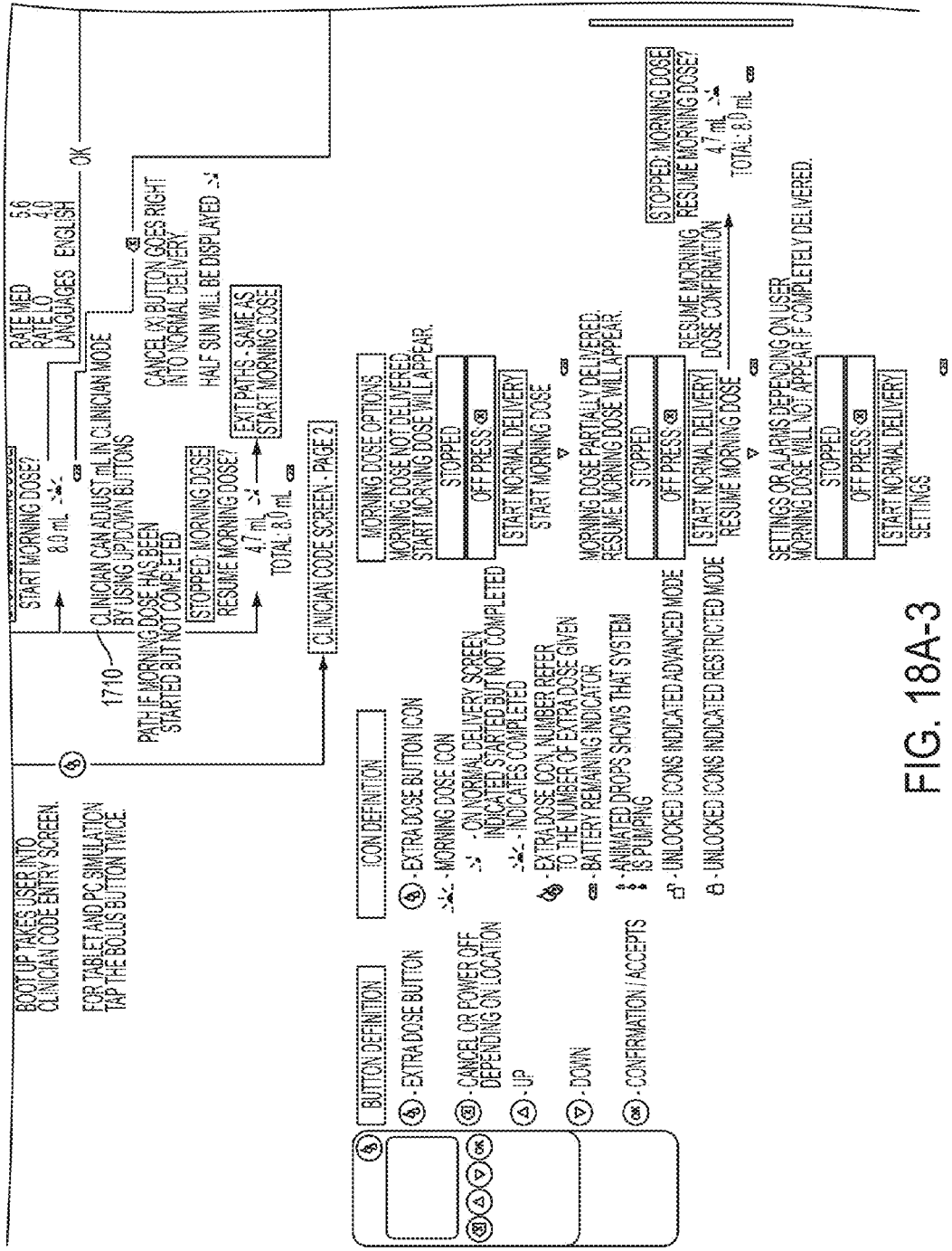
Figures 4, 18A:
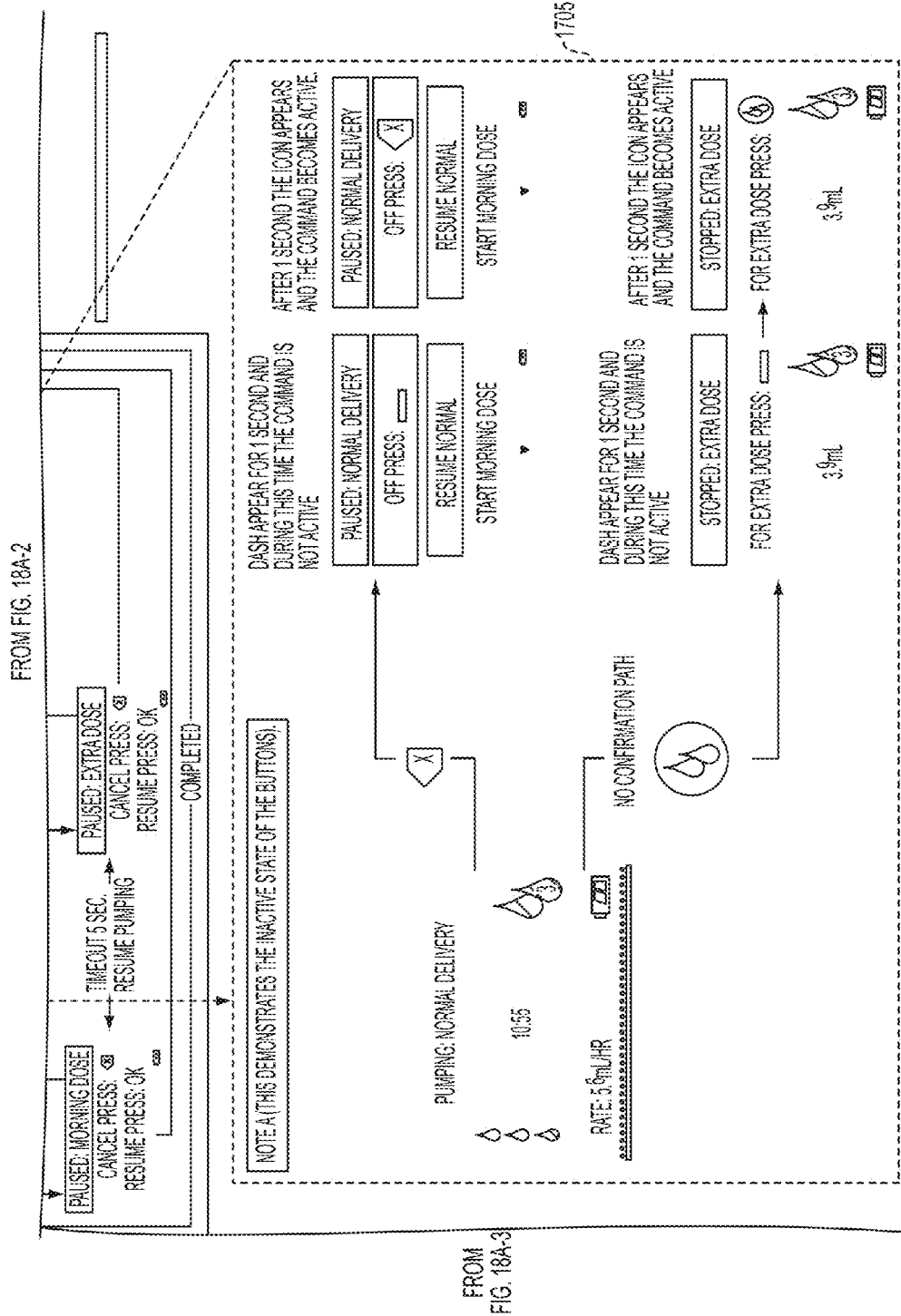
Figure 18B:
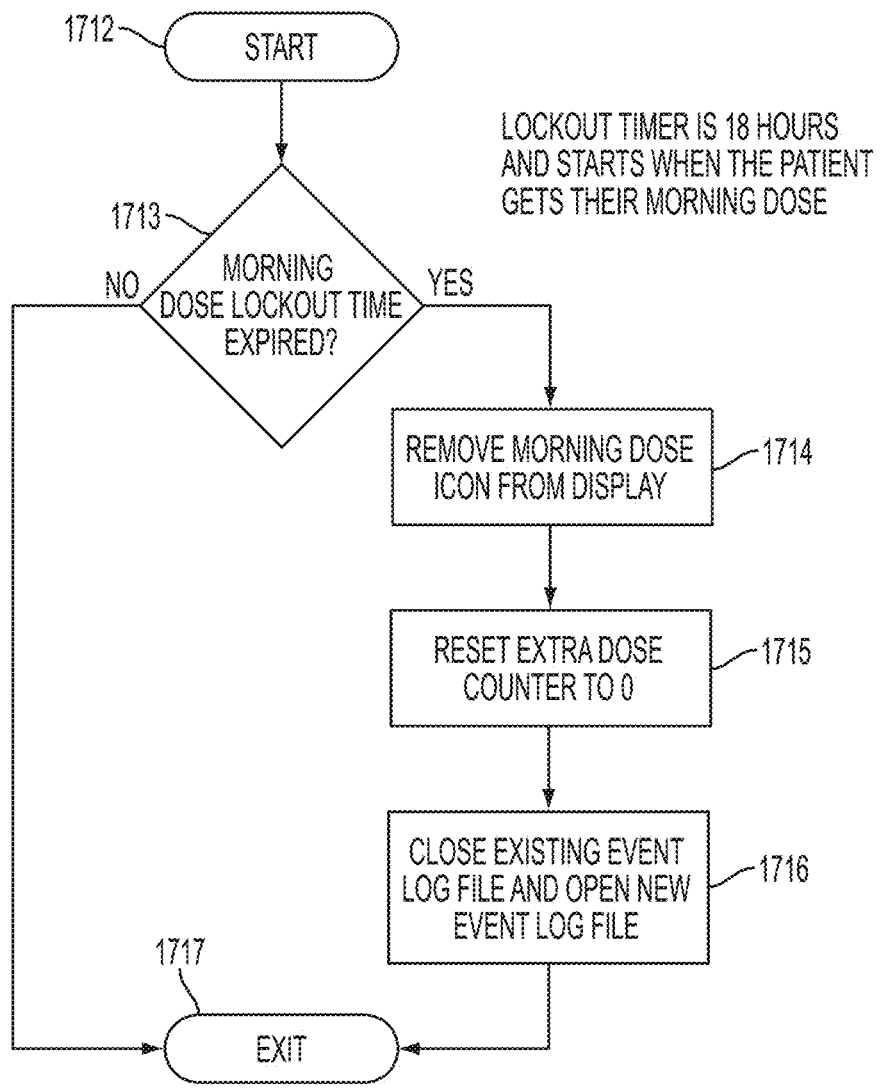
FIG. 18B is a flow chart illustrating exemplary techniques for providing a graphical user interface for a beneficial agent delivery device according to the disclosed subject matter.
Figures 1, 18C:
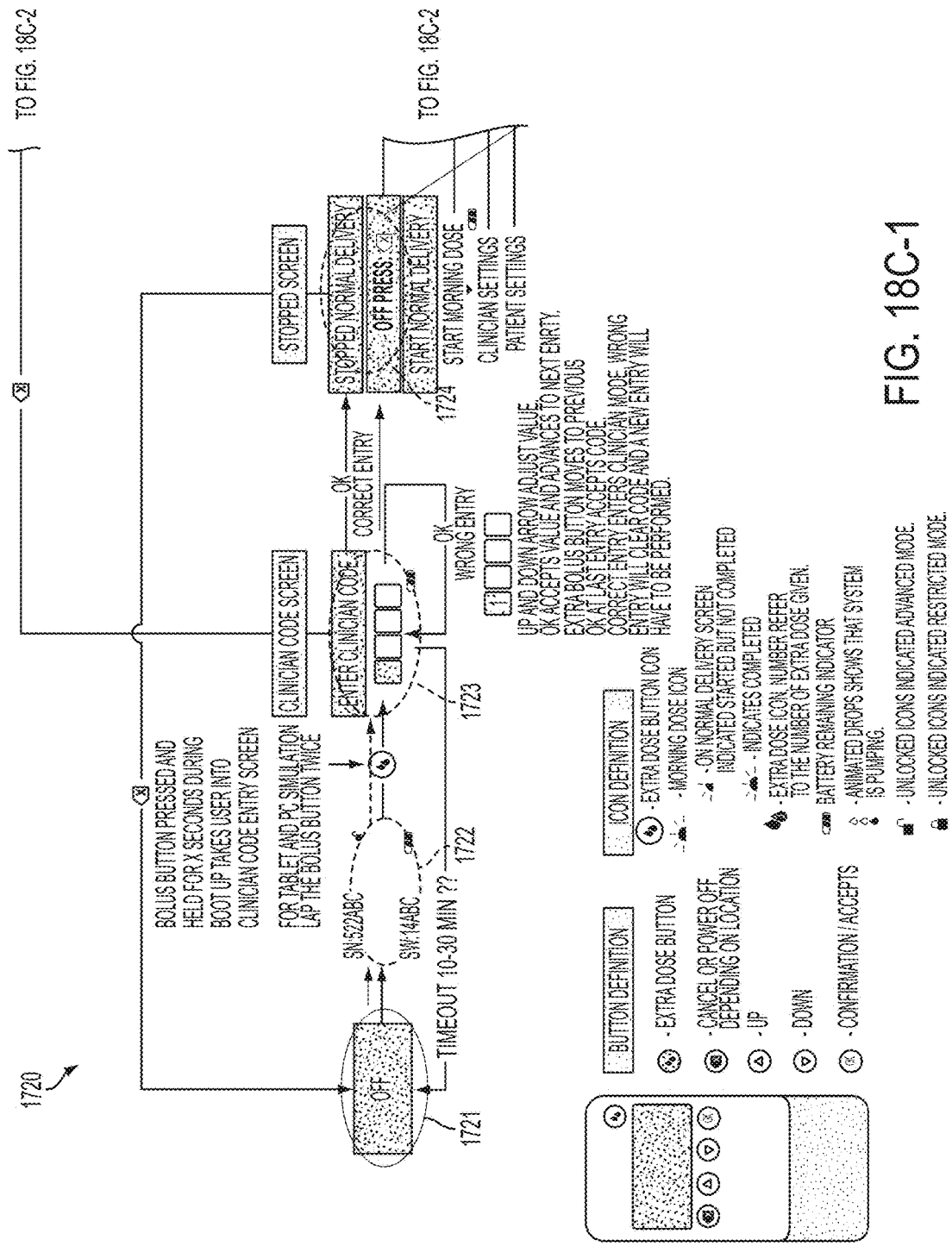
Figures 2, 18C:
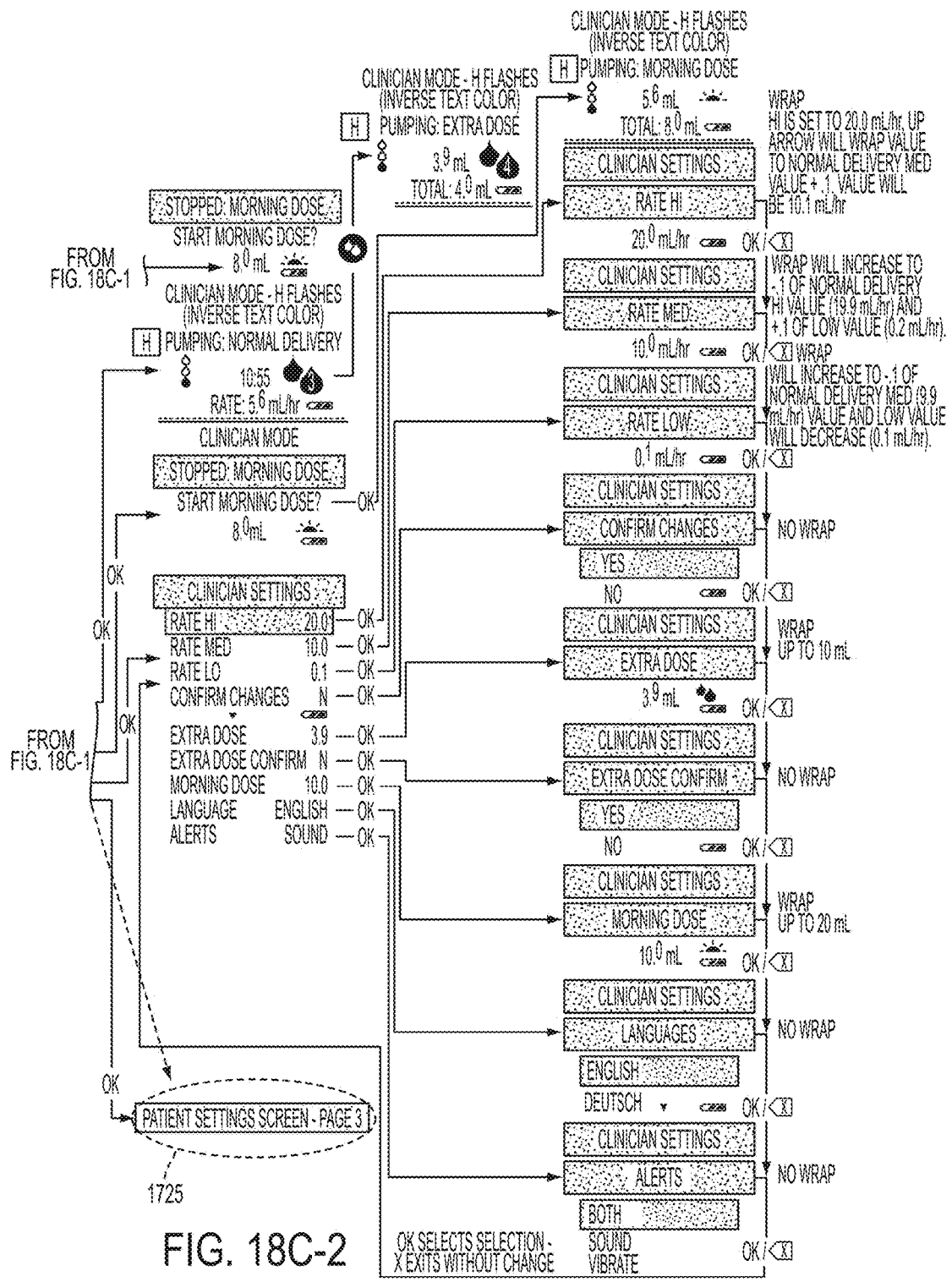
Figures 1, 18D:
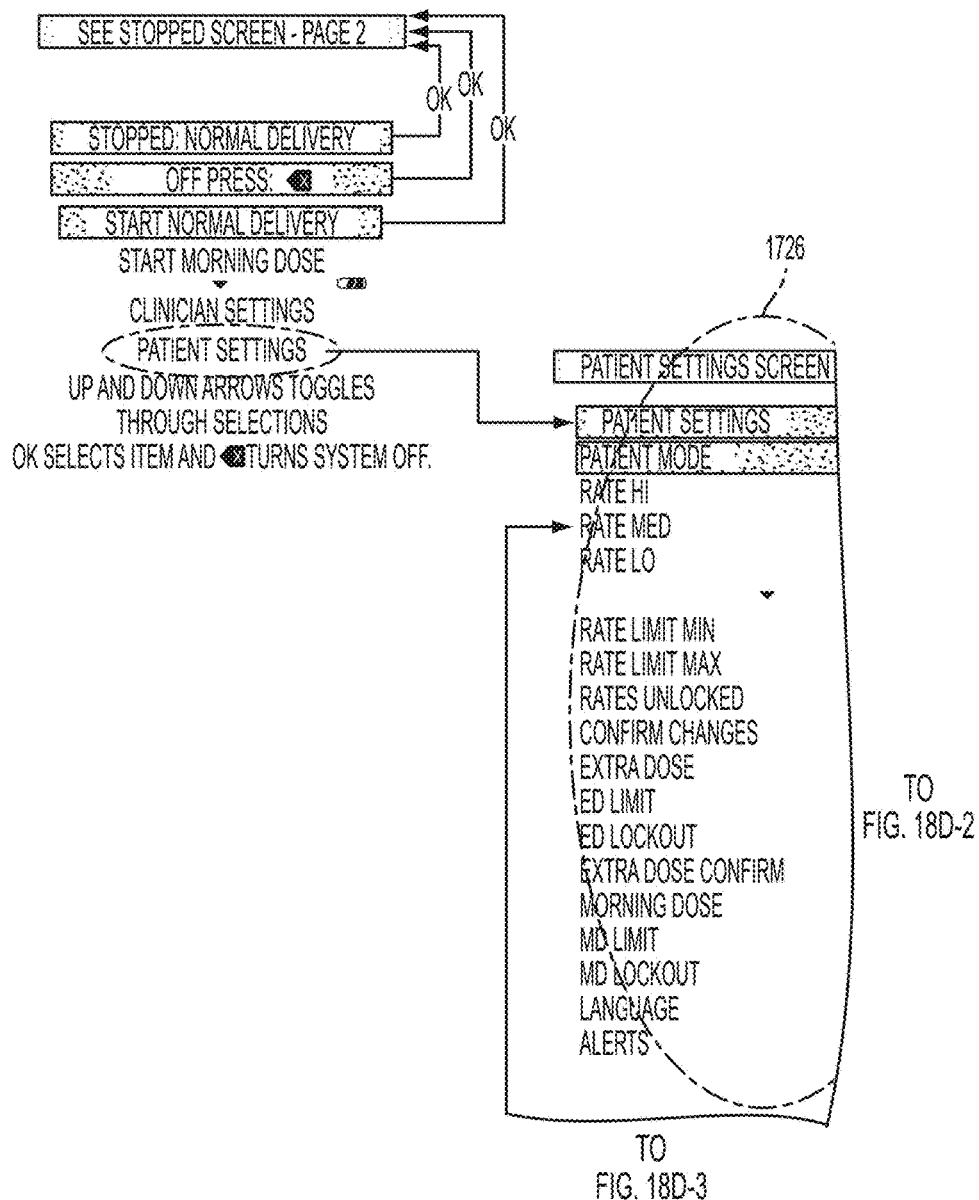
Figures 2, 18D:
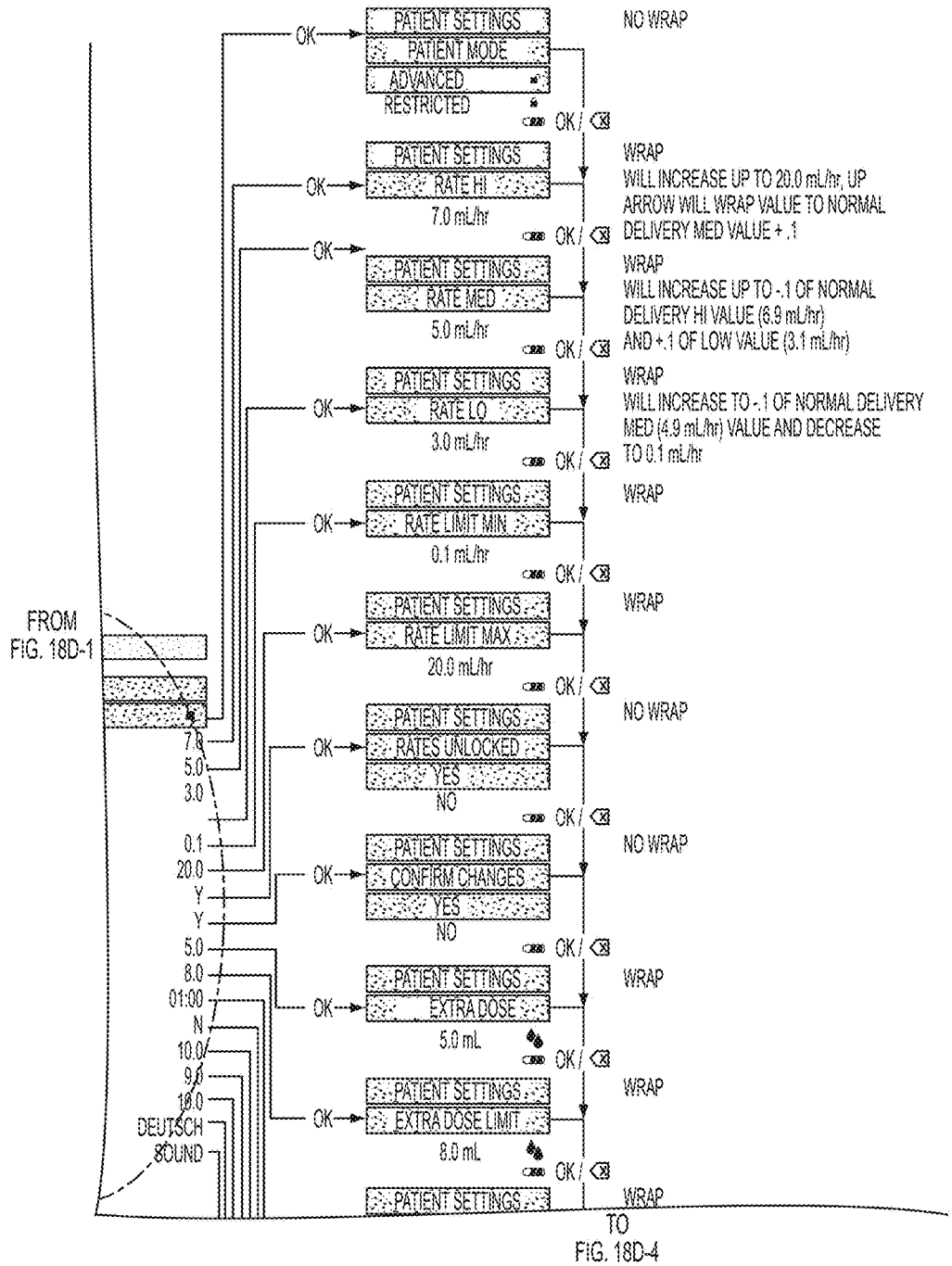
Figures 3, 18D:
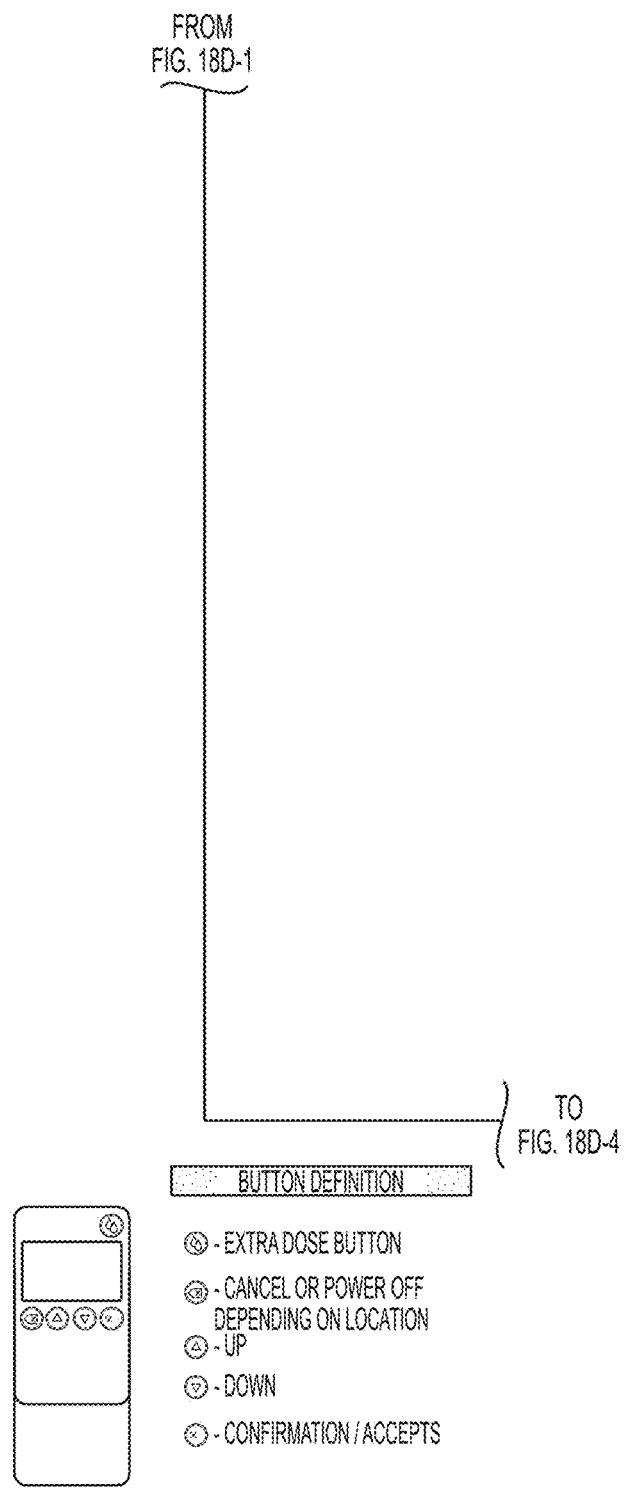
Figures 4, 18D:
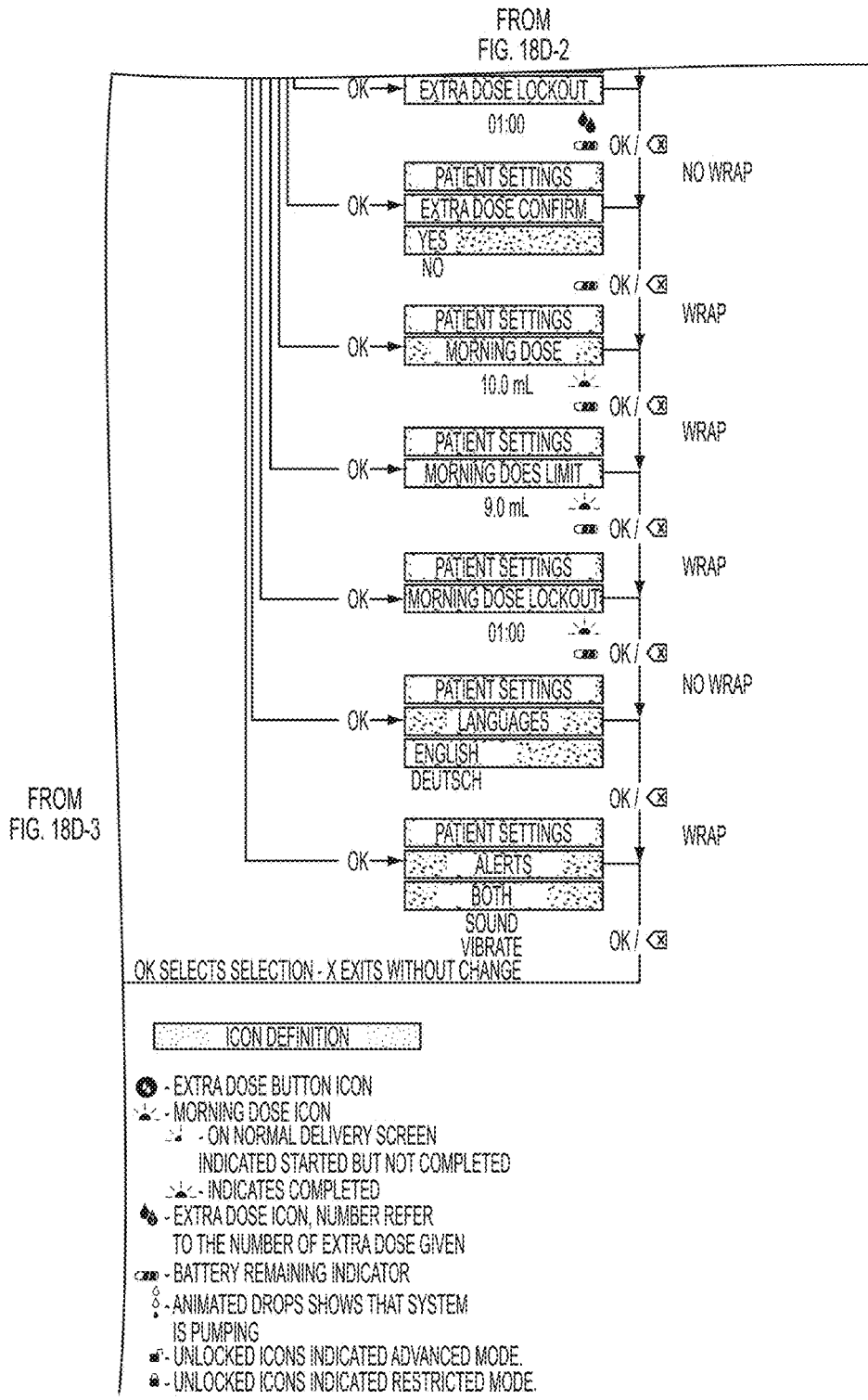

Additionally or alternatively, referring now to FIGS. 1, 2G and 2H, and as embodied herein, pump assembly 100 can include a proximity tag 22 disposed in recess 91 of lock member 11 to activate a proximity sensor 92 disposed proximate top cover 14. For purpose of illustration and not limitation, as embodied herein, the proximity sensor 92 can include a reed switch, and proximity tag 22 can include a magnet. As such, when the lock member 11 is in the closed position, proximity tag 22 can activate the proximity sensor 92 to send a signal to first processor 306 and/or second processor 308 that the lock member 11 is in the closed position indicating that occlusion block 9 is in operative engagement with peristaltic tube 223.

Additionally or alternatively, with reference to FIGS. 9 and 11A-11B, as embodied herein, pump assembly 100 can include an RFID reader 320 coupled to an RFID antenna 322 configured to read an RFID tag from a cassette joined to pump assembly 100. RFID reader 320 can be configured to identify drug cartridges and read information encoded in an RFID tag in a cassette joined to pump assembly 100. In this manner, the system can be used to deter counterfeiting drug cartridges. As embodied herein, RFID reader 320 can be coupled to first processor 306 to process data read by RFID reader 320.

For purpose of illustration and not limitation, the RFID tag can include identification information encoded thereon for a cassette joined to pump assembly 100. As embodied herein, identification information can include a serial number or other identification number. As such, and as embodied herein, first processor 306 can determine that the serial number or other identification number is a valid, for example using a checksum formula or any other suitable technique to validate an identification number. Additionally or alternatively, the RFID tag can include attribute information of a beneficial agent contained in the fluid reservoir encoded thereon, which can include, without limitation, a formation date and/or an expiration date of the beneficial agent. First processor 306 can thus compare the formation date and/or the expiration date of the beneficial agent to the present date to determine whether the beneficial agent is expired. First processor 306 can further validate the entire set of data from the RFID tag, which can include the identification information, if provided, attribute information, if provided, and any other information encoded on the RFID tag, and validation for the entire set of data can be formed, for example and without limitation, using a single checksum.

Figure 16A:
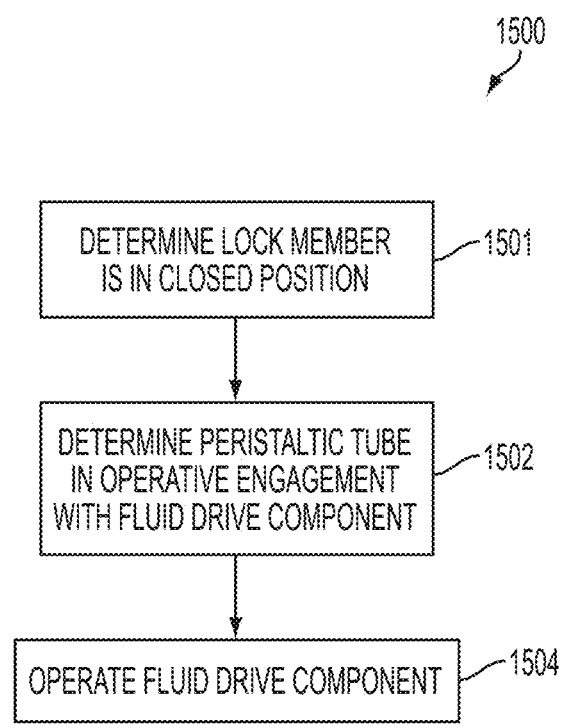
FIGS. 16A-16B each is a flow chart illustrating an exemplary technique for operating a beneficial agent delivery device according to the disclosed subject matter.
Figure 16B:
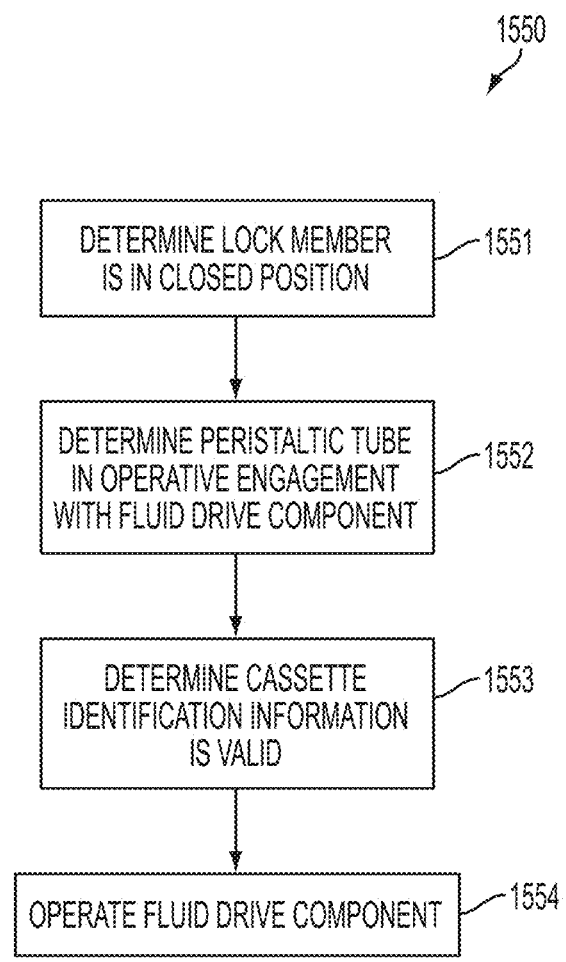

Referring now to FIGS. 16A-16B, one or more of the occlusion sensor 90, proximity tag 22 and RFID reader 320, if provided, can provide notification and confirmation of attachment of the cassette to the pump assembly 100. For purpose of illustration, and not limitation, as shown for example in FIG. 16A, an exemplary technique 1500 for activating a device to deliver a beneficial agent for a user is provided. At 1501, pump assembly 100 can determine whether lock member 11 is in the closed position, for example and as embodied herein using proximity tag 22 and the proximity sensor 92 as described herein. At 1502, pump assembly 100 can determine whether peristaltic tube 223 is in operative engagement with occlusion block 9 of the pump assembly 100, for example and as embodied herein using occlusion sensor 90. That is, for purpose of illustration and not limitation, first processor 306 can compare force data received from occlusion sensor 90, as described above, to a threshold. For purpose of illustration and not limitation, and as embodied herein, force data can be received from occlusion sensor 90 in units referred to herein as "counts," which can be a magnitude of a discrete or continuous signal over time corresponding to a magnitude of force against occlusion sensor 90. As embodied herein, the threshold can be within a range of 150 counts to 2500 counts, which can represent a force greater than 0 and less than or equal to the force applied by the peristaltic tube 223 to the occlusion block 9 when in operative engagement therewith. At 1504, if the lock member is determined to be in the closed position and the peristaltic tube 223 is determined to be in operative engagement with occlusion block 9, pump assembly 100 can activate motor drive 310 to drive motor 3, as described herein.

For purpose of illustration, and not limitation, as shown for example in FIG. 16B, another exemplary technique 1550 for activating a device to deliver a beneficial agent for a user is provided. At 1551, pump assembly 100 can determine whether lock member 11 is in the closed position, for example and as embodied herein using proximity tag 22 and the proximity sensor 92 as described herein. At 1552, pump assembly 100 can determine whether peristaltic tube 223 is in operative engagement with occlusion block 9 of the pump assembly 100, for example and as embodied herein using occlusion sensor 90, as described herein. At 1553, cassette identification information can be read by RFID sensor 320, if provided, and first processor 306 can determine whether the cassette identification information is valid, as described herein. At 1554, if the lock member is determined to be in the closed position, the peristaltic tube 223 is determined to be in operative engagement with occlusion block 9, and the cassette identification information is determined to be valid, pump assembly 100 can activate motor drive 310 to drive motor 3, as described herein.

According to another aspect of the disclosed subject matter, and further to the above, a device for delivery of a beneficial agent to a user generally includes a cassette, a delivery tube, a pump and a contact force sensor. The cassette includes a cassette housing with a fluid reservoir defined therein. The cassette housing has a cassette base region. The delivery tube is fluidly coupled with the fluid reservoir. The pump includes a pump housing containing a pump assembly having a fluid drive component, the pump housing having a receiving region to receive the cassette base region, the fluid drive component disposed proximate the receiving region. The contact force sensor is in communication, such as by direct or indirect contact, with the delivery tube and arranged to measure a force or pressure in the delivery tube. The device includes one or more processors in communication with the contact force sensor to receive data representing the measured force or pressure from the contact force sensor, the one or more processors configured to determine a maximum force value detected by the contact force sensor during an initial pumping cycle, the maximum force value corresponding to a baseline maximum force value, obtain subsequent force values from the contact force sensor during each subsequent pumping cycle, and determine an occlusion is present if one or more of the subsequent force values exceed the baseline maximum force value by a threshold amount.

Additionally, and as embodied herein, the one or more processors can be further configured to determine a subsequent maximum force value during the subsequent pumping cycle, and adjust the baseline maximum force value to the subsequent maximum force value if the subsequent maximum force value is less than the baseline maximum force value. The threshold amount can be about 10% of the baseline maximum force value.

Furthermore, and as embodied herein, the one or more processors can be further configured to determine a local maximum force value during an initial pump revolution of each pump cycle, the local maximum force corresponding to a baseline local maximum force value, obtain a subsequent local force maximum during each subsequent pump revolution of each pump cycle, and determine an occlusion is present if one or more of the subsequent local force maxima exceeds the baseline local maximum force value by a local threshold amount. The local threshold amount can be about 13% of the baseline local maximum force value. The one or more processors can be further configured to determine the local maximum force value of each pump cycle when a flow rate of the fluid drive component is above a threshold flow rate. The threshold flow rate can be 10 mL/hr.

Furthermore, and as embodied herein, the one or more processors can be further configured to determine a local minimum force value detected by the contact force sensor during each revolution of each pumping cycle, and determine an error is present if the local minimum force value does not exceed the local maximum force value of a corresponding pump cycle by a local minimum threshold amount. The error can include a mechanical failure of the fluid drive component. The error can include an occlusion signal circuitry failure. A duration of each pumping cycle can be determined at least in part by a flow rate of the fluid drive component.

In addition, and as embodied herein, the device can further include a motor operatively coupled to the fluid drive component, and a rotational position sensor operatively coupled to the motor to determine a rotational position of the motor. The one or more processors can be further operatively coupled to the rotational position sensor, and the one or more processors can be further configured to determine each pump revolution from the rotational position sensor. The one or more processors can be further configured to stop the fluid drive component when the occlusion is determined to be present. The device can further include a display operatively coupled to the one or more processors, and the one or more processors can be further configured to display an error signal on the display when the occlusion is determined to be present. The contact force sensor can include a single contact force sensor. The one or more processors can be further configured to apply a four-sample moving average filter to the data representing the measured force or pressure from the contact force sensor.

These aspects can be combined with one or more features of the apparatus and method described above. Furthermore, and for purpose of illustration and not limitation, as described herein, techniques for occlusion sensing can use occlusion sensor 90 to measure a force of peristaltic tube 223 against occlusion block 9. Occlusion sensor 90 can be coupled to occlusion board 212 to provide force data received by occlusion sensor 90 to first processor 306, as shown for example in FIGS. 11A-11B. For purpose of illustration and not limitation, occlusion sensor 90 can include a contact force sensor, for example and embodied herein as a strain gauge, mounted directly onto pump base block 1 to contact the peristaltic tubing proximate the outlet side of the tubing at or near occlusion block 9. Such a location can allow the sensor to monitor occlusions in a tubing system disposed between pump assembly 100 and the patient. Furthermore, and as embodied herein, first processor 306 can perform averaging on data received from occlusion sensor 90, for example and without limitation to reduce data spikes or other anomalies due to noise. As embodied herein, four-sample moving average filtering can be performed on the data.

For purpose of illustration and not limitation, and as embodied herein, exemplary techniques for occlusion sensing can include a one or more threshold checks. A difference between a nominal pumping pressure and the occlusion pressure can be affected by loading variability, the viscosity of the drug, and the pump cadence (e g running at higher pump speeds for shorter durations), which can contribute to increases in the peak pressures of the pump pulses. Occlusion sensing techniques can also be utilized to detect and prevent or inhibit pressure in the tubing system from exceeding a threshold pressure for an extended period of time. Additionally, and as embodied herein, a plurality of sensing techniques can be performed in parallel using the same data from a single occlusion sensor, which can be referred to as a "layered" approach. Alternatively, a single technique for occlusion sensing can be performed. As a further alternative, a plurality of sensing techniques using a plurality of occlusion sensors can be performed, either sequentially or in parallel.

Additionally, and as embodied herein, exemplary techniques for occlusion sensing can analyze an occlusion sensor 90 force magnitude, referred to herein as "counts," at various points in a given pumping cycle and/or can analyze occlusion sensor force data prior to the pump assembly 100 activating for starts for a subsequent pumping cycle. Exemplary techniques for occlusion can examine a difference between occlusion pump counts, and determine whether an occlusion is present, as described herein. For example and without limitation, if the difference between two counts is outside of a predetermined window or threshold, the pump assembly 100 can determine an occlusion to be present. For purpose of illustration and not limitation, as embodied herein, the predetermined window or threshold can be within a range of 81 counts to 138 counts, which can vary based at least in part on the present flow rate of the pump.

Furthermore, and as embodied herein, pressure peaks can be sensed, an initial variability can be adjusted for, and other non-occlusion events can be accounted for. Force against the wall of peristaltic tube 223 or pressure within the peristaltic tube 223 can be measured after the pump assembly 100 turns off and a force delta can be calculated after measuring the force when the pump assembly 100 turns back on for the next cadence. For purpose of illustration and not limitation, the delta can be large during normal pump operation at least in part because the internal pressure of the tubing can decay when the pump is off. During an occlusion, the delta can be measurably smaller, at least in part because there can be little or no pressure decay. When an occlusion is detected, the pump assembly 100 can be shut off (e.g. by terminating voltage supply to the motor 3). Additionally, the user can be notified, for example, by a screen prompt or an audio alarm.

Figure 17A:
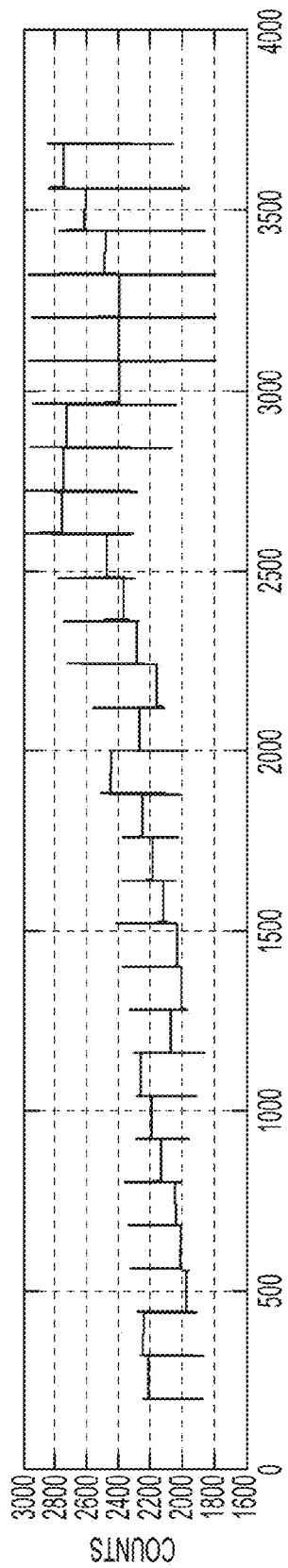
Figure 17B:
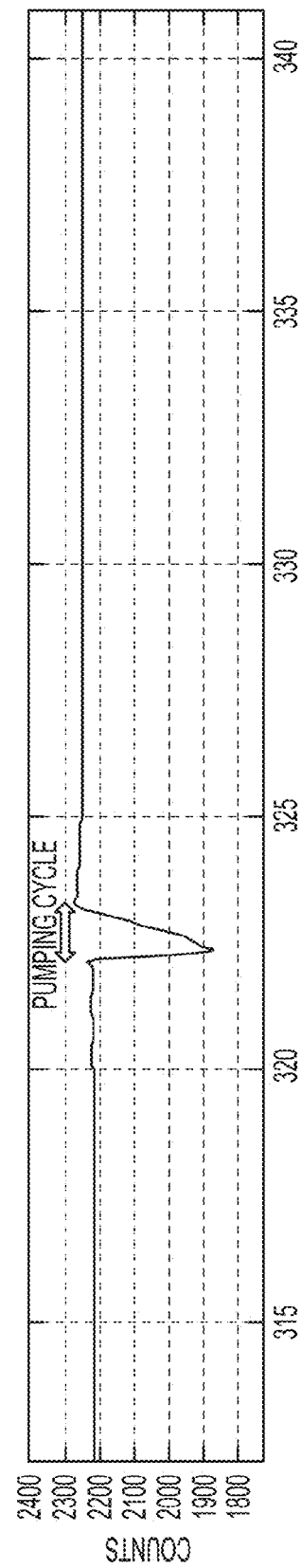
Figure 17C:
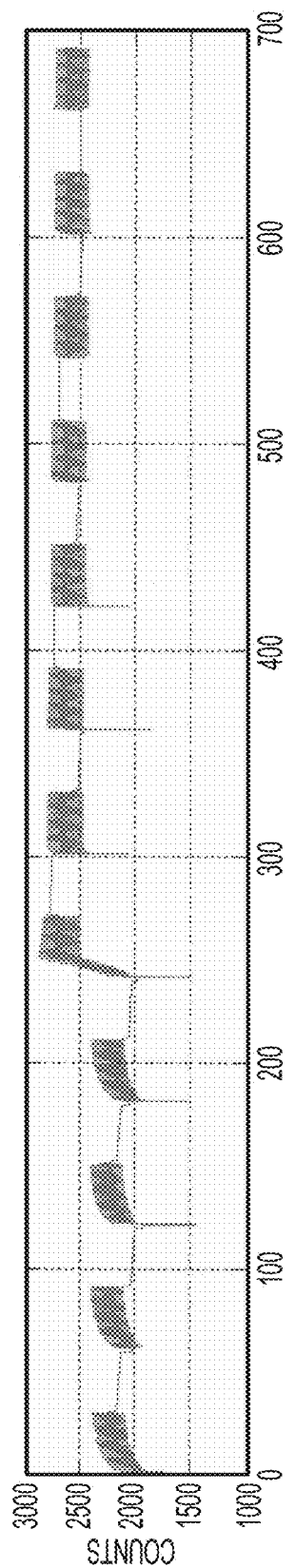
Figure 17D:
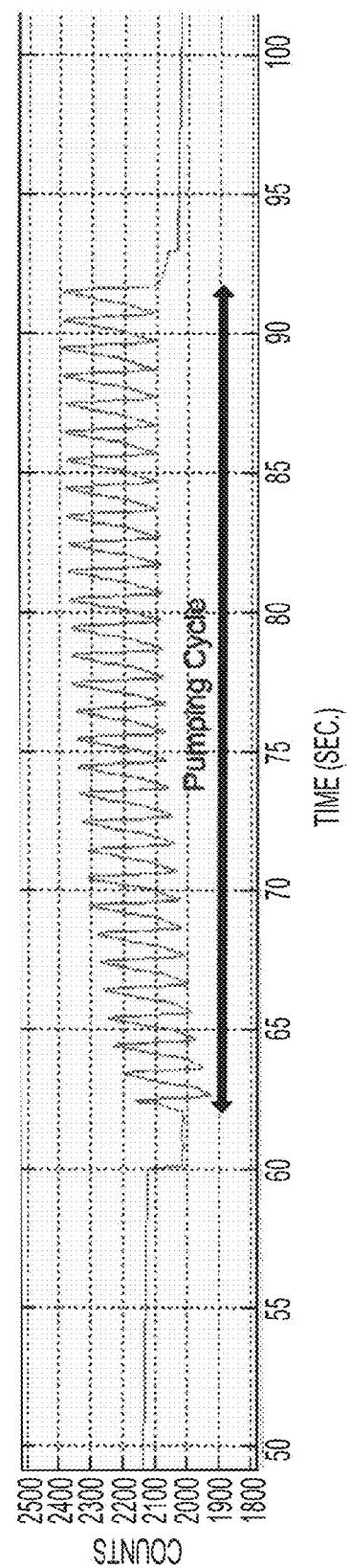

As embodied herein, a pumping cycle can refer to a portion of time during which pump assembly 100 is delivering a beneficial agent. Referring now to FIGS. 17A-17M, exemplary techniques for occlusion sensing are illustrated. FIG. 17A is a diagram illustrating exemplary occlusion sensor counts over time for pump assembly 100 operating at a 1 mL/hr flow rate, with an occlusion introduced into the system at about 1500 seconds. FIG. 17B illustrates a zoomed-in portion of the time scale of the diagram of FIG. 17A. As shown for example in FIG. 17B, an exemplary pumping cycle is illustrated between about 322 seconds and 323 seconds on the time scale. For purpose of illustration and comparison, FIG. 17C is a diagram illustrating exemplary occlusion sensor counts over time at a 40 mL/hr flow rate, with an occlusion introduced into the system at about 250 seconds. FIG. 17D illustrates a detailed portion of the time scale of the diagram of FIG. 17C. As shown for example in FIG. 17D, an exemplary pumping cycle is illustrated between about 62 seconds and 92 seconds on the time scale. As such, the duration of a pumping cycle can increase as flow rate increases.

Figure 17E:
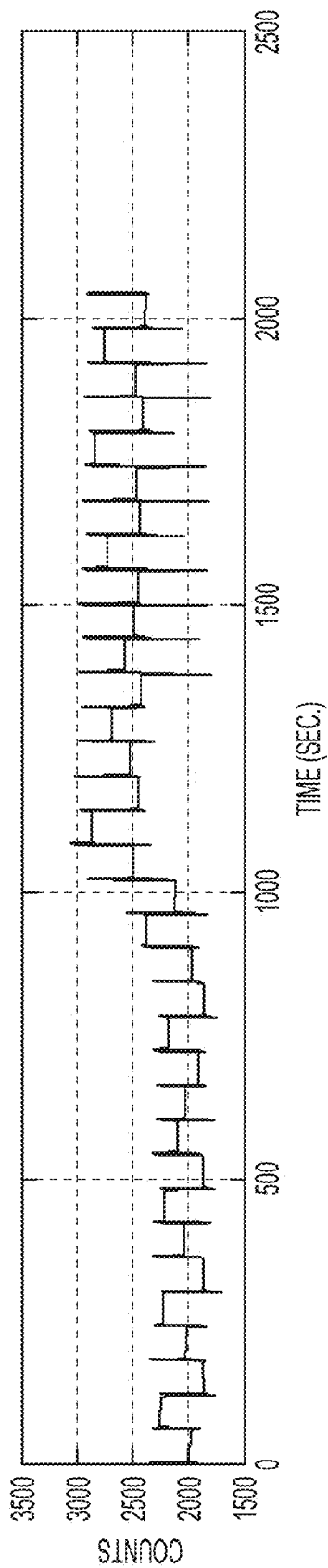
Figure 17F:
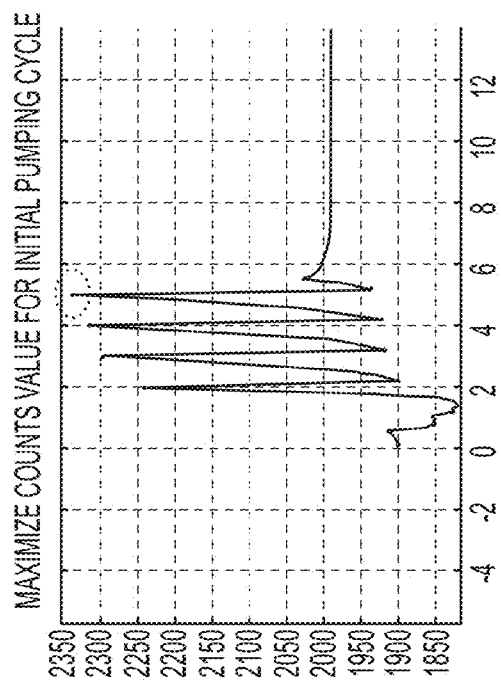

Additionally or alternatively, and as embodied herein, the occlusion sensor can determine a maximum force value detected during an initial pumping cycle, which can be used to establish a baseline maximum. For purpose of illustration and not limitation, FIG. 17E is a diagram illustrating exemplary occlusion sensor counts over time for pump assembly 100 operating at a 5 mL/hr flow rate, with an occlusion introduced into the system at about 900 seconds. FIG. 17F illustrates a detailed portion of the time scale of the diagram of FIG. 17E. For example and without limitation, as shown in FIG. 17F, a maximum counts value of about 2330 is identified at about 5 seconds, and can be established as the baseline maximum counts value. Force values detected during subsequent pumping cycles can be compared to the established baseline maximum. For purpose of illustration and not limitation, when the detected force values during subsequent pumping cycles exceed the baseline maximum by a certain percentage, embodied herein as 10%, the occlusion sensor can determine an occlusion to be present. The percentage threshold can be adjusted to detect occlusions with suitable accuracy while reducing or eliminating false positives.

For purpose of illustration and not limitation, as embodied herein, the baseline maximum can be adjusted at during subsequent pumping cycles. Adjustment of the baseline maximum can account for certain amounts of relaxation of the cassette components that can occur during use or variations between different cassettes. For purpose of illustration and comparison, FIG. 17G illustrates exemplary counts values over time of four different cassettes, illustrating variation of force counts over time within each cassette and overall among the different cassettes. To adjust the baseline maximum, the maximum force value detected during the subsequent pumping cycle can be compared to the baseline maximum. If the maximum force value detected during the subsequent pumping cycle is less than the baseline maximum, the lower maximum force value can become the new baseline maximum, and the detection of force values can be repeated for a subsequent pumping cycle. The adjustment to the baseline maximum can account for a variety of factors, including drift of the tubing. If the maximum force value detected during the subsequent pumping cycle is greater than the baseline maximum, but less than the threshold to detect an occlusion, the current baseline maximum can be maintained, and detection of force values can be repeated for a subsequent pumping cycle. Additionally or alternatively, the baseline maximum can be adjusted to account for changes in flow rate. For purpose of illustration, if the flow rate increase is detected, for example due to a change of flow rate setting or due to delivery of a higher flow rate dose, such as a morning dose or extra dose, a subsequent pumping cycle can be used to establish a new baseline maximum to avoid a false occlusion from being detected. As a further alternative, if a flow rate decrease is detected, for example due to a change of flow rate setting or due to delivery of a lower flow rate dose, such as a normal dose occurring after a morning dose or extra dose, the new baseline maximum can be adjusted as described above in a manner similar to accounting for tubing drift.

Furthermore or as a further alternative, detection of occlusions existing prior to pumping can be performed. Such occlusions can cause pump to exceed suitable pressure for an extended amount of time, and the time to detect an occlusion before suitable pressure is exceeded can be less than that for occlusions developing during pumping. As such, detection of occlusions existing prior to pumping can involve examining force data per pump revolution, that is, for example and not limitation, by detecting local maxima for each pump revolution within a given pumping cycle.

Figure 17H:
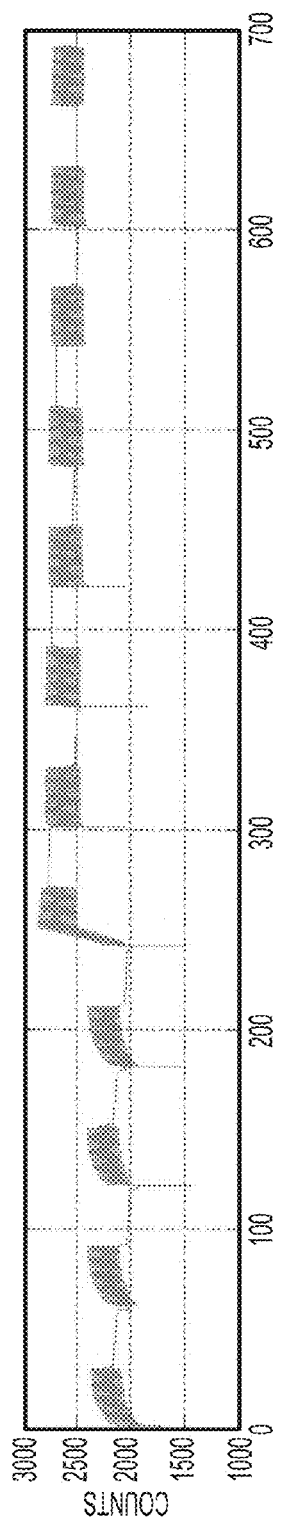
Figure 17I:
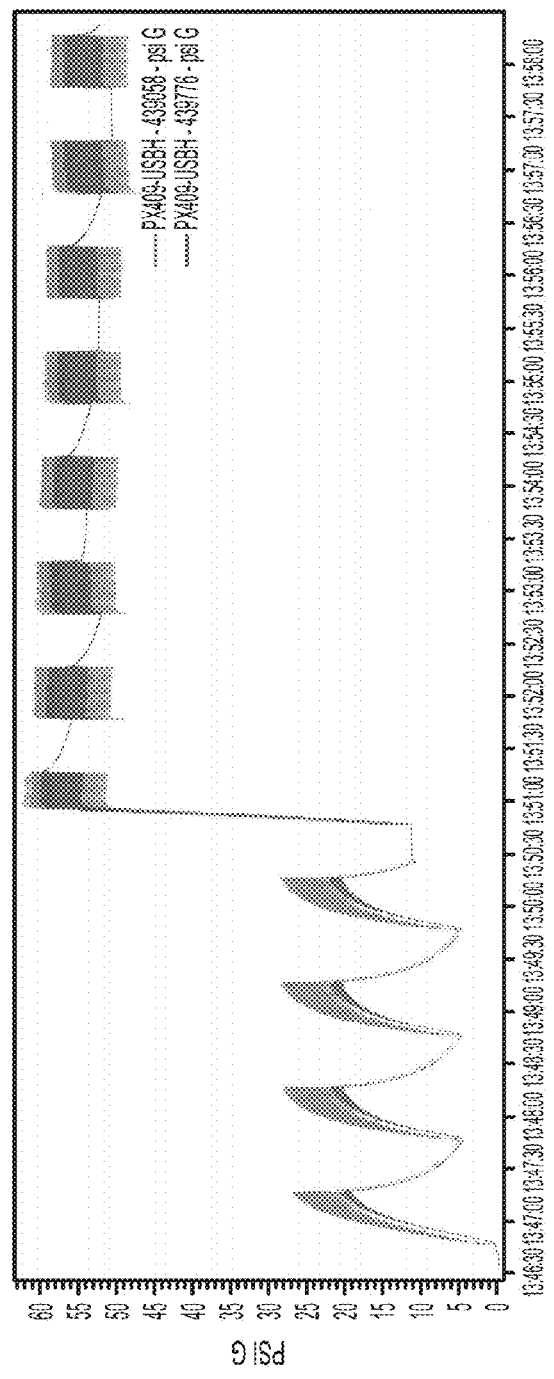

For example and not limitation, FIG. 17H is a diagram illustrating exemplary occlusion sensor counts over time for pump assembly 100 operating at a 40 mL/hr flow rate, with an occlusion introduced into the system at about 250 seconds. For purpose of illustration and comparison, FIG. 17I is a diagram illustrating exemplary pressure data from independent pressure sensor data corresponding to the pump assembly 100 operation of FIG. 17H. As shown in FIG. 17I, a first pressure sensor 439058 is disposed on the cassette housing, and a second pressure sensor 439776 is disposed at a connection between the tubing system joined to the cassette and a patient administration set tubing.

Additionally, for purpose of illustration, and not limitation, FIG. 17J illustrates a detailed portion of the time scale of the diagram of FIG. 17H. As shown in FIG. 17J, for example and without limitation, a single pump revolution can be detected within a pumping cycle. Additionally or alternatively, a single pump revolution can be detected, for example and as embodied herein using motor rotation data from encoder 3b. As embodied herein, a maximum force during the single pump revolution can be detected and established as a reference maximum. For purpose of illustration, as embodied herein, a pump revolution after the initial pump revolution can be the single pump revolution to establish the reference maximum, for example and without limitation the third pump revolution after an initial pump revolution can be used to avoid initial pumping behavior, which can mimic a preexisting occlusion, affecting the established reference. For each subsequent pump revolution after the established reference, a maximum force can be detected and compared to the reference maximum. For purpose of illustration, and not limitation, FIG. 17K is a diagram illustrating exemplary occlusion sensor counts over time for pump assembly 100 operating at a 40 mL/hr flow rate. As shown in FIG. 17K, maximum and minimum forces for each pump revolution are identified with dots on the exemplary waveform. For purpose of illustration, and not limitation, FIG. 17L is a diagram illustrating further exemplary occlusion sensor counts over time for pump assembly 100 operating at a 40 mL/hr flow rate. As shown in FIG. 17L, a reference maximum (referred to as a reference counts value) is identified and compared to maximum force counts values for subsequent pump revolutions. For purpose of illustration and not limitation, when the detected maximum force exceeds the reference maximum by a certain percentage, which can be chosen for example and without limitation within a range of 13% to 55%, and as embodied herein can be 55%, the occlusion sensor can determine an occlusion to be present. The percentage threshold can be adjusted to detect occlusions with suitable accuracy while reducing or eliminating false positives. The occlusion sensor can be configured to examine local force maxima for detection of occlusions only when the flow rate is above a certain flow rate, for example and without limitation, embodied herein at 10 mL/hr. Lower flow rates can provide additional time to detect an occlusion using other techniques without examining the local force maxima during each pump revolution. Additionally or alternatively, for purpose of illustration, the occlusion sensor can be configured to examine local force maxima for detection of occlusions only for a predetermined number of pump revolutions, for example and embodied herein as nine pump revolutions, after an initial pump revolution during fluid delivery. As a further alternative, the local force minima and maxima can be adjusted as described above with respect to the baseline maximum for a pumping cycle, for example and without limitation to account for changes in flow rate, as described above.

Figure 17M:
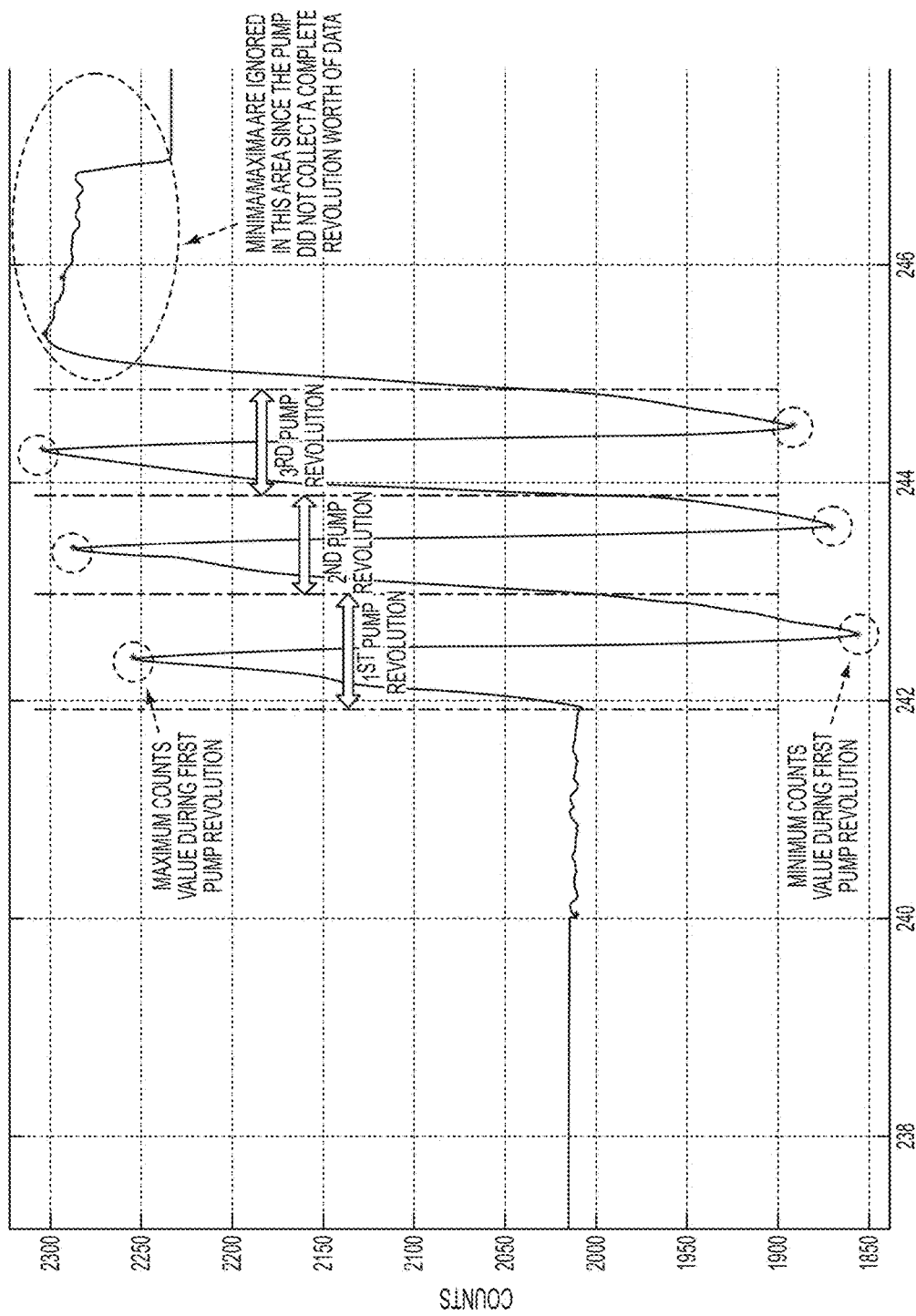

In addition or as an additional alternative, detection of other failures can be performed by the occlusion sensor. For example and without limitation, as illustrated in FIG. 17M, pump drivetrain failure (e.g., due to a broken camshaft or other drive train component) or occlusion sensor signal conditioning circuitry failure can produce a relatively flat force sensor waveform over time. As such, both minimum and maximum force can be determined for each pump revolution in a pumping cycle. As shown for example in FIG. 17M, if the maximum force does not exceed the minimum force by a certain threshold, the occlusion sensor can indicate an error.

According to another aspect of the disclosed subject matter, and further to the above, exemplary techniques for graphical user interfaces for a device for delivering a beneficial agent to a user are provided. For purpose of illustration and not limitation, FIGS. 18A-1 to 18A-4 together are a schematic diagram illustrating exemplary techniques 1700 and associated graphical user interface screens for delivering a beneficial agent to a user. For example and without limitation, at 1701, a blank screen can be displayed on display 218, indicating that the pump is not operational and first processor 306 is in a hibernation state. A user can press any input button in communication with button PCB assembly 224, as shown for example in FIGS. 11A-11B, to signal second processor 308 to awaken first processor 306 from a hibernation state to an active state and activate display 218. At 1702, a splash screen on display 218 can provide an indication to the user that first processor 306 and display 218 are active. At 1710, if a morning dose has not yet been delivered within a certain time period, the display 218 can prompt a user to initiate a morning dose, as discussed further below. At 1703, if the morning dose has already been delivered within a certain time period, the display 218 can prompt a user to initiate a normal dose. If the user selects to start normal delivery of a dose, at 1704, pump assembly 100 can be activated to deliver a dose for a predetermined flow rate, as described herein, and display 218 can provide a visual indication that the normal dose is being delivered. The display 218 can indicate, for purpose of illustration and not limitation, a remaining drug life time, a time until drug cartridge depletion, a flow rate, and an indication of the progress of the normal dose. At 1705, during delivery of the normal dose, a user can press an extra dose button to request an extra dose and can press a cancel button to cancel a dose. At 1706, if the user presses the extra dose button, and a number of extra doses exceeds a predetermined limit for a time period, display 218 can indicate that the extra dose option is locked out, and can further indicate when the option for an extra dose will become available. At 1707, display 218 indicates that the extra dose option is available. At 1708, if the user presses the extra dose button while it is available, pump assembly 100 can be activated to deliver a dose for a predetermined flow rate, as described herein, and display 218 can provide a visual indication that the normal dose is being delivered.

For purpose of illustration and not limitation, FIG. 18B is a flow chart illustrating additional details of exemplary techniques to deliver a morning dose. For example and without limitation, as described above with respect to 1710, if a morning dose has not yet been delivered within a certain time period, the display 218 can prompt a user to initiate a morning dose. To determine if a morning dose has been delivered, a morning dose lockout check can be performed. For example and without limitation, as embodied herein, when a morning dose is delivered at 1710, a morning dose lockout timer is set for a predetermined period of time, embodied herein as 18 hours. Additionally, as embodied herein, when a new cassette is detected, at 1712, a morning dose lockout check is performed. That is, at 1713, the morning dose lockout timer is checked to see if the lockout timer has expired and/or if a new cassette has been installed. If the lockout timer has not expired, or a new cassette has not been installed, the lockout check exits at 1717 and the user is prompted at screen 1703 to start a normal dose. If the lockout timer has expired and a new cassette has been installed, at 1714, a morning dose icon is cleared from display 218. At 1715, an extra dose counter is reset to 0. At 1716, an existing event log file is closed and a new event log file is opened. The lockout check exits at 1717 and proceeds to 1710 to prompt the user to initiate a morning dose.

For purpose of illustration and not limitation, FIGS. 18C-1 to 18C-2 and 18D-1 to 18D-4 are schematic diagrams illustrating additional details of exemplary techniques to allow a clinician to access settings for pump assembly 100. For example and without limitation, at 1721, a blank screen can be displayed on display 218, indicating that the pump is not operational and first processor 306 is in a hibernation state, e.g., powered down. A clinician can press any input button in communication with button PCB assembly 224, as shown for example in FIGS. 11A-11B, to signal second processor 308 to awaken, e.g. activate, first processor 306 from a hibernation state to an active state and activate display 218. At 1722, a splash screen on display 218 can provide an indication to the clinician that first processor 306 and display 218 are active. Further at 1722, the clinician can press and hold a button, embodied herein as a bolus button, for a predetermined period of time to enter a code entry screen. At 1723, the clinician can be prompted to enter a clinician code to access menu options available to a clinician having the clinician code. At 1724, the clinician can select a clinician settings option to view and change a number of clinician settings. For purpose of illustration and not limitation, as embodied herein, clinician settings can include settings for high, medium and low flow rates that can be chosen by a patient, an extra dose flow rate, and a morning dose flow rate. At 1725, the clinician can select a patient settings option to view and change a number of settings for a patient. For purpose of illustration and not limitation, at 1726, patient settings can include a flow rate minimum, a flow rate maximum, and extra dose flow rate limit, and extra dose lockout period, a morning dose flow rate limit, and a morning dose lockout period. Additionally or alternatively, patient settings can include a morning dose enable/disable setting and/or an extra dose enable/disable. As embodied herein, if morning dose is disabled, the morning dose confirmation screens can be skipped. Additionally or alternatively, if extra dose is disabled, a notification screen can be displayed indicating the extra dose is disabled.

Each of the components described herein can be made of any suitable material (e.g., plastic, composites, metal, etc.) and technique for its intended purpose. In addition to the specific embodiments claimed below, the disclosed subject matter is also directed to other embodiments having any other possible combination of the dependent features claimed below and those disclosed above. As such, the particular features disclosed herein can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

The devices and techniques of the disclosed subject matter can be used for delivery of any of a variety of suitable fluid substances of corresponding volume or dose.

While the disclosed subject matter is described herein in terms of certain preferred embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A peristaltic pump for delivery of a beneficial agent to a user, comprising:
   a motor;
   a cam shaft coupled to the motor for rotation about a longitudinal axis of the cam shaft, the cam shaft having a radially-outward projection defining a helical engagement portion disposed continuously along a length of the cam shaft; and
   a plurality of finger plates disposed along the length of the cam shaft, each finger plate mounted for movement in a transverse direction relative to the longitudinal axis of the cam shaft, each finger plate having an aperture defined therein to receive the cam shaft therethrough, each aperture defined by a substantially straight edge region and an opposing edge region, each finger plate further having a substantially flat surface contacting an adjacent finger plate and a recessed area within and surrounded by the surface, the recessed area being configured to reduce surface friction between the contacting surfaces of the adjacent finger plates;
   wherein engagement of the helical engagement portion with the substantially straight edge region of each finger plate during rotation of the cam shaft urges the finger plate transversely toward an extended position.

2. The peristaltic pump of claim 1, wherein each finger plate is free of transverse movement as the helical engagement portion passes along at least a portion of the opposing edge region thereof during rotation of the cam shaft.

3. The peristaltic pump of claim 1, wherein the opposing edge region comprises an arcuate edge.

4. The peristaltic pump of claim 1, wherein the recessed area is disposed proximate the aperture of the finger plate.

5. The peristaltic pump of claim 1, wherein the recessed area is recessed 0.1 mm relative the surface of the finger plate.

6. The peristaltic pump of claim 1, wherein each finger plate comprises an end surface at an end facing the direction of the transverse movement, and wherein the recessed area is spaced from the end surface.

7. The peristaltic pump of claim 1, wherein each finger plate comprises an end surface at an end facing the direction of the transverse movement, and wherein the end surfaces of the finger plates together define a contiguous surface facing the direction of the transverse movement.

8. The peristaltic pump of claim 1, wherein each finger plate is unbiased.

9. The peristaltic pump of claim 1, wherein each finger plate is biased away from the extended position.

10. The peristaltic pump of claim 1, wherein the plurality of finger plates are disposed parallel with each other and arranged for sequential movement toward the extended position.

11. The peristaltic pump of claim 1, further comprising a gap defined between an end plate of the plurality of finger plates and an interior wall of the peristaltic pump, the peristaltic pump further comprising a filler plate disposed within the gap.

12. The peristaltic pump of claim 11, wherein the filler plate has a different thickness than each of the plurality of finger plates, the different thickness being less than each of the plurality of finger plates.

13. The peristaltic pump of claim 11, wherein the filler plate has a different thickness than each of the plurality of finger plates, the different thickness being greater than each of the plurality of finger plates.

14. The peristaltic pump of claim 1, wherein the substantially straight edge region has a thickness greater than the opposing edge region.

15. The peristaltic pump of claim 1, wherein each finger plate comprises a ceramic material.

16. The peristaltic pump of claim 1, wherein the camshaft comprises a ceramic material.

17. The peristaltic pump of claim 1, further comprising one or more bevel gears coupling the motor to the cam shaft.

18. The peristaltic pump of claim 1, wherein the cam shaft comprises a chamfered portion formed at a radial end of the helical engagement portion.

19. The peristaltic pump of claim 1, wherein the helical engagement portion extends around the cam shaft greater than one revolution of the helical engagement portion.

20. The peristaltic pump of claim 1, further comprising:
 a cassette including a cassette housing with a fluid reservoir defined therein, a delivery tube fluidly coupled with the fluid reservoir, the cassette housing having a cassette base region; and
 a pump housing having a receiving region to receive the cassette base region, the plurality of finger plates disposed proximate the receiving region.

21. The peristaltic pump of claim 20, wherein each finger plate compresses a portion of the delivery tube in the extended position.

22. The peristaltic pump of claim 21, wherein when the cam shaft rotates out of engagement with the substantially straight edge region of each finger plate, the delivery tube is configured to urge the finger plate away from the extended position.

23. The peristaltic pump of claim 21, wherein the plurality of finger plates are disposed parallel with each other and arranged for sequential movement toward the extended position to sequentially compress the delivery tube to create a vacuum force to draw the beneficial agent from the fluid reservoir.

24. The peristaltic pump of claim 20, further comprising a beneficial agent contained in the fluid reservoir.

25. The peristaltic pump of claim 21, wherein the beneficial agent comprises one or more of levodopa and carbidopa.

26. The peristaltic pump of claim 1, wherein the recessed area is spaced from the substantially straight edge region.

27. The peristaltic pump of claim 26, wherein the recessed area has a contoured edge having a middle and opposing ends, the middle being spaced further from the substantially straight edge region than the opposing ends are from the substantially straight edge region.

28. The peristaltic pump of claim 4, wherein the recessed area is disposed between the aperture of the finger plate and an end surface at an end facing the direction of the transverse movement.

29. The peristaltic pump of claim 27, wherein the contoured edge is configured to strengthen the substantially straight edge region.

* * * * *